United States Patent
Hummel et al.

(10) Patent No.: US 11,306,343 B2
(45) Date of Patent: *Apr. 19, 2022

(54) 3α-HYDROXYSTEROID DEHYDROGENASE MUTANTS AND PROCESS FOR THE PREPARATION OF URSODEOXYCHOLIC ACID

(71) Applicant: PharmaZell GmbH, Raubling (DE)

(72) Inventors: Werner Hummel, Titz (DE); Daniel Bakonyi, Cologne (DE)

(73) Assignee: PHARMAZELL GMBH

( * ) Notice: Subject to any disclaimer, the term of this patent is extended or adjusted under 35 U.S.C. 154(b) by 0 days.

This patent is subject to a terminal disclaimer.

(21) Appl. No.: 16/561,643

(22) Filed: Sep. 5, 2019

(65) Prior Publication Data

US 2019/0390242 A1  Dec. 26, 2019

Related U.S. Application Data

(63) Continuation of application No. 15/327,887, filed as application No. PCT/EP2015/068514 on Aug. 12, 2015, now Pat. No. 10,487,348.

(30) Foreign Application Priority Data

Aug. 12, 2014 (EP) .................. 14180614

(51) Int. Cl.
*C12N 9/04* (2006.01)
*C12N 15/00* (2006.01)
*C12N 15/53* (2006.01)
*C12N 1/20* (2006.01)
*C12P 33/00* (2006.01)
*C12P 13/02* (2006.01)
*C12P 33/02* (2006.01)

(52) U.S. Cl.
CPC ............ *C12P 33/02* (2013.01); *C12N 9/0006* (2013.01); *C12Y 101/0105* (2013.01); *C12Y 101/01159* (2013.01); *C12Y 101/01225* (2013.01)

(58) Field of Classification Search
None
See application file for complete search history.

(56) References Cited

U.S. PATENT DOCUMENTS

| | | | |
|---|---|---|---|
| 2008/0206833 A1* | 8/2008 | Yamaoka | C12Q 1/32 435/190 |
| 2013/0040341 A1 | 2/2013 | Liu et al. | |
| 2013/0224792 A1 | 8/2013 | Schmid et al. | |
| 2014/0087421 A1 | 3/2014 | Weuster-Botz et al. | |

FOREIGN PATENT DOCUMENTS

| | | |
|---|---|---|
| WO | 2011064404 A1 | 6/2011 |
| WO | 2012080504 A1 | 6/2012 |

OTHER PUBLICATIONS

International Search Report of the International Searching Authority dated Aug. 13, 2015 for PCT/EP2015/068514.
Database UniProt [Online], Apr. 18, 2012, Database accession No. H5XOP5.
Database UniProt [Online], Jun. 11, 2014, Database accession No. A0A022FPP9.
Database UniProt [Online], Nov. 13, 2013, Database accession No. T2H6F4.
Notification of Transmittal of translation of the International Preliminary Report on Patentability issued for PCT Application No. PCT/EP2015/068514, filed Aug. 12, 2015.
Chang, Y. H. et al., "Role of S114 in the NADH-induced conformational change and catalysis of 3-alpha-hydroxysteroid dehydrogenase/carbonyl reductase from Comamonas testosteroni" Biochimica ET Biophysica ACTA (BBA), Proteins & Protemics, Elsevier, Netherlands, vol. 1794, No. 10 (2009).
Chi-Chang Hwang, et. al., "The Catalytic Roles of P185 and T188 and Substrate-Binding Loop Flexibility in 3 [alpha]-Hydroxysteriod Dehydrogenase/Carbonyl Reductase from Comamonas testosteroni", PLoS One, vol. 8, No. 5 (2013).
Bovara, et. al., Biotechnol. Lett. 1996, 305-308.
Monti, et. al., Adv. Synth. Catal. 2009, 351, 1303-1311.
Higashi, et. al., Gastroenterologia Japonica 1979, 14, 417-424.
Liu, et. al., Appl. Microbial. Biotechnol. 2011, 90, 127-135.
Carrea, et. al., Biotechnol. Lett.1 992, 14, 1131-1135, 1992.
Liu, et. al., Appl. Microbial. Biotechnol. 2013, 97, 633-639.
Zhu, et. al., Tetrahedron 2006, 62(18), p. 4535-4539.
MacDonald, et. al., Biochim Biophys Acta 1981 , 665(2), p. 262-9.
Narang, S.A. Tetrahedron 1983, 39, 3-22.
Itakura, et. al., Annu. Rev. Biochem. 1984, 53,323 ff.
Itakura, et. al., Science 1984, 198, 1056 ff.
Ike, et. al., Nucleic Acids Res. 1983, 11,477.
Arkin, et. al., PNAS 1992, 89, 7811-7815.
Delagrave, et. al., Protein Engineering 1993, 6(3), 327-331.
E. Maser, et. al., "Functional Expression. Purification , and Characterization of 3a-Hydroxysteroid Dehydrogenase/Carbonyl Reductase from Comamonas Testosteroni," Biochemicai and Biophysical Research Communications 272, 622-628, (20 00), 2000.

\* cited by examiner

*Primary Examiner* — David Steadman
(74) *Attorney, Agent, or Firm* — Saul Ewing Arnstein & Lehr LLP; Brian R. Landry; Justin W. Crotty

(57) ABSTRACT

The invention provides novel 3α-hydroxysteroid dehydrogenase mutants, sequences that code for these enzyme mutants, methods for producing the enzyme mutants, and the use thereof in enzymatic reactions of cholic acid compounds, and in particular in the production of ursodeoxycholic acid (UDCA). The invention further provides processes for the synthesis of UDCA using the enzyme mutants and the production of UDCA using recombinant microorganisms that have been subjected to multiple modifications.

28 Claims, 12 Drawing Sheets

Specification includes a Sequence Listing.

7β-HSDH *Collinsella aerofaciens*
Accession:   ZP_01773061
  1 mnlrekygew glilgategv gkafcekiaa ggmnvvmvgr reeklnvlag eiretygvet
 61 kvvradfsqp gaaetvfaat egldmgfmsy vaclhsfgki qdtpwekhea minvnvvtfl
121 kcfhhymrif aaqdrgavin vssmtgisss pwngqygagk afilkmteav acecegtgvd
181 vevitlgttl tpsllsnlpg gpqgeavmki altpeecvde afeklgkels viagqrnkds
241 vhdwkanhte deyirymgsf yrd

Fig. 2A

7β-HSDH *Collinsella aerofaciens*
Accession NO: NZ_AAVN02000010, Region: 52005..52796
  1 atgaacctga gggagaagta cggtgagtgg ggcctgatcc tgggcgcgac cgagggcgtc
 61 ggcaaggcgt tctgcgagaa gatcgccgcc ggcggcatga acgtcgtcat ggtcggccgt
121 cgcgaggaga agctgaacgt gctcgcaggc gagatccgcg agacctacgg cgtggagacc
181 aaggtcgtgc gcgccgactt tagccagccc ggcgctgccg agaccgtctt cgccgcgacc
241 gagggcctgg acatgggctt catgagctac gtggcctgcc tgcacagctt cggtaagatc
301 caggacaccc cctgggagaa gcacgaggcc atgatcaacg tcaacgtcgt gaccttcctc
361 aagtgcttcc accactacat gcggatcttt gccgcccagg accgcggcgc cgtgatcaac
421 gtctcgtcga tgaccggcat cagctccagc ccctggaacg gccagtacgg cgcgggcaag
481 gccttcatcc tcaagatgac cgaggccgtg gcctgcgagt gcgagggcac cggcgtcgac
541 gtcgaggtca tcaccctcgg caccacccta accccagcc tgctgtccaa cctccccggc
601 ggcccgcagg gcgaggccgt catgaagatc gccctcaccc ccgaggagtg cgttgacgag
661 gcctttgaga agctgggtaa ggagctctcc gtcatcgccg gccagcgcaa caaggactcc
721 gtccacgact ggaaggcaaa ccacaccgag gacgagtaca tccgctacat ggggtcgttc
781 taccgcgact ag

Fig. 2B

3α-HSDH

Source: *Comamonas testosteroni* ATCC 11996

```
  1 msiivisgca tgigaatrkv leaaghqivg idirdaevia dlstaegrkq aiadvlakcs
 61 kgmdglvlca glgpqtkvlg nvvsvnyfga telmdaflpa lkkghqpaav vissvasahl
121 afdknplala leageeakar aivehageqg gnlayagskn altvavrkra aawgeagvrl
181 ntiapgatet pllqaglqdp rygesiakfv ppmgrraeps emasviaflm spaasyvhga
241 qividggida vmrptqf
```

Fig. 2C

Nucleic acid sequence coding for 3α-HSDH

Source: *Comamonas testosteroni* ATCC 11996

Accession: AF092031, Region: 158..931

```
  1 atgtccatca tcgtgataag cggctgcgcc accggcattg gtgcggctac gcgcaaggtc
 61 ctggaggcgg ccggtcacca gatcgtaggc atcgatatac gcgatgcgga agtgattgcc
121 gatctctcga cggccgaagg tcgaaagcag gcgattgccg atgtactggc gaagtgcagc
181 aagggcatgg acggcctggt gctgtgcgcc ggcctgggac cgcagaccaa ggtgcttggc
241 aatgtggttt cggtcaatta ttttggcgcg accgagctga tggatgcctt tttgccagcg
301 ctgaaaaaag gccatcagcc cgcagccgtc gtcatctcgt ccgtggcttc cgcgcatctg
361 gcttttgaca agaacccact ggcgctggca ctggaagccg gcgaggaagc caaggcccgc
421 gccattgtcg aacatgcggg agagcagggc ggaaatctgg cctatgcggg cagcaagaat
481 gctttgacgg tggctgtgcg caaacgcgcc gccgcctggg gcgaggctgg cgtgcgcctg
541 aacaccatcg ccccggtgc aaccgagact ccccttgctgc aggcgggcct gcaggacccg
601 cgctatggcg aatccattgc caagttcgtt cctcccatgg gccgccgtgc cgagccgtcc
661 gagatggcgt cggtcatcgc cttttttgatg agcccggccg caagctatgt gcatggcgcg
721 cagatcgtca ttgatggcgg cattgatgcg gtgatgcgcc cgacacagtt ctga
```

Fig. 2D

3α-HSDH (wild type); 257 AA; 27.5kDa

```
         10         20         30         40         50         60
MSIIVISGCA TGIGAATRKV LEAAGHQIVG IDIRDAEVIA DLSTAEGRKQ AIADVLAKCS 70         80         90        100        110        120
KGMDGLVLCA GLGPQTKVLG NVVSVNYFGA TELMDAFLPA LKKGHQPAAV VISSVASAHL 130        140        150        160        170        180
AFDKNPLALA LEAGEEAKAR AIVEHAGEQG GNLAYAGSKN ALTVAVRKRA AAWGEAGVRL 190        200        210        220        230        240
NTIAPGATET PLLQAGLQDP RYGESIAKFV PPMGRRAEPS EMASVIAFLM SPAASYVHGA 250        260
QIVIDGGIDA VMRPTQFLEH HHHHH
```

Fig. 3A

3α-HSDH [R34N]; 257 AA; 27.4kDa

```
         10         20         30         40         50         60
MSIIVISGCA TGIGAATRKV LEAAGHQIVG IDINDAEVIA DLSTAEGRKQ AIADVLAKCS 70         80         90        100        110        120
KGMDGLVLCA GLGPQTKVLG NVVSVNYFGA TELMDAFLPA LKKGHQPAAV VISSVASAHL 130        140        150        160        170        180
AFDKNPLALA LEAGEEAKAR AIVEHAGEQG GNLAYAGSKN ALTVAVRKRA AAWGEAGVRL 190        200        210        220        230        240
NTIAPGATET PLLQAGLQDP RYGESIAKFV PPMGRRAEPS EMASVIAFLM SPAASYVHGA 250        260
QIVIDGGIDA VMRPTQFLEH HHHHH
```

Fig. 3B

3α-HSDH [L68A]; 257 AA; 27.4kDa

```
          10         20         30         40         50         60
  MSIIVISGCA TGIGAATRKV LEAAGHQIVG IDIRDAEVIA DLSTAEGRKQ AIADVLAKCS 70         80         90        100        110        120
  KGMDGLVCCA GLGPQTKVLG NVVSVNYFGA TELMDAFLPA LKKGHQPAAV VISSVASAHL 130        140        150        160        170        180
  AFDKNPLALA LEAGEEAKAR AIVEHAGEQG GNLAYAGSKN ALTVAVRKRA AAWGEAGVRL 190        200        210        220        230        240
  NTIAPGATET PLLQAGLQDP RYGESIAKFV PPMGRRAEPS EMASVIAFLM SPAASYVHGA 250        260
  QIVIDGGIDA VMRPTQFLEH HHHHH
```

Fig. 3C

3α-HSDH [R34N/L68A]; 257 AA; 27.4kDa

```
          10         20         30         40         50         60
  MSIIVISGCA TGIGAATRKV LEAAGHQIVG IDINDAEVIA DLSTAEGRKQ AIADVLAKCS 70         80         90        100        110        120
  KGMDGLVACA GLGPQTKVLG NVVSVNYFGA TELMDAFLPA LKKGHQPAAV VISSVASAHL 130        140        150        160        170        180
  AFDKNPLALA LEAGEEAKAR AIVEHAGEQG GNLAYAGSKN ALTVAVRKRA AAWGEAGVRL 190        200        210        220        230        240
  NTIAPGATET PLLQAGLQDP RYGESIAKFV PPMGRRAEPS EMASVIAFLM SPAASYVHGA 250        260
  QIVIDGGIDA VMRPTQFLEH HHHHH
```

Fig. 3D

SEQUENCE LISTING

<160> NUMBER OF SEQ ID NOS: 57

<210> SEQ ID NO 1
<211> LENGTH: 792
<212> TYPE: DNA
<213> ORGANISM: Colinsella aerofaciens
<220> FEATURE:
<221> NAME/KEY: CDS
<222> LOCATION: (1)..(789)

<400> SEQUENCE: 1

```
atg aac ctg agg gag aag tac ggt gag tgg ggc ctg atc ctg ggc gcg      48
Met Asn Leu Arg Glu Lys Tyr Gly Glu Trp Gly Leu Ile Leu Gly Ala
1               5                   10                  15 acc gag ggc gtc ggc aag gcg ttc tgc gag aag atc gcc gcc ggc ggc      96
Thr Glu Gly Val Gly Lys Ala Phe Cys Glu Lys Ile Ala Ala Gly Gly
                20                  25                  30 atg aac gtc gtc atg gtc ggc cgt cgc gag gag aag ctg aac gtg ctc     144
Met Asn Val Val Met Val Gly Arg Arg Glu Glu Lys Leu Asn Val Leu
            35                  40                  45 gca ggc gag atc cgc gag acc tac ggc gtg gag acc aag gtc gtg cgc     192
Ala Gly Glu Ile Arg Glu Thr Tyr Gly Val Glu Thr Lys Val Val Arg
        50                  55                  60 gcc gac ttt agc cag ccc ggc gct gcc gag acc gtc ttc gcc gcg acc     240
Ala Asp Phe Ser Gln Pro Gly Ala Ala Glu Thr Val Phe Ala Ala Thr
65                  70                  75                  80 gag ggc ctg gac atg ggc ttc atg agc tac gtg gcc tgc ctg cac agc     288
Glu Gly Leu Asp Met Gly Phe Met Ser Tyr Val Ala Cys Leu His Ser
                85                  90                  95 ttc ggt aag atc cag gac acc ccc tgg gag aag cac gag gcc atg atc     336
Phe Gly Lys Ile Gln Asp Thr Pro Trp Glu Lys His Glu Ala Met Ile
                100                 105                 110 aac gtc aac gtc gtg acc ttc ctc aag tgc ttc cac cac tac atg cgg     384
Asn Val Asn Val Val Thr Phe Leu Lys Cys Phe His His Tyr Met Arg
            115                 120                 125 atc ttt gcc gcc cag gac cgc ggc gcc gtg atc aac gtc tcg tcg atg     432
Ile Phe Ala Ala Gln Asp Arg Gly Ala Val Ile Asn Val Ser Ser Met
        130                 135                 140
```

```
acc ggc atc agc tcc agc ccc tgg aac ggc cag tac ggc gcg ggc aag      480
Thr Gly Ile Ser Ser Ser Pro Trp Asn Gly Gln Tyr Gly Ala Gly Lys
145                 150                 155                 160 gcc ttc atc ctc aag atg acc gag gcc gtg gcc tgc gag tgc gag ggc      528
Ala Phe Ile Leu Lys Met Thr Glu Ala Val Ala Cys Glu Cys Glu Gly
                165                 170                 175 acc ggc gtc gac gtc gag gtc atc acc ctc ggc acc acc cta acc ccc      576
Thr Gly Val Asp Val Glu Val Ile Thr Leu Gly Thr Thr Leu Thr Pro
            180                 185                 190 agc ctg ctg tcc aac ctc ccc ggc ggc ccg cag ggc gag gcc gtc atg      624
Ser Leu Leu Ser Asn Leu Pro Gly Gly Pro Gln Gly Glu Ala Val Met
        195                 200                 205 aag atc gcc ctc acc ccc gag gag tgc gtt gac gag gcc ttt gag aag      672
Lys Ile Ala Leu Thr Pro Glu Glu Cys Val Asp Glu Ala Phe Glu Lys
    210                 215                 220 ctg ggt aag gag ctc tcc gtc atc gcc ggc cag cgc aac aag gac tcc      720
Leu Gly Lys Glu Leu Ser Val Ile Ala Gly Gln Arg Asn Lys Asp Ser
225                 230                 235                 240 gtc cac gac tgg aag gca aac cac acc gag gac gag tac atc cgc tac      768
Val His Asp Trp Lys Ala Asn His Thr Glu Asp Glu Tyr Ile Arg Tyr
                245                 250                 255 atg ggg tcg ttc tac cgc gac tag                                       792
Met Gly Ser Phe Tyr Arg Asp
            260

<210> SEQ ID NO 2
<211> LENGTH: 263
<212> TYPE: PRT
<213> ORGANISM: Colinsella aerofaciens

<400> SEQUENCE: 2

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
                20                  25                  30

Met Asn Val Val Met Val Gly Arg Arg Glu Glu Lys Leu Asn Val Leu
            35                  40                  45

Ala Gly Glu Ile Arg Glu Thr Tyr Gly Val Glu Thr Lys Val Val Arg
        50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205
```

```
Lys Ile Ala Leu Thr Pro Glu Glu Cys Val Asp Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 3
<211> LENGTH: 774
<212> TYPE: DNA
<213> ORGANISM: Comamonas testosteroni
<220> FEATURE:
<221> NAME/KEY: CDS
<222> LOCATION: (1)..(771)

<400> SEQUENCE: 3
```

| | | | | | | | | | | | | | | | | |
|---|---|---|---|---|---|---|---|---|---|---|---|---|---|---|---|---|
| atg | tcc | atc | atc | gtg | ata | agc | ggc | tgc | gcc | acc | ggc | att | ggt | gcc | gct | 48 |
| Met | Ser | Ile | Ile | Val | Ile | Ser | Gly | Cys | Ala | Thr | Gly | Ile | Gly | Ala | Ala | |
| 1 | | | | 5 | | | | | 10 | | | | | 15 | | |
| acg | cgc | aag | gtc | ctg | gag | gcg | gcc | ggt | cac | cag | atc | gta | ggc | atc | gat | 96 |
| Thr | Arg | Lys | Val | Leu | Glu | Ala | Ala | Gly | His | Gln | Ile | Val | Gly | Ile | Asp | |
| | | 20 | | | | | 25 | | | | | 30 | | | | |
| ata | cgc | gat | gcg | gaa | gtg | att | gcc | gat | ctc | tcg | acg | gcc | gaa | ggt | cga | 144 |
| Ile | Arg | Asp | Ala | Glu | Val | Ile | Ala | Asp | Leu | Ser | Thr | Ala | Glu | Gly | Arg | |
| | 35 | | | | | 40 | | | | | 45 | | | | | |
| aag | cag | gcg | att | gcc | gat | gta | ctg | gcg | aag | tgc | agc | aag | ggc | atg | gac | 192 |
| Lys | Gln | Ala | Ile | Ala | Asp | Val | Leu | Ala | Lys | Cys | Ser | Lys | Gly | Met | Asp | |
| 50 | | | | | 55 | | | | | 60 | | | | | | |
| ggc | ctg | gtg | ctg | tgc | gcc | ggc | ctg | gga | ccg | cag | acc | aag | gtg | ctt | ggc | 240 |
| Gly | Leu | Val | Leu | Cys | Ala | Gly | Leu | Gly | Pro | Gln | Thr | Lys | Val | Leu | Gly | |
| 65 | | | | | 70 | | | | | 75 | | | | | 80 | |
| aat | gtg | gtt | tcg | gtc | aat | tat | ttt | ggc | gcg | acc | gag | ctg | atg | gat | gcc | 288 |
| Asn | Val | Val | Ser | Val | Asn | Tyr | Phe | Gly | Ala | Thr | Glu | Leu | Met | Asp | Ala | |
| | | | | 85 | | | | | 90 | | | | | 95 | | |
| ttt | ttg | cca | gcg | ctg | aaa | aaa | ggc | cat | cag | ccc | gca | gcc | gtc | gtc | atc | 336 |
| Phe | Leu | Pro | Ala | Leu | Lys | Lys | Gly | His | Gln | Pro | Ala | Ala | Val | Val | Ile | |
| | | | 100 | | | | | 105 | | | | | 110 | | | |
| tcg | tcc | gtg | gct | tcc | gcg | cat | ctg | gct | ttt | gac | aag | aac | cca | ctg | gcg | 384 |
| Ser | Ser | Val | Ala | Ser | Ala | His | Leu | Ala | Phe | Asp | Lys | Asn | Pro | Leu | Ala | |
| | | 115 | | | | | 120 | | | | | 125 | | | | |
| ctg | gca | ctg | gaa | gcc | ggc | gag | gaa | gcc | aag | gcc | cgc | gcc | att | gtc | gaa | 432 |
| Leu | Ala | Leu | Glu | Ala | Gly | Glu | Glu | Ala | Lys | Ala | Arg | Ala | Ile | Val | Glu | |
| | 130 | | | | | 135 | | | | | 140 | | | | | |
| cat | gcg | gga | gag | cag | ggc | gga | aat | ctg | gcc | tat | gcg | ggc | agc | aag | aat | 480 |
| His | Ala | Gly | Glu | Gln | Gly | Gly | Asn | Leu | Ala | Tyr | Ala | Gly | Ser | Lys | Asn | |
| 145 | | | | | 150 | | | | | 155 | | | | | 160 | |
| gct | ttg | acg | gtg | gct | gtg | cgc | aaa | cgc | gcc | gcc | gcc | tgg | ggc | gag | gct | 528 |
| Ala | Leu | Thr | Val | Ala | Val | Arg | Lys | Arg | Ala | Ala | Ala | Trp | Gly | Glu | Ala | |
| | | | 165 | | | | | 170 | | | | | 175 | | | |
| ggc | gtg | cgc | ctg | aac | acc | atc | gcc | ccc | ggt | gca | acc | gag | act | ccc | ttg | 576 |
| Gly | Val | Arg | Leu | Asn | Thr | Ile | Ala | Pro | Gly | Ala | Thr | Glu | Thr | Pro | Leu | |
| | | | 180 | | | | | 185 | | | | | 190 | | | |
| ctg | cag | gcg | ggc | ctg | cag | gac | ccg | cgc | tat | ggc | gaa | tcc | att | gcc | aag | 624 |
| Leu | Gln | Ala | Gly | Leu | Gln | Asp | Pro | Arg | Tyr | Gly | Glu | Ser | Ile | Ala | Lys | |
| | | 195 | | | | | 200 | | | | | 205 | | | | |
| ttc | gtt | cct | ccc | atg | ggc | cgc | cgt | gcc | gag | ccg | tcc | gag | atg | gcg | tcg | 672 |
| Phe | Val | Pro | Pro | Met | Gly | Arg | Arg | Ala | Glu | Pro | Ser | Glu | Met | Ala | Ser | |
| | 210 | | | | | 215 | | | | | 220 | | | | | |

```
gtc atc gcc ttt ttg atg agc ccg gcc gca agc tat gtg cat ggc gcg    720
Val Ile Ala Phe Leu Met Ser Pro Ala Ala Ser Tyr Val His Gly Ala
225                 230                 235                 240 cag atc gtc att gat ggc ggc att gat gcg gtg atg cgc ccg aca cag    768
Gln Ile Val Ile Asp Gly Gly Ile Asp Ala Val Met Arg Pro Thr Gln
            245                 250                 255 ttc tga                                                             774
Phe
```

<210> SEQ ID NO 4
<211> LENGTH: 257
<212> TYPE: PRT
<213> ORGANISM: Comamonas testosteroni

<400> SEQUENCE: 4

```
Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Arg Asp Ala Glu Val Ile Ala Asp Leu Ser Thr Ala Glu Gly Arg
        35                  40                  45

Lys Gln Ala Ile Ala Asp Val Leu Ala Lys Cys Ser Lys Gly Met Asp
    50                  55                  60

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Ala Val Val Ile
            100                 105                 110

Ser Ser Val Ala Ser Ala His Leu Ala Phe Asp Lys Asn Pro Leu Ala
        115                 120                 125

Leu Ala Leu Glu Ala Gly Glu Glu Ala Lys Ala Arg Ala Ile Val Glu
    130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Trp Gly Glu Ala
                165                 170                 175

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe
```

<210> SEQ ID NO 5
<211> LENGTH: 265
<212> TYPE: PRT
<213> ORGANISM: Artificial Sequence
<220> FEATURE:
<223> OTHER INFORMATION: Description of Artificial Sequence: Synthetic
      3alpha HSDH WT + HIS tag polypeptide

<400> SEQUENCE: 5

```
Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Arg Asp Ala Glu Val Ile Ala Asp Leu Ser Thr Ala Glu Gly Arg
        35                  40                  45

Lys Gln Ala Ile Ala Asp Val Leu Ala Lys Cys Ser Lys Gly Met Asp
    50                  55                  60

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Val Val Ile
            100                 105                 110

Ser Ser Val Ala Ser Ala His Leu Ala Phe Asp Lys Asn Pro Leu Ala
            115                 120                 125

Leu Ala Leu Glu Ala Gly Glu Glu Lys Ala Arg Ala Ile Val Glu
        130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Ala Trp Gly Glu Ala
                165                 170                 175

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe Leu Glu His His His His His His
            260                 265

<210> SEQ ID NO 6
<211> LENGTH: 265
<212> TYPE: PRT
<213> ORGANISM: Artificial Sequence
<220> FEATURE:
<223> OTHER INFORMATION: Description of Artificial Sequence: Synthetic
      3alpha-HSDH [R34N] polypeptide

<400> SEQUENCE: 6

Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Asn Asp Ala Glu Val Ile Ala Asp Leu Ser Thr Ala Glu Gly Arg
        35                  40                  45

Lys Gln Ala Ile Ala Asp Val Leu Ala Lys Cys Ser Lys Gly Met Asp
    50                  55                  60

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
```

```
                    85                  90                  95
Phe Leu Pro Ala Leu Lys Lys Gly His Gln Pro Ala Val Val Ile
            100                 105                 110
Ser Ser Val Ala Ser Ala His Leu Ala Phe Asp Lys Asn Pro Leu Ala
            115                 120                 125
Leu Ala Leu Glu Ala Gly Glu Glu Ala Lys Ala Arg Ala Ile Val Glu
            130                 135                 140
His Ala Gly Glu Gln Gly Gly Asn Leu Ala Tyr Ala Gly Ser Lys Asn
145                 150                 155                 160
Ala Leu Thr Val Ala Val Arg Lys Arg Ala Ala Ala Trp Gly Glu Ala
                    165                 170                 175
Gly Val Arg Leu Asn Thr Ile Ala Pro Gly Ala Thr Glu Thr Pro Leu
                    180                 185                 190
Leu Gln Ala Gly Leu Gln Asp Pro Arg Tyr Gly Glu Ser Ile Ala Lys
            195                 200                 205
Phe Val Pro Pro Met Gly Arg Arg Ala Glu Pro Ser Glu Met Ala Ser
            210                 215                 220
Val Ile Ala Phe Leu Met Ser Pro Ala Ala Ser Tyr Val His Gly Ala
225                 230                 235                 240
Gln Ile Val Ile Asp Gly Gly Ile Asp Ala Val Met Arg Pro Thr Gln
                    245                 250                 255
Phe Leu Glu His His His His His His
            260                 265

<210> SEQ ID NO 7
<211> LENGTH: 265
<212> TYPE: PRT
<213> ORGANISM: Artificial Sequence
<220> FEATURE:
<223> OTHER INFORMATION: Description of Artificial Sequence: Synthetic
      3alpha-HSDH [L68A] polypeptide

<400> SEQUENCE: 7

Met Ser Ile Ile Val Ile Ser Gly Cys Ala Thr Gly Ile Gly Ala Ala
1               5                   10                  15
Thr Arg Lys Val Leu Glu Ala Ala Gly His Gln Ile Val Gly Ile Asp
                    20                  25                  30
Ile Arg Asp Ala Glu Val Ile Ala Asp Leu Ser Thr Ala Glu Gly Arg
            35                  40                  45
Lys Gln Ala Ile Ala Asp Val Leu Ala Lys Cys Ser Lys Gly Met Asp
50                  55                  60
Gly Leu Val Cys Cys Ala Gly Leu Gly Pro Gln Thr Lys Val Leu Gly
65                  70                  75                  80
Asn Val Val Ser Val Asn Tyr Phe Gly Ala Thr Glu Leu Met Asp Ala
                    85                  90                  95
Phe Leu Pro Ala Leu Lys Lys Gly His Gln Pro Ala Val Val Ile
            100                 105                 110
Ser Ser Val Ala Ser Ala His Leu Ala Phe Asp Lys Asn Pro Leu Ala
            115                 120                 125
Leu Ala Leu Glu Ala Gly Glu Glu Ala Lys Ala Arg Ala Ile Val Glu
            130                 135                 140
His Ala Gly Glu Gln Gly Gly Asn Leu Ala Tyr Ala Gly Ser Lys Asn
145                 150                 155                 160
Ala Leu Thr Val Ala Val Arg Lys Arg Ala Ala Ala Trp Gly Glu Ala
                    165                 170                 175
```

```
Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
            245                 250                 255

Phe Leu Glu His His His His His His
        260                 265

<210> SEQ ID NO 8
<211> LENGTH: 265
<212> TYPE: PRT
<213> ORGANISM: Artificial Sequence
<220> FEATURE:
<223> OTHER INFORMATION: Description of Artificial Sequence: Synthetic
      3alpha-HSDH [R34N/L68A] polypeptide

<400> SEQUENCE: 8

Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Asn Asp Ala Glu Val Ile Ala Asp Leu Ser Thr Ala Glu Gly Arg
        35                  40                  45

Lys Gln Ala Ile Ala Asp Val Leu Ala Lys Cys Ser Lys Gly Met Asp
    50                  55                  60

Gly Leu Val Ala Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Ala Val Val Ile
            100                 105                 110

Ser Ser Val Ala Ser Ala His Leu Ala Phe Asp Lys Asn Pro Leu Ala
        115                 120                 125

Leu Ala Leu Glu Ala Gly Glu Glu Ala Lys Ala Arg Ala Ile Val Glu
    130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Ala Trp Gly Glu Ala
                165                 170                 175

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
            245                 250                 255

Phe Leu Glu His His His His His His
        260                 265
```

<210> SEQ ID NO 9
<211> LENGTH: 401
<212> TYPE: PRT
<213> ORGANISM: Mycobacterium vaccae

<400> SEQUENCE: 9

```
Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
```

```
                    370                 375                 380
Gly Asn Ala Thr Gly Gly Ser Glu Glu Ala Ala Lys Phe Lys Lys Ala
385                 390                 395                 400

Val

<210> SEQ ID NO 10
<211> LENGTH: 786
<212> TYPE: DNA
<213> ORGANISM: Bacillus subtilis
<220> FEATURE:
<221> NAME/KEY: CDS
<222> LOCATION: (1)..(783)

<400> SEQUENCE: 10 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
                20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
            35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
        50                  55                  60 gat gtc acg aaa gag gaa gat gta aaa aat atc gtg caa acg gca att      240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gaa      288
Lys Glu Phe Gly Thr Leu Asp Ile Met Ile Asn Asn Ala Gly Leu Glu
                85                  90                  95 aat cct gtg cca tct cac gaa atg ccg ctc aag gat tgg gat aaa gtc      336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att      384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc      432
Lys Tyr Phe Val Glu Asn Asp Ile Lys Gly Asn Val Ile Asn Met Ser
130                 135                 140 agt gtg cac gaa gtg att cct tgg ccg tta ttt gtc cac tat gcg gca      480
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac      528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac      576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat      624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc      672
Val Glu Ser Met Ile Pro Met Gly Tyr Ile Gly Glu Pro Glu Glu Ile
210                 215                 220 gcc gca gta gca gcc tgg ctt gct tcg aag gaa gcc agc tac gtc aca      720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc      768
```

```
Gly Ile Thr Leu Phe Ala Asp Gly Gly Met Thr Gln Tyr Pro Ser Phe
                245                 250                 255 cag gca ggc cgc ggt taa                                              786
Gln Ala Gly Arg Gly
            260
```

<210> SEQ ID NO 11
<211> LENGTH: 261
<212> TYPE: PRT
<213> ORGANISM: Bacillus subtilis

<400> SEQUENCE: 11

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcatcgata taaacgatgc ggaagtg                                          27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacttccgca tcgtttatat cgatgcc                                           27

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcgtaggcat cgatatactc gatgcggaag tgat                                   34

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atcacttccg catcgagtat atcgatgcct acga                                   34

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accagatcgt aggcatcgat ataagcgatg cggaag                                 36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttccgcatc gcttatatcg atgcctacga tctggt                                 36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
accagatcgt aggcatcgat atatgcgatg cggaag                                 36

```
<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttccgcatc gcatatatcg atgcctacga tctggt                              36

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggacggcctg gtgtcgtgcg ccggcctg                                       28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caggccggcg cacgacacca ggccgtcc                                       28

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggacggcctg gtgtgctgcg ccggcctgg                                      29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccaggccggc gcagcacacc aggccgtcc                                      29

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggacggcctg gtgaagtgcg ccggcctg                                       28

<210> SEQ ID NO 25
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caggccggcg cacttcacca ggccgtcc                                         28

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acggcctggt ggtgtgcgcc ggc                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gccggcgcac accaccaggc cgt                                              23

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gacggcctgg tggcgtgcgc cggcct                                           26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aggccggcgc acgccaccag gccgtc                                           26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aacaccatcg ccgccggtgc aaccg                                            25

<210> SEQ ID NO 31
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cggttgcacc ggcggcgatg gtgtt                                              25

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaacaccatc gccggcggtg caaccgag                                           28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctcggttgca ccgccggcga tggtgttc                                           28

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaacaccatc gccaccggtg caaccga                                            27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcggttgcac cggtggcgat ggtgttc                                            27

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctgaacacca tcgccgtcgg tgcaaccgag ac                                      32

<210> SEQ ID NO 37
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
gtctcggttg caccgacggc gatggtgttc ag                                    32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctgaacacca tcgccagcgg tgcaaccgag ac                                    32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtctcggttg caccgctggc gatggtgttc ag                                    32

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgcccccggt gcagccgaga ctcc                                             24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggagtctcgg ctgcaccggg ggcg                                             24

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cccccggtgc aagcgagact ccc                                              23

<210> SEQ ID NO 43
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
gggagtctcg cttgcaccgg ggg                                            23

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atcgcccccg gtgcagtcga gactcccttg                                     30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caagggagtc tcgactgcac cggggggcgat                                    30

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tcgcccccgg tgcaggcgag actcccctt                                      28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aagggagtct cgcctgcacc ggggggcga                                      28

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atcgcccccg gtgcatggga gactcccttg ctg                                 33

<210> SEQ ID NO 49
<211> LENGTH: 33
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 49
cagcaaggga gtctcccatg caccgggggc gat      33

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Glu His His His His His His
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 51

His His His His His His His His His
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Glu His His His
1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Glu His His His His His His His His His
1               5                   10

<210> SEQ ID NO 55

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Met Gly Ser Ser His His His His His His Ser Ser Gly Leu Val Pro
1               5                   10                  15

Arg Gly Ser His
            20

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 1-10 residues

<400> SEQUENCE: 56

His His His His His His His His His His
1               5                   10

<210> SEQ ID NO 57
<211> LENGTH: 774
<212> TYPE: DNA
<213> ORGANISM: Comamonas testosteroni

<400> SEQUENCE: 57
atgtccatca tcgtgataag cggctgcgcc accggcattg gtgcggctac gcgcaaggtc      60
ctggaggcgg ccggtcacca gatcgtaggc atcgatatac gcgatgcgga agtgattgcc     120
gatctctcga cggccgaagg tcgaaagcag gcgattgccg atgtactggc gaagtgcagc     180
aagggcatgg acggcctggt gctgtgcgcc ggcctgggac cgcagaccaa ggtgcttggc     240
aatgtggttt cggtcaatta tttttggcgcg accgagctga tggatgcctt tttgccagcg     300
ctgaaaaaag ccatcagcc cgcagccgtc gtcatctcgt ccgtggcttc cgcgcatctg     360
gcttttgaca agaacccact ggcgctggca ctggaagccg gcgaggaagc caaggcccgc     420
gccattgtcg aacatgcggg agagcagggc ggaaatctgg cctatgcggg cagcaagaat     480
gctttgacgt ggctgtgcg caaacgcgcc gccgcctggg gcgaggctgg cgtgcgcctg     540
aacaccatcg ccccggtgc aaccgagact cccttgctgc aggcgggcct gcaggacccg     600
cgctatggcg aatccattgc caagttcgtt cctcccatgg gccgccgtgc cgagccgtcc     660
gagatggcgt cggtcatcgc ctttttgatg agcccggccg caagctatgt gcatggcgcg     720
cagatcgtca ttgatggcgg cattgatgcg gtgatgcgcc cgacacagtt ctga          774
```

3α-HYDROXYSTEROID DEHYDROGENASE MUTANTS AND PROCESS FOR THE PREPARATION OF URSODEOXYCHOLIC ACID

CROSS-REFERENCE TO RELATED APPLICATIONS

This application is a continuation of U.S. Ser. No. 15/327,887, which issued as U.S. Pat. No. 10,487,348, which is the U.S. national phase, pursuant to 35 U.S.C. § 371, of PCT international application Ser. No. PCT/EP2015/068514, filed Aug. 12, 2015, designating the United States and published in German on Feb. 18, 2016 as publication WO 2016/023933A1, which claims priority under 35 U.S.C. § 119(a) to German patent application No. 14180614.1, filed Aug. 12, 2014. The entire disclosures of the aforementioned patent application are hereby incorporated herein by reference.

SEQUENCE LISTING

The instant application contains a Sequence Listing which has been submitted electronically in ASCII format and is hereby incorporated by reference in its entirety. Said ASCII copy, created on Jun. 13, 2017, is named 054410_00066 (US)_SL.txt and is 43,947 bytes in size.

The invention relates to novel 3α-hydroxysteroid dehydrogenase (3α-HSDH) mutants, in particular the 3α-HSDH of *Comamonas testosteroni* (formerly referred to as *Pseudomonas testosteroni*), to the sequences which code for these enzyme mutants, to processes for the preparation of the enzyme mutants and to their use in enzymatic conversions of cholic acid compounds, in particular in the preparation of ursodeoxycholic acid (UDCA); subject-matter of the invention is also novel processes for the synthesis of UDCA using enzyme mutants; and the preparation of UDCA using recombinant, multiply modified microorganisms.

BACKGROUND OF THE INVENTION

Bile acids are biomolecules which are required for the digestion and absorption of fats, fatty acids and hydrophobic vitamins. A bile acid which is found, in humans, in small amounts only is ursodeoxycholic acid (referred to as UDCA). It has recently gained great therapeutic importance in the dissolution of cholesterol-comprising gallstones. This compound is produced industrially in ton-quantities by chemical or enzymatic steps. An important precursor for the synthesis of UDCA is 12-ketoursodeoxycholic acid, which can be converted into UDCA by a Wolff-Kishner reduction. A route, described in the literature, for the synthesis of 12-ketoursodeoxycholic acid starts with cholic acid (3α,7α,12α-trihydroxy-5β-cholanic acid), which may be prepared by two oxidative steps which are catalyzed by 7α- and 12α-HSDHs, and one reductive step, catalyzed by a 7β-HSDH (Bovara R et al. (1996) A new enzymatic route to the synthesis of 12-ketoursodeoxycholic acid. Biotechnol. Lett. 18:305-308; Monti D et al. (2009) One-pot multienzymatic synthesis of 12-ketoursodeoxycholic acid: Subtle cofactor specificities rule the reaction equilibria of five biocatalysts working in a row. Adv. Synth. Catal. 351:1303-1311). A further route starts with 7-ketolithocholic acid, which may be converted into UDCA by stereoselectively reducing the 7-keto group; this step, too, is advantageously carried out with enzymatic catalysis, catalyzed by a 7β-HSDH (Higashi S et al. (1979) Conversion of 7-keto-lithocholic acid to ursodeoxycholic acid by human intestinal anaerobic microorganisms: Interchangeability of chenodeoxycholic acid and ursodeoxycholic acid. *Gastroenterologia Japonica* 14:417-424; Liu L et al. (2011) Identification, cloning, heterologous expression, and characterization of a NADPH-dependent 7 beta-hydroxysteroid dehydrogenase from *Collinsella aerofaciens*. Appl. Microbiol. Biotechnol. 90:127-135). A further advantageous synthetic route starts with dehydrocholic acid (DHCA), which may be converted into 12-ketoursodeoxycholic acid by two reductive steps; these two steps may be catalyzed by two stereoselective HSDHs (3α- and 7β-HSDHs) (Carrea G et al. (1992) Enzymatic synthesis of 12-ketoursodeoxycholic acid from dehydrocholic acid in a membrane reactor. Biotechnol. Lett. 14:1131-1135; Liu L et al. (2013) One-step synthesis of 12-ketoursodeoxycholic acid from dehydrocholic acid using a multienzymatic system. Appl. Microbiol. Biotechnol. 97:633-639).

The enzyme from *C. aerofaciens* has proved to be a very suitable 7β-HSDH. The gene sequence of this enzyme from *C. aerofaciens* is now known, so that firstly the enzyme can be made available recombinantly after cloning; secondly, it is possible to generate mutants of this enzyme by protein engineering methods and therefore optionally to find more advantageous enzyme variants, as may be the case.

The enzyme from *C. testosteroni* has proved to be a very suitable 3α-HSDH. The gene sequence of this enzyme is now known, so that firstly the enzyme can be made available recombinantly after cloning; secondly, it is possible to generate mutants of this enzyme by protein engineering methods and therefore optionally to find more advantageous enzyme variants, as may be the case.

The active substances ursodeoxycholic acid (UDCA) and its diastereomer chenodesoxycholic acid (CDCA) have, inter alia, been employed for many years as medicaments for the treatment of gallstone complaints. The two compounds differ merely by the configuration of the hydroxyl group on C atom 7 (UDCA: β-configuration, CDCA: α-configuration). To prepare UDCA, a variety of processes are described in the prior art, and these processes are carried out by purely chemical means or else as a combination of chemical and enzymatic process steps. The starting point is in each case cholic acid (CA), or CDCA, which is prepared starting from cholic acid.

Thus, FIG. 1A shows diagrammatically the traditional chemical method for the preparation of UDCA.

A severe disadvantage of the traditional chemical method is, inter alia, the following: because the chemical oxidation is not selective, the carboxyl group and the 3α- and 7α-hydroxy group must be protected by esterification.

FIG. 1B shows an alternative chemical/enzymatic process based on the use of the enzyme 12α-hydroxysteroid dehydrogenase (12α-HSDH) that is described, for example, in PCT/EP2009/002190 of the present applicant. Here, the 12α-HSDH oxidizes CA selectively to give 12-keto-CDCA. The two protective steps which are required by the traditional chemical method can be dispensed with here.

FIG. 1C shows diagrammatically an alternative enzymatic/chemical process that is disclosed in Monti, D., et al., (*One-Pot Multienzymatic Synthesis of* 12-*Ketoursodeoxycholic Acid: Subtle Cofactor Specificities Rule the Reaction Equilibria of Five Biocatalysts Working in a Row*. Advanced Synthesis & Catalysis, 2009).

The CA is oxidized first by the 7α-HSDH enzyme from *Bacteroides fragilis* ATCC 25285 (Zhu, D., et al., *Enzymatic enantioselective reduction of-ketoesters by a thermostable 7-hydroxysteroid dehydrogenase from Bacteroides fragilis.*

Tetrahedron, 2006. 62(18): p. 4535-4539) and 12α-HSDH to give 7,12-diketo-LCA. These two enzymes are in each case NADH-dependent. After the reduction by 7β-HSDH (NADPH-dependent) from *Clostridium absonum* ATCC 27555 (DSM 599) (MacDonald, I. A. and P. D. Roach, *Bile induction of 7 alpha-and 7 beta-hydroxysteroid dehydrogenases in Clostridium absonum*. Biochim Biophys Acta, 1981. 665(2): p. 262-9), 12-keto-UDCA results. A Wolff-Kishner reduction gives the end product. The disadvantage of this process is that a complete conversion is not possible due to the equilibrium situation of the catalyzed reaction, and that two different enzymes must be employed in the first step of the reaction, which makes the process more expensive. Lactate dehydrogenase (LDH; for regenerating NAD$^+$) and glucose dehydrogenase (GlcDH or GDH, for regenerating NADPH) are employed for cofactor regeneration. The disadvantage of the cofactor regeneration used in that reaction is that the co-product which forms can only be removed with great difficulty from the reaction mixture, so that the reaction equilibrium cannot be influenced positively, which brings about incomplete conversion of the starting material.

A 7β-HSDH from the strain *Collinsella aerofaciens* ATCC 25986 (DSM 3979; previously *Eubacterium aerofaciens*) was described in 1982 by Hirano and Masuda (Hirano, S. and N. Masuda, *Characterization of NADP-dependent 7 beta-hydroxysteroid dehydrogenases from Peptostreptococcus productus and Eubacterium aerofaciens*. Appl Environ Microbiol, 1982. 43(5): p. 1057-63). Sequence information for that enzyme was not disclosed. The molecular weight as determined by gel filtration amounted to 45 000 Da (cf. Hirano, page 1059, left-hand column). Furthermore, the reduction of the 7-oxo group to the 7β-hydroxy group could not be observed for said enzyme (cf. Hirano, page 1061, discussion, 1$^{st}$ paragraph). A person skilled in the art can therefore see that the enzyme described by Hirano et al. is not suitable for catalyzing the reduction of dehydrocholic acid (referred to herein as DHCA) in the 7-position to give 3,12-diketo-7β-CA.

The applicant's earlier international patent application PCT/EP2010/068576 describes a novel 7β-HSDH from *Collinsella aerofaciens* ATCC 25986, which has, inter alia, a molecular weight (as determined by SDS gel electrophoresis) of approximately 28-32 kDa, a molecular weight (as determined by gel filtration, under non-denaturing conditions, such as, in particular without SDS): of approximately 53 to 60 kDa, and the ability of stereoselectively reducing the 7-carbonyl group of 7-keto-LCA to a 7β-hydroxy group.

Furthermore, FIG. 1C shows diagrammatically a process for the preparation of UDCA described in PCT/EP2010/068576.

Thus, CA is oxidized in a simple manner via the traditional chemical route. The DHCA is reduced by the enzyme pair 7β-HSDH and 3α-HSDH, individually one after the other or else in one pot, to give 12-keto-UDCA. In combination with Wolff-Kishner reduction, UDCA can thus be synthesized in only three steps, starting from CA. While the 7β-HSDH enzyme is dependent on the cofactor NADPH, the 3α-HSDH enzyme requires the cofactor NADH. The availability of enzyme pairs which are dependent on the same cofactor or with extended dependence (for example on the cofactors NADH and NADPH) would be advantageous because it could simplify cofactor regeneration.

WO 2012/080504 describes novel 7β-HSDH mutants from *C. aerofaciens* in the sequence region of the amino acid radicals 36 to 42 of the *C. aerofaciens* sequence, and biocatalytic processes for the preparation of UDCA, in particular also novel whole-cell processes, where 7β-HSDH and 3α-HSDH act together on the substrate.

WO 2011/147957 describes novel knock-out strains which are particularly suitable for the preparation of UDCA since it has been possible to switch off the undesired 7α-HSDH enzyme activity in targeted fashion.

Hwang et al. mention in PLOS ONE (2013), 8, 5, e63594 specific single mutants (P185A, G or W; T188A, S or W) and dual mutants (W173F/P185W and W173F/T188W) of the 3α-HSDH from *C. testosteronii*. These mutants, which possess N-His tags, are proposed for the NAD-dependent oxidation of the substrate androsterone. Other substrates are not discussed.

The problem of the present invention is the provision of further improved 3α-HSDHs. In particular, it was intended to provide enzyme mutants which can be employed even more advantageously for the enzymatic or microbial preparation of UDCA via the stereospecific reduction of DHCA 3-position, and which have in particular an improved activity for substrate and/or cofactor, and/or of a reduced substrate inhibition and/or altered cofactor utilization (increased, modified specificity or widened dependency).

SUMMARY OF THE INVENTION

Surprisingly, it was possible to solve the above problems by generating and characterizing improved mutants of 3α-HSDH from aerobic bacteria of the genus *Comamonas*, in particular of the strain *Comamonas testosteroni*, and by employing them in the conversion of cholic acid compounds, in particular the production of UDCA.

On the basis of structural and homology aspects, it has been attempted in accordance with the invention to define sequence regions which might be responsible for coenzyme binding or else for substrate recognition. This results in possibilities in modifying, in a targeted fashion, amino acids in these regions by means of mutagenesis so as to modify enzyme properties by such structural modifications. Thus, what is known as the "Rossmann fold", which is responsible for coenzyme binding, in the region of the amino acids around approximately 8 to 68 in the case of the 3α-HSDH of *Comamonas testosteroni*. In accordance with the invention, it has now been attempted in particular to modify amino acids in this coenzyme binding region such that the enzyme accepts the NADPH instead of NADH. During the attempt of replacing the amino acid leucine in position 68 by alanine it has been found, surprisingly, that this 3α-HSDH mutant has a markedly higher activity. This has subsequently also been confirmed in as far as a plurality of further mutants, all of which had mutations in position 68, showed higher activities than the wild-type enzyme. Even enzyme mutants which had been purified to homogeneity and which had been compared with the correspondingly purified wild-type enzyme demonstrated markedly higher specific enzyme activities.

The improved activity can be identified clearly by the increase in the specific activity, in other words the activity value, based on the amount of protein, of the mutants 3α-HSDH [R34N], 3α-HSDH [R34C], 3α-HSDH [L68A], 3α-HSDH [L68C], 3α-HSDH [L68K], 3α-HSDH [L68S] and of the dual mutant 3α-HSDH [R34N/L68A]. An exchange of an amino acid is denoted by the spelling; for example, R34N means that the arginine (R) in position 34 has been replaced by asparagine (N). The 3α-HSDH which may be obtained from *C. testosteroni*, or this enzyme provided with a C-terminal hexahistidine (His) tag (SEQ ID NO: 52), is referred to as the wild-type enzyme.

Furthermore, there have been found, surprisingly, markedly improved specific activities in single mutants, such as, for example, 3α-HSDH [T188A], 3α-HSDH [T188S], and dual mutants such as, for example, 3α-HSDH [L68A/T188A] or 3α-HSDH [L68A/T188S], in respect of the substrates CDCA and/or NADH.

Furthermore, the above problem has been solved by providing a biocatalytic (microbial and/or enzymatic) process, comprising the enzymatic conversion of DHCA into 12-keto-UDCA via two reductive part-steps catalyzed by the 3α-HSDH mutants and 7β-HSDH described herein, which may occur simultaneously or staggered in any sequence, and cofactor regeneration by using dehydrogenases, which regenerate the consumed cofactor from both reductive part-steps.

BRIEF DESCRIPTION OF THE DRAWINGS

FIG. 2A shows the amino acid sequence of the *Collinsella aerofaciens* 7β-HSDH (SEQ ID NO:2), FIG. 2B shows the coding nucleic acid sequence (SEQ ID NO: 1) for the amino acid sequence of FIG. 2A; FIG. 2C shows the amino acid sequence of the *Comamonas testosteroni* 3α-HSDH (SEQ ID NO: 4), and FIG. 2D shows the coding nucleic acid sequence (SEQ ID NO: 57) for the amino acid sequence of Figure C.

FIG. 3A shows the amino acid sequence of the *Comamonas testosteroni* 3α-HSDH (SEQ ID NO: 5); C-terminally extended by the His-Tag sequence LEHHHHHH (SEQ ID NO: 50); FIG. 3B shows the mutant 3α-HSDH [R34N] derived therefrom (SEQ ID NO: 6); FIG. 3C shows the mutant 3α-HSDH [L68A] derived therefrom (SEQ ID NO: 7); and FIG. 3D shows the mutant 3α-HSDH [R34N/L68A] derived therefrom (SEQ ID NO: 8).

SPECIFIC EMBODIMENTS OF THE INVENTION

Figure 1A:
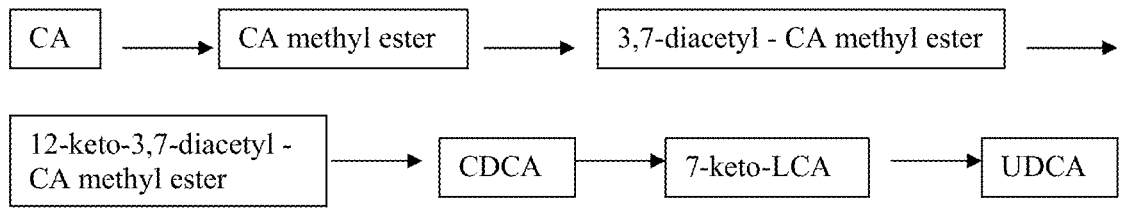
FIG. 1A shows diagrammatically the traditional method for the preparation of UDCA.
Figure 1B:
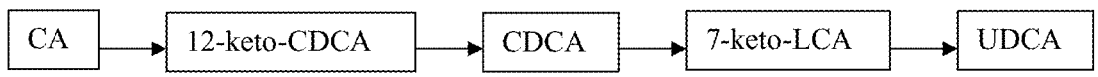
FIG. 1B shows diagrammatically an alternative chemical/enzymatic process for the preparation of UDCA based on the use of the enzyme 12α-hydroxysteroid dehydrogenase (12α-HSDH).
Figure 1C:
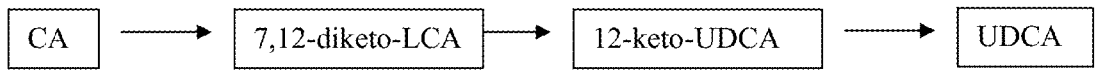
FIG. 1C shows diagrammatically a further alternative process for the preparation of UDCA.
Figure 1D:
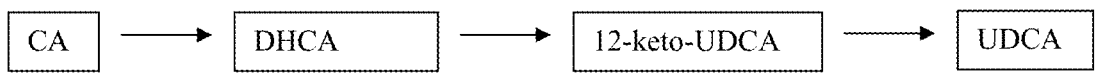
FIG. 1D shows diagrammatically yet another process for the preparation of UDCA.

In particular, the invention relates to the following specific embodiments:

1. 3α-hydroxysteroid dehydrogenase (3α-HSDH) that catalyzes at least the stereospecific enzymatic reduction of a 3-ketosteroid to the corresponding 3-hydroxysteroid (such as, for example, of 3,12-diketo-7β-CA or DHCA to 12-keto-UDCA or 7,12-diketo-3α-CA (7,12-diketo-LCA), in particular under stoichiometric consumption of NADH and/or NADPH, in particular NADH), wherein the enzyme comprises a mutation at position 34 and/or 68 of SEQ ID NO:4 or at the corresponding sequence positions of an amino acid sequence derived therefrom with at least 80% sequence identity, such as, for example, at least such as, for example, 85, 90, 91, 92, 93, 94, 95, 96, 97, 98, 99 or 99.5% sequence identity to SEQ ID NO:4; and/or C-terminally includes a chain extension by up to 25, in particular by up to 15, 14, 13, 12, 11 or 10 identical or different (proteinogenic) amino acid radicals, in particular by a peptide chain comprising 1 to 10, such as, for example, 3 to 9, basic amino acid radicals, such as lysine, arginine or in particular histidine (such as 3×His, 6×His (SEQ ID NO: 52) or 9×His (SEQ ID NO: 51)); it being possible for the histidine residues to be bonded directly to the C-terminus or via a linker group comprising any 1 to 10, in particular 1 to 3, amino acid radicals. Examples which may be mentioned are: LEHHH (SEQ ID NO: 53), LEHHHHHH (SEQ ID NO: 50) and LEHHHHHHHHH (SEQ ID NO: 54). Subject matter are furthermore those 3α-HSDHs which additionally to one or more of the above mutations, or as an alternative thereto, include an N-terminal chain extension by up to 25 identical or different amino acid radicals. These are extended by up to 25, 24, 23, 22, 21, 20, 19, 18, 17, 16, 15, 14, 13, 12, 11 or 10 identical or different (proteinogenic) amino acid radicals, in particular by a peptide chain comprising 1 to 10, such as, for example, 3 to 9, basic amino acid radicals, such as lysine, arginine or in particular histidine (such as 3×His, 6×His (SEQ ID NO: 52) or 9×His (SEQ ID NO: 51)); it being possible for the histidine residues to be bonded directly to the N terminus or via a linker group comprising any 1 to 10 amino acid radicals. An example which may be mentioned is: MGSSHHHHHHSSGLVPRGSH— (SEQ ID NO: 55).

2. 3α-HSDH that catalyzes at least the stereospecific enzymatic reduction of a 3-ketosteroid to the corresponding 3-hydroxysteroid, and which has an amino acid sequence which is modified by amino acid mutation in SEQ ID NO:4, the amino acid sequence mutation being selected among single or multiple mutations comprising:

a. R34X$_1$ and/or b. L68X$_2$ where X$_1$ represents an amino acid radical which is other than arginine (R), in particular a proteinogenic amino acid radical, in particular an amino acid which increases any specific activity and/or which reduces substrate inhibition and/or which modifies cofactor utilization or cofactor dependency, in particular a natural amino acid;

is; and

X$_2$ represents a proteinogenic amino acid radical which is other than leucine (L), in particular an amino acid which increases any specific activity and/or which reduces substrate inhibition and/or which modifies cofactor utilization or cofactor dependency, in particular a natural amino acid;

c) addition mutants which are extended C-terminally by a chain comprising 1 to 10 histidine (H) residues (SEQ ID NO: 56); it being possible for example for the histidine residues to be bonded directly to the C terminus or via a linker group comprising 1 to 10, in particular 1 to 3, amino acid radicals.

d) addition mutants which are extended N-terminally by 1 to 10 histidine (H) residues (SEQ ID NO: 56); it being possible for example for the histidine residues to be bonded directly to the C terminus or via a linker group comprising 1 to 10 amino acid radicals.

the mutated, i.e. modified, amino acid sequence having a sequence identity to SEQ ID NO:4 of 80% to less than 100%, such as, for example, 85, 90, 91, 92, 93, 94, 95, 96, 97, 98, 99 or 99.5% sequence identity.

3. 3α-HSDH as per one of the preceding claims, selected among a) the single mutants R34X$_1$ and L68X$_2$ and the b) the dual mutants

R34X$_1$/L68X$_2$, wherein

X$_1$ represents N, C, S or L;

X$_2$ represents A, G, C, K, S or V, wherein particularly preferred combinations of X$_1$, X$_2$; comprise X$_1$=N and/or X$_2$=A c) addition mutants which are extended C-terminally by a peptide chain comprising 1 to 10 histidine residues (SEQ ID NO: 56); it being possible for example for the histidine residues to be bonded directly to the C terminus or via a linker group comprising 1 to 10, in particular 1 to 3, amino acid radicals;

d) addition mutants which are extended N-terminally by a peptide chain comprising 1 to 10 histidine residues (SEQ ID NO: 56); it being possible for example for the histidine residues to be bonded directly to the N terminus or via a linker group comprising 1 to 10 amino acid radicals and e) mutants as per a) and b), in each case additionally comprising the addition mutation as per c) and/or d), in particular as per c) or d).

Non-limiting examples of suitable mutants are single mutants comprising: [R34N], [R34C], [R34S], [R34L], [L68A], [I68C], [L68K], [L68S], [L68V] and [L68G]

dual mutants comprising: [R34N/L68A]

in each case both without His tag and with C-terminal and/or N-terminal His tag.

4. 3α-HSDH as per one of the previous claims, which, in comparison with the native, unmutated 3α-HSDH with SEQ ID NO:4 shows the following property profile:

a. an increased specific activity (Vmax [U/mg]) for dehydrocholic acid (DHCA) in the enzymatic reduction of DHCA with NADH as cofactor; wherein, for example, the specific activity (U/mg) in the presence of the cofactor NAD(P)H in comparison with the unmutated enzyme is increased by at least 1, 5, 10, 50 or 100%, but in particular at least by 1-fold, in particular by 2- to 100-fold or 3- to 20-fold or 5- to 10-fold, b. a reduced substrate inhibition by DHCA, such as, for example, with Ki values in the range of from >10 mM, such as, for example, at 11 to 200 mM, 12 to 150 mM, 15 to 100 mM, c. it being possible for these properties a) and b) to be present individually or in any combination, i.e. only a), only b), only c), a) and b), a) and c) or b) and c).

5. 3α-hydroxysteroid dehydrogenase (3α-HSDH) which catalyzes at least the stereospecific enzymatic reduction of a 3-ketosteroid to the corresponding 3-hydroxysteroid (such as, for example, of 3,12-diketo-7β-CA or DHCA to 12-keto-UDCA or 7,12-diketo-3α-CA (7,12-diketo-LCA), in particular with stoichiometric consumption of NADH and/or NADPH, especially with stoichiometric consumption of NADH, wherein the enzyme includes a mutation at position 188 and/or position 185 and optionally position 68 of SEQ ID NO:4 or at the corresponding sequence positions of an amino acid sequence with at least 80%, such as, for example, at least such as, for example, 85, 90, 91, 92, 93, 94, 95, 96, 97, 98, 99 or 99.5% sequence identity to SEQ ID NO:4; and/or which includes a C-terminal chain extension by up to 15, 14, 13, 12, 11 or 10 identical or different (proteinogenic) amino acid radicals, in particular by a peptide chain comprising 1 to 10, such as, for example, 3 to 9, basic amino acid radicals, such as lysine, arginine or in particular histidine (such as 3×His, 6×His (SEQ ID NO: 52) or 9×His (SEQ ID NO: 51)); it being possible for the histidine residues to be bonded directly to the C terminus or via a linker group comprising any 1 to 3 amino acid radicals. Examples which may be mentioned are: LEHHH (SEQ ID NO: 53), LEHHHHHH (SEQ ID NO: 50) and LEHHHHHHHHH (SEQ ID NO: 54). Subject matter are furthermore those 3α-HSDHs which additionally to one or more of the above mutations, or as an alternative thereto, include an N-terminal chain extension by up to 25 identical or different amino acid radicals. These are extended by up to 25, 24, 23, 22, 21, 20, 19, 18, 17, 16, 15, 14, 13, 12, 11 or 10 identical or different (proteinogenic) amino acid radicals, in particular by a peptide chain comprising 1 to 10, such as, for example, 3 to 9, basic amino acid radicals, such as lysine, arginine or in particular histidine (such as 3×His, 6×His (SEQ ID NO: 52) or 9×His (SEQ ID NO: 51)); it being possible for the histidine residues to be bonded directly to the N terminus or via a linker group comprising any 1 to 10 amino acid radicals. An example which may be mentioned is: MGSSHHHHHHSSGLVPRGSH— (SEQ ID NO: 55).

6. 3α-HSDH which catalyzes at least the stereospecific enzymatic reduction of a 3-ketosteroid to the corresponding 3-hydroxysteroid and which includes an amino acid sequence which is modified by amino acid mutation in SEQ ID NO:4, the amino acid sequence mutation being selected among single or multiple mutations comprising:

a) P185X$_1$ and/or
b) T188X$_3$
and optionally additionally
c) L68X$_2$
wherein X$_1$ represents a (proteinogenic) amino acid radical which is other than proline (P);
X$_2$ represents a (proteinogenic) amino acid radical which is other than leucine (L);
X$_3$ represents a (proteinogenic) amino acid radical which is other than threonine (T);
d) optionally additionally with C-terminal extension comprising 1 to 10 histidine (H) residues (SEQ ID NO: 56); and/or optionally additionally with N-terminal extension comprising 1 to 10 histidine (H) residues (SEQ ID NO: 56).
wherein the mutated, i.e. modified, amino acid sequence has a sequence identity to SEQ ID NO:4 of 80% to less than 100%, such as, for example, 85, 90, 91, 92, 93, 94, 95, 96, 97, 98, 99 or 99.5% sequence identity.

7. 3α-HSDH as per one of embodiments 5 and 6, selected among
a) the single mutants
P185X$_1$
T188X$_3$
b) the dual mutants
P185X$_1$/T188X$_3$;
L68X$_2$/T188X$_3$;
L68X$_2$/T185X$_1$;
wherein
X$_1$ represents A, T, S, G or V, in particular A;
X$_2$ represents A, G, C, K, S or V, in particular A; and
X$_3$ represents A, G, W, S or V, in particular A or S;
c) optionally additionally with C-terminal extension comprising 1 to 10 histidine residues (SEQ ID NO: 56), it being possible for example for the histidine residues to be bonded directly to the C terminus or via a linker group comprising 1 to 10 amino acid radicals.
and; and/or
d) optionally additionally with N-terminal extension comprising 1 to 10 histidine residues (SEQ ID NO: 56), it being possible for example for the histidine residues to be bonded directly to the N terminus or via a linker group comprising 1 to 10 amino acid radicals.
and
e) mutations as per a) and b), in each case additionally comprising the addition mutation as per c) and/or d), in particular as per c) or d).

Those which must be mentioned in particular are the dual mutants P185X$_1$/T188X$_3$; L68X$_2$/T188X$_3$; L68X$_2$/T185X$_1$; without or with N- or C-terminal extension as defined hereinabove.

Non-limiting examples of suitable mutants are:
single mutants comprising: [T188A], [T188S], [T188G], [T188V], [T188W], [P185A], [P185T], [P185S], [P185G], [P185V], [P185A], dual mutants comprising: [L68A/T188A] and [L68A/T188S], in each case both without His tag and with C-terminal and/or N-terminal His tag.

8. 3α-HSDH as per one of the embodiments 5 to 7 which shows the following property profile in comparison with the native, unmutated 3α-HSDH with SEQ ID NO:4:
d. an increased specific activity (v$_{max}$[U/mg]) for dehydrocholic acid (DHCA) in the enzymatic reduction of DHCA with NADH as cofactor; wherein, for example, the specific activity (U/mg) in the presence of the cofactor NADH in comparison with the unmutated enzyme is increased by at least 1, 5, 10, 50 or 100%, but in particular at least by 1-fold, in particular by 2- to 100-fold or 3- to 20-fold or 5- to 10-fold,
e. a reduced substrate inhibition by DHCA, such as, for example, with Ki values in the range of from >10 mM, such as, for example, at 11 to 200 mM, 12 to 150 mM, 15 to 100 mM,
f. an increased specific activity (v$_{max}$ [U/mg]) for NADH in the enzymatic reduction of DHCA with NADH as cofactor, wherein, for example, the specific activity (U/mg) in the presence of the DHCA in comparison with the unmutated enzyme is increased by at least 1, 5, 10, 50 or 100%, but in particular at least by 1-fold, in particular by 2- to 100-fold or 3- to 20-fold or 5- to 10-fold,
it being possible for these properties a) to c) to be present individually or in any combination, i.e. only a), only b), only c), a) and b), a) and c) or b) and c).

9. Nucleotide sequence which codes for a 3α-HSDH as per one of the preceding embodiments.

Examples which may be mentioned are nucleic acid sequences selected among nucleic acid sequences
a) simultaneously coding for a GDH and a 3α-HSDH mutant as per one of the embodiments 1 to 8 and optionally a 7β-HSDH;
b) coding for a fusion protein comprising a GDH and a 3α-HSDH mutant as per one of the embodiments 1 to 8 and optionally a 7β-HSDH;
where the coding sequences independently of one another may be present singularly or multiply in the construct, such as, for example, in 2, 3, 4, 5, or 6 to 10 copies. Thus, any existing differences in the activity of the individual expression products may be compensated for by choosing the suitable copy number.

10. Expression cassette, comprising at least one nucleotide sequence as per embodiment 9 under the control of at least one regulatory sequence and optionally coding sequences for at least one (such as, for example, 1, 2 or 3) further enzyme, selected among hydroxysteroid dehydrogenases, in particular 7β-HSDH, and dehydrogenases which are suitable for cofactor regeneration, such as, for example, FDH, GDH, ADH, G-6-PDH, PDH. In particular, the enzymes which are present in an expression cassette may utilize different, but preferably identical, pairs of cofactors, such as, for example, the pair of cofactors NAD$^+$/NADH or NADP$^+$/NADPH.

11. Expression vector, comprising at least one expression cassette as per embodiment 10.

12. Recombinant microorganism which bears at least one nucleotide sequence as per embodiment 9 or at least one expression cassette 10 or at least one expression vector as per embodiment 11.

13. Recombinant microorganism as per embodiment 12 which additionally optionally bears the coding sequence for at least one further enzyme, selected among hydroxysteroid dehydrogenases (HSDH) and dehydrogenases which are suitable for cofactor regeneration.

14. Recombinant microorganism as per embodiment 13, the further HSHD being selected among 7β-HSDHs; and the dehydrogenase is selected among NADPH-regenerating enzymes, such as NADPH dehydrogenases, alcohol dehydrogenases (ADH), and NADPH-regenerating formate dehydrogenases (FDH), and also glucose dehydrogenase (GDH), glucose-6-phosphate dehydrogenase (G-6-PDH) or phosphite dehydrogenases (PtDH), or NADH-regenerating enzymes, such as NADH dehydrogenases, NADH-regenerating formate dehydrogenases (FDH), NADH-regenerating alcohol dehydrogenases (ADH), NADH-regenerating glucose-6-phosphate dehydrogenases (G6PDH), NADH-regenerating phosphite dehydrogenases (PtDH) and NADH-regenerating glucose dehydrogenases (GDH).

An example which may be mentioned is a recombinant microorganism which is capable of simultaneously expressing an inventive 3α-HSDH mutant, a herein described GDH and optionally a herein described 7β-HSDH.

Recombinant microorganism which bears the coding sequences for 3α-HSDH mutant, GDH or mutants thereof and 7β-HSDH and one or more (different) expression constructs. Subject-matter of the invention is therefore recombinant microorganisms which are modified (such as, for example, transformed) with a single-plasmid system which bear the coding sequences for 3α-HSDH mutant, GDH or mutants thereof and 7β-HSDH or mutants thereof in one or more copies, such as, for example, 2, 3, 4, 5 or 6 to 10 copies. Subject-matter of the invention is therefore also recombinant microorganisms which are modified (such as, for example, transformed) with a single-plasmid system which bear the coding sequences for 7β-HSDH or mutants thereof, GDH or mutants thereof and 3α-HSDH or mutants thereof in one or more copies such as, for example, in 2, 3, 4, 5 or 6 to 10 copies. The enzymes (7β-HSDH, GDH and 3α-HSDH or their mutants) may, however, also be present in one or more copies on 2 or 3 separate plasmids which are compatible with each other. Suitable basic vectors for the preparation of single-plasmid systems and multicopy plasmids are known to the person skilled in the art. Examples which may be mentioned for a single-plasmid system are, for example, pET21a, and for multicopy plasmids for example the Duet vectors, which are available from Novagen, such as pACYCDuet-1, pETDuet-1, pCDFDuet-1, pRSFDuet-1 and pCOLADuet-1. Such vectors, their compatibility with other vectors and microbial host strains can be found for example in the "User Protocol" TB340 Rev. E0305 from Novagen.

The optimal combination of enzymes for generating plasmid systems may be done by the person skilled in the art without undue burden, taking into consideration the teaching of the present invention. Thus, for example, the person skilled in the art may select, for example as a function of the cofactor specificity of the HSDH enzyme used in each case, the enzyme which is best suited to cofactor regeneration, selected among the abovementioned dehydrogenases, in particular GDH and the respective mutants thereof.

Furthermore, it is possible to distribute the enzymes chosen for the conversion to two or more plasmids, and to prepare, using the plasmids thus prepared, two or more different recombinant microorganisms which are then employed together for the inventive biocatalytic conversion. The respective enzyme combination used for preparing the plasmid may, in this context, in particular also take place with the requirement of a comparable cofactor utilization. Thus, for example, a first microorganism may be modified with a plasmid which bears the coding sequence for a 7β-HSDH or mutant thereof and a GDH. A second microorganism, in contrast, may be modified with a plasmid which bears the coding sequence for a 3α-HSDH or mutant thereof and the coding sequence for a GDH. Both pairs of enzymes may be chosen such that they are capable of regenerating identical pairs of cofactors. Both microorganisms can then be employed simultaneously for the inventive biocatalytic conversion.

The use of two separate biocatalysts (recombinant microorganisms) may have two essential advantages over the use of only one biocatalyst in which all enzymes for the synthesis are expressed:

a) both biocatalysts may be genetically modified and optimized separately from one another. In particular, it is possible to use various cofactor regeneration enzymes, which are optimized either for the regeneration of NADH or a NADPH.
b) It is possible to employ the biocatalysts in differing proportions for the biocatalysis. This allows engaging in the individual reaction rates of the multienzyme process during biocatalysis, even after all the biocatalysts have already been prepared.
15. Recombinant microorganism as per one of embodiments 12 to 14, which is a 7α-HSDH knock-out strain, wherein it the strain, as is described, for example, in WO 2011/147957.
16. Process for the enzymatic or microbial synthesis of 3α-hydroxysteroids, wherein the corresponding 3-ketosteroid is reduced in the presence of a 3α-HSDH as per the definition in one of embodiments 1 to 8 or in the presence of a recombinant microorganism which expresses this 3α-HSDH as per one of embodiments 12 to 15, and optionally at least one formed reduction product is isolated from the reaction mixture.
17. Process as per embodiment 16, wherein the 3-ketosteroid is selected among dehydrocholic acid (DHCA),
the derivatives thereof such as, in particular, a salt, an amide or an alkyl ester of the acid.
18. Process as per embodiment 16 or 17, wherein the reduction takes place in the presence of and in particular with the consumption of NADPH and/or NADH.
19. Process as per embodiment 18, wherein consumed NADPH is regenerated by coupling with an NADPH-regenerating enzyme, wherein the latter is selected in particular among NADPH dehydrogenases, alcohol dehydrogenases (ADH) and NADPH-regenerating formate dehydrogenases (FDH) and an NADPH-regenerating glucose dehydrogenase (GDH), wherein the NADPH-regenerating enzyme is optionally expressed by a recombinant microorganism; and/or where consumed NADH is regenerated by coupling with an NADH-regenerating enzyme, wherein the latter is selected in particular among NADH-dehydrogenases, NADH-regenerating formate dehydrogenases (FDH), NADH-regenerating alcohol dehydrogenases (ADH), NADH-regenerating glucose-6-phosphate dehydrogenases (G6PDH), NADH-regenerating phosphite dehydrogenases (PtDH) and NADH-regenerating glucose dehydrogenases (GDH), wherein the NADH-regenerating enzyme is optionally expressed in a recombinant microorganism.
20. Process as per embodiment 19, wherein the NADPH-regenerating enzyme is selected among
g. FDHs, including mutants of a NAD$^+$-dependent FDH that catalyzes at least the enzymatic oxidation of formic acid to $CO_2$, wherein the mutant in comparison with the unmutated enzyme additionally accepts NADP$^+$ as cofactor; and
h. GDHs.
21. Process for the preparation of ursodeoxycholic acid (UDCA) of the formula (1)

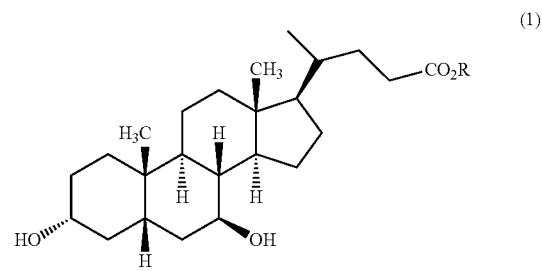

(1)

in which
R represents alkyl, H, an alkali metal ion or $N(R^3)_4^+$, wherein the radicals $R^3$ are identical or different and represent H or alkyl, or the group —$CO_2R$ is replaced by the acid amide group —$CONR^1R^2$, wherein $R^1$ and $R^2$ independently of one another represent an alkyl radical;
in which
a) optionally a cholic acid (CA) of the formula (2)

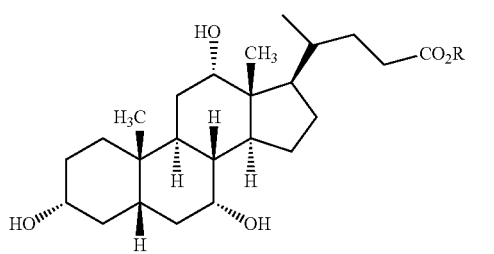

(2)

in which R has the abovementioned meanings or the group —$CO_2R$ is replaced by the acid amide group —$CONR^1R^2$ as defined hereinabove
is oxidized chemically to dehydrocholic acid (DHCA) of the formula (3)

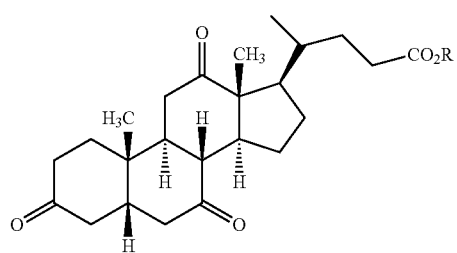

(3)

in which R has the abovementioned meanings or the group —$CO_2R$ is replaced by the acid amide group —$CONR^1R^2$ as defined hereinabove;
b) DHCA is reduced in the presence of at least one 3α-HSDH mutant as per the definition in one of claims 1 to 8 (being present as the isolated enzyme or expressed by a corresponding recombinant microorganism) and in the presence of at least one 7β-HSDH (being present as the isolated enzyme or expressed by a corresponding recombinant microorganism) to the corresponding 12-keto-ursodeoxycholic acid (12-keto UDCA) of the formula (5)

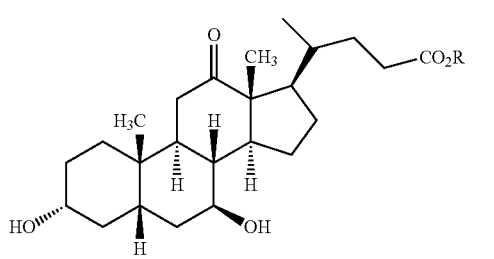

(5)

in which R has the abovementioned meanings or the group —$CO_2R$ is replaced by the acid amide group —$CONR^1R^2$ as defined hereinabove, in particular in the presence and with the consumption of NADH and/or NADPH, and subsequently
c) 12-keto-UDCA of the formula (5) is reduced chemically to UDCA; and
d) optionally, the reaction product is purified further.
22. Process as per embodiment 21, wherein at least step b) is carried out in the presence of a recombinant microorganism as per one of embodiments 12 to 15.
23. Process as per embodiment 21 or 22, wherein step b) is coupled with identical or different cofactor regeneration systems.
24. Process for the preparation of UDCA of the formula (1)

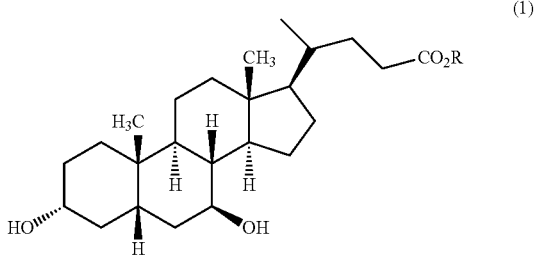

(1)

in which
R represents alkyl, H, an alkali metal ion or $N(R^3)_4^+$, wherein the radicals $R^3$ are identical or different and represent H or alkyl, or the group —$CO_2R$ is replaced by the acid amide group —$CONR^1R^2$, as defined hereinabove
in which
a) optionally a CA of the formula (2)

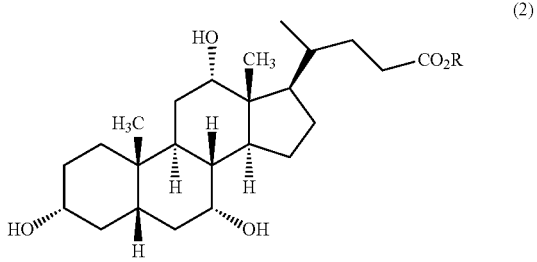

(2)

in which R has the abovementioned meanings or the group —$CO_2R$ is replaced by the acid amide group —$CONR^1R^2$ as defined hereinabove is oxidized chemically to DHCA of the formula (3)

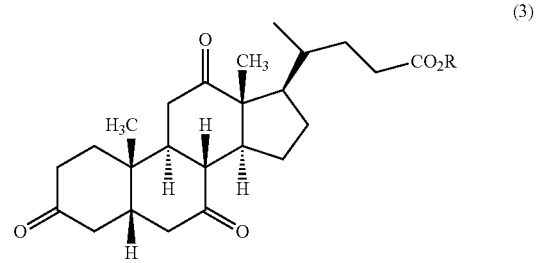

(3)

in which R has the abovementioned meanings or the group —$CO_2R$ is replaced by the acid amide group —$CONR^1R^2$ as defined hereinabove;

b) DHCA is reduced in the presence of at least one 7β-HSDH and in the presence of at least one 3α-HSDH to the corresponding 12-keto UDCA of the formula (5)

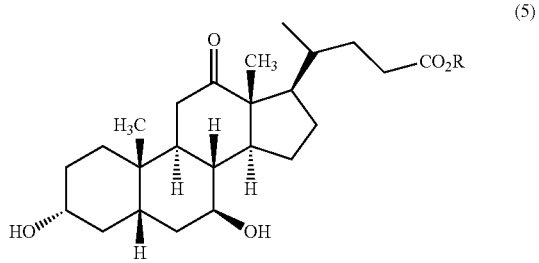

(5)

in which R has the abovementioned meanings or the group —CO$_2$R is replaced by the acid amide group —CONR$^1$R$^2$ as defined hereinabove, in particular in the presence and with the consumption of NADH and/or NADPH, and subsequently
c) 12-keto-UDCA of the formula (5) is reduced chemically to UDCA; and
d) optionally, the reaction product is purified further;
wherein the conversions of step b) are carried out in the presence of a recombinant microorganism as per one of embodiments 12 to 15, such as, for example, in the presence of whole cells of one or more different recombinant microorganisms as per one of embodiments 12 to 15, wherein the microorganism(s) includes the enzymes required for the conversion and the cofactor regeneration in a manner described herein in greater detail.
In this context, process step b) can be configured in different ways. Either both enzymes (7β-HSDH mutant and 3α-HSDH) may be present at the same time (for example one-top reaction with both isolated enzymes, or one or more corresponding recombinant microorganisms which express both enzymes are present), or the partial reactions may proceed in any desired order (first the 7β-HSDH mutant-catalyzed reduction and then the 3α-HSDH-catalyzed reduction; or first the 3α-HSDH-catalyzed reduction and then the 7β-HSDH mutant-catalyzed reduction).
Step b) may furthermore be coupled with a cofactor regeneration system in which NADPH is regenerated by an NADPH regenerating GDH with consumption of glucose, or is coupled with a cofactor regeneration system in which consumed NADH is regenerated by an NADH-regenerating GDH, ADH or FDH.
25. Bioreactor for carrying out a process as per one of embodiments 16 to 24, in particular comprising at least one of the enzymes 7β-HSDH, FDH and/or 3α-HSDH or their mutants; or 7β-HSDH, GDH and/or 3α-HSDH or their mutants.
The present invention is not limited to the concrete embodiments described herein. Rather, the teaching of the present invention allows a person skilled in the art to provide further developments of the invention without undue burden. Thus, for example, he may generate further enzyme mutants in a targeted manner and screen and optimize them for the desired property profile (improved cofactor dependency and/or stability, reduced substrate inhibition); or he may isolate further suitable wild-type enzymes (7β- and 3α-HSDHs, FDHs, GDHs ADHs etc.) and use them in accordance with the invention. Furthermore, he may, for example depending on the property profile (in particular cofactor dependency) of the HSDHs used, such as, in particular, 7β-HSDH and 3α-HSDH or mutants thereof, select suitable dehydrogenases which can be used for cofactor regeneration (GDH, FHD, ADH and the like) and mutants thereof, and distribute the selected enzymes to one or more expression constructs or vectors and thus, if required, generate one or more recombinant microorganisms which then make possible an optimized preparation process based on whole cells.

Further Developments of the Invention

1. General Definitions, and Abbreviations Used

Unless otherwise specified, the term "7β-HSDH" refers to a dehydrogenase enzyme which catalyzes at least the stereospecific and/or regiospecific reduction of DHCA or 7,12-diketo-3α-CA (7,12-diketo-LCA) to obtain 3,12-diketo-7β-CA or 12-keto-UDCA, in particular with the stoichiometric consumption of NADPH, and optionally the corresponding reverse reaction. In this context, the enzyme may be a native or a recombinantly produced enzyme. The enzyme may, in principle, be present as a mixture with cellular contaminants, such as, for example, protein contaminants, but preferably be present in pure form. Suitable detection methods are described, for example, in the experimental part which follows or are known from the literature (for example *Characterization of NADP-dependent 7 beta-hydroxysteroid dehydrogenases from Peptostreptococcus productus and Eubacterium aerofaciens*. S Hirano and N Masuda. Appl Environ Microbiol. 1982). Enzymes of this activity are classified under EC number 1.1.1.201. Suitable enzymes can be isolated for example from *Colinsellea aerofaciens*.

Unless otherwise specified, the term "3α-HSDH" refers to a dehydrogenase enzyme which catalyzes at least the stereospecific and/or regiospecific reduction of 3,12-diketo-7β-CA or DHCA to 12-keto-UDCA or 7,12-diketo-3α-CA (7,12-diketo-LCA), in particular with the stoichiometric consumption of NADH and/or NADPH, and optionally the corresponding reverse reaction. Suitable detection methods are described, for example, in the experimental part herein below or are known from the literature. Suitable enzymes are obtainable for example from *Comanomonas testosteroni* (i.e. *Comamonas testosteroni*) (e.g. ATCC11996). An NADPH-dependent 3α-HSDH is known for example from rodents and can likewise be employed (Cloning and sequencing of the cDNA for rat liver 3 alphahydroxysteroid/dihydrodiol dehydrogenase, J E Pawlowski, M Huizinga and T M Penning, May 15, 1991 The Journal of Biological Chemistry, 266, 8820-8825). Enzymes of this activity are classified under EC number 1.1.1.50.

Unless otherwise specified, the term "GDH" refers to a dehydrogenase enzyme which catalyzes at least the oxidation of β-D-glucose to D-glucono-1,5-lactone with the stoichiometric consumption of NAD$^+$ and/or NADP$^+$ and optionally the corresponding reverse reaction. Suitable enzymes can be obtained for example from *Bacillus subtilis* or *Bacillus megaterium*. Enzymes of this activity are classified under EC number 1.1.1.47.

Unless otherwise specified, the term "FDH" refers to a dehydrogenase enzyme which catalyzes at least the oxidation of formic acid (or corresponding formate salts) to carbon dioxide with the stoichiometric consumption of NAD$^+$ and/or NADP$^+$, and optionally the corresponding reverse reaction. Suitable detection methods are described, for example, in the experimental part herein below or from the literature. Suitable enzymes can be obtained for example from *Candida boidinii*, *Pseudomonas* sp or *Mycobacterium vaccae*. Enzymes with this activity are classified under EC number 1.2.1.2.

According to the invention, a "pure form" or a "pure" or "essentially pure" enzyme is understood according to the invention to be an enzyme with a degree of purity of more than 80, preferably more than 90, in particular more than 95 and especially more than 99% by weight, based on the total protein content, determined with the aid of customary protein detection methods such as, for example, the Biuret method or the protein detection as described by Lowry et al. (cf. description in R. K. Scopes, Protein Purification, Springer Verlag, New York, Heidelberg, Berlin (1982)).

A "redox equivalent" is understood as meaning a low-molecular-weight organic compound which can be used as an electron donor and/or electron acceptor, such as, for example, nicotinamide derivates such as $NAD^+$ and $NADH^+$, and their reduced forms NADH and NADPH, respectively. In the context of the present invention, "redox equivalent" and "cofactor" are used synonymously. For the purposes of the invention, therefore, a "cofactor" may also be paraphrased as a "redox-capable cofactor", that is to say a cofactor which may be present in reduced and in oxidized form.

A "consumed" cofactor is understood as meaning the reduced or oxidized form of the cofactor which, in the course of a given reduction or oxidation reaction of a substrate, is converted into the corresponding oxidized or reduced form, respectively. Regeneration returns the oxidized or reduced cofactor formed during the reaction into its reduced or oxidized initial form, respectively, so that it is again available for the conversion of the substrate.

According to the present invention, an "altered cofactor utilization" is understood as meaning a qualitative or quantitative alteration in comparison with a reference. In particular, an altered cofactor utilization can be observed by carrying out amino acid sequence mutations. This alteration can then be discerned in comparison with the unmutated starting enzyme. Here, the activity relative to a certain cofactor may be increased or reduced by carrying out a mutation, or completely prevented. An altered cofactor utilization, however, also comprises alterations such that, instead of a specificity for a single cofactor, at least one further, second cofactor which is different from the first cofactor can now be utilized (i.e. extended cofactor utilization exists). Conversely, however, an ability, originally present, of utilizing two different cofactors may be altered such that specificity is increased for one of these cofactors only, or reduced or completely eliminated for one of these cofactors only.

Thus, for example, an enzyme which is dependent on cofactor NAD (NADH) may, owing to an alteration of the cofactor utilization, now be dependent on both NAD (NADH) and on the cofactor NADP (NADPH), or the original dependency of NAD (NADH) may fully be converted into a dependency of NADP (NADPH), and vice versa.

Unless otherwise specified, the expressions "$NAD^+$/NADH dependency" or "$NADP^+$/NADPH dependency" should be interpreted broadly in accordance with the invention. These expressions comprise not only a "specific" dependencies, i.e. exclusively dependency on $NAD^+$/NADH and/or $NADP^+$/NADPH, but also the dependency of the enzymes used in accordance with the invention on both cofactors, i.e. dependency of $NAD^+$/NADH and $NADP^+$/NADPH.

The same applies to the expressions used "$NAD^+$/NADH-accepting" and/or "$NADP^+$/NADPH-accepting".

Unless otherwise specified, the expressions "$NAD^+$/NADH regenerating" or "$NADP^+$/NADPH regenerating" should be interpreted broadly in accordance with the invention. For these expressions comprise not only "specific", i.e. exclusive ability of regenerating consumed cofactor $NAD^+$/NADH and/or $NADP^+$/NADPH, but also the ability of regenerating both cofactors, i.e. $NAD^+$/NADH and $NADP^+$/NADPH.

"Proteinogenic" amino acids comprise in particular (one-letter code): G, A, V, L, I, F, P, M, W, S, T, C, Y, N, Q, D, E, K, R and H.

According to the invention, an "immobilization" is understood as meaning the covalent or noncovalent bonding of a biocatalyst used in accordance with the invention, such as, for example, a 7β-HSDH, to a solid support material, i.e. a support material which is essentially insoluble in the surrounding liquid medium. According to the invention, whole cells, such as the recombinant microorganisms which are used in accordance with the invention, may also be immobilized with the aid of such supports.

A "substrate inhibition which is reduced in comparison with the unmutated enzymes" means that the substrate inhibition observed in the unmutated enzyme for a particular substrate can no longer be observed, i.e. is essentially no longer capable of being measured or commences only at a higher substrate concentration, i.e. the $K_i$ value is increased. N- or C-terminal extensions according to the invention comprise approximately 15 to 25 proteinogenic amino acid radicals which are attached to a terminal amino acid radical, optionally reversibly, for example via a protease cleavage site. Preferred residues comprise so-called "His tags" which are known per se, with, for example, 3, 6 (SEQ ID NO: 52) or 9 consecutive histidine residues (SEQ ID NO: 51) in the extension sequence.

According to the invention, a "cholic acid compound" is understood as meaning compounds with the carbon skeleton, in particular the steroid structure, of cholic acid, and the presence of keto and/or hydroxyl and/or acyloxy groups at ring position 7 and optionally positions 3 and/or 12.

A compound of a specific type such as, for example, a "cholic acid compound" or an "ursodeoxycholic acid compound" is, in particular, also understood as meaning derivatives of the underlying starting compound (such as, for example, cholic acid or ursodeoxycholic acid).

Such derivatives comprise "salts" such as, for example, alkali metal salts, such as lithium, sodium and potassium salts of the compounds; and ammonium salts, where under an ammonium salt is comprised the $NH_4^+$ salt or those ammonium salts in which at least one hydrogen atom can be replaced by a $C_1$-$C_6$ alkyl radical. Typical alkyl radicals are, in particular $C_1$-$C_4$-alkyl radicals, such as methyl, ethyl, n- or i-propyl-, n-, sec- or tert-butyl, and n-pentyl and n-hexyl, and their analogs with one or more branches.

"Alkyl esters" of compounds according to the invention are, in particular, lower alkyl esters such as, for example, $C_1$-$C_6$-alkyl esters. Non-limiting examples which may be mentioned are methyl, ethyl, n- or i-propyl-, n-, sec- or tert-butyl esters, or longer chain esters such as, for example, n-pentyl and n-hexyl esters, and their analogs with one or more branches.

"Amides" are, in particular, reaction products of acids according to the invention with ammonia or with primary or secondary monoamides. Such amides are, for example, mono- or di-$C_1$-$C_6$-alkyl monoamines, it being possible for the alkyl radicals independently of one another optionally to be substituted further such as, for example, by carboxyl, hydroxyl, halogen (such as F, Cl, Br, I), nitro and sulfonate groups.

"Acyl groups" according to the invention are, in particular, nonaromatic groups with 2 to 4 carbon atoms such as, for example, acetyl, propyonyl and butyryl, and aromatic groups with an optionally substituted mononuclear aromatic ring, suitable substitutents being selected for example among hydroxyl, halogen (such as F, Cl, Br, I), nitro and $C_1$-$C_6$-alkyl groups such as, for example, benzoyl or toluoyl.

The hydroxysteroid compounds applied and/or produced in accordance with the invention such as, for example, cholic acid, ursodeoxycholic acid, 12-keto-chenodeoxycholic acid, chenodeoxycholic acid and 7-keto-lithocholic acid, can be employed in the presence according to the invention, or obtained therefrom, in stereoisomerically pure form or in a mixture with other stereoisomers. Preferably, however, the compounds applied and/or produced are employed and/or isolated in essentially stereoisomerically pure form.

The structural formulae, their chemical names and the abbreviations of essential chemical compounds are tabulated in the table herein below:

| Formula | Abbreviation | Chemical name |
|---|---|---|
| Cholic acid | CA | Cholic acid |
| dehydrocholic acid | DHCA | dehydrocholic acid |
| 3,12-diketo-7β-cholanic acid | 3,12-diketo-7β-CA | 3,12-diketo-7β-cholanic acid |

-continued

| Formula | Abbreviation | Chemical name |
|---|---|---|
| [structure of 12-keto-ursodeoxycholic acid] | 12-keto-UDCA | 12-keto-ursodeoxycholic acid |
| 12-keto-ursodeoxycholic acid | | |
| [structure of ursodeoxycholic acid] | UDCA | Ursodeoxycholic acid |
| Ursodeoxycholic acid | | |
| [structure of cholic acid methyl ester] | CA methyl ester | Cholic acid methyl ester |
| Cholic acid methyl ester | | |
| [structure of 3,7-diacetylcholic acid methyl ester] | 3,7-diacetyl-CA methyl ester | 3,7-diacetylcholic acid methyl ester* |
| 3,7-diacetylcholic acid methyl ester | | |

-continued
| Formula | Abbreviation | Chemical name |
|---|---|---|
| 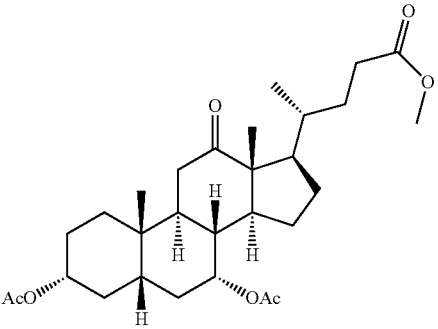<br>12-keto-3,7-diacetyl-cholanic acid methyl ester | 12-keto-3,7-diacetyl-CA methyl ester | 12-keto-3,7-diacetyl-cholanic acid methyl ester* |
| 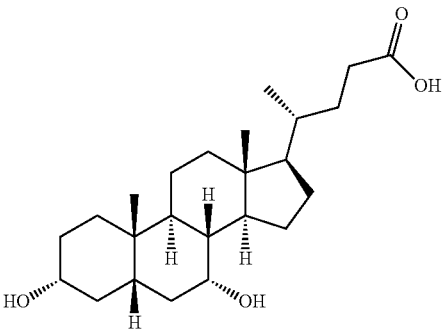<br>Chenodeoxycholic acid | CDCA | Chenodeoxycholic acid |
| 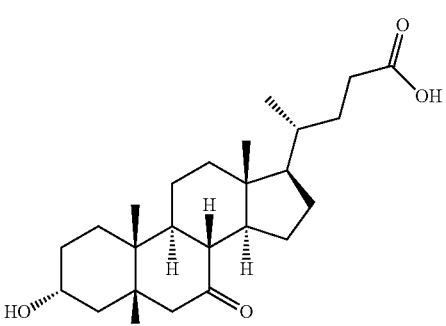<br>7-keto-lithocholic acid | 7-keto-LCA | 7-keto-lithocholic acid |
| 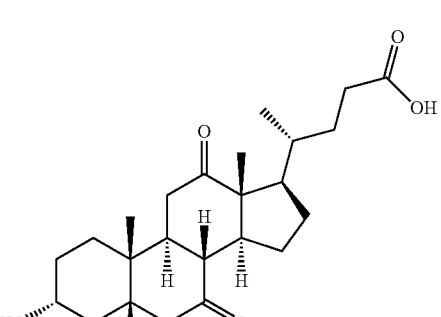<br>7,12-diketo-lithocholic acid | 7,12-diketo-LCA | 7,12-diketo-lithocholic acid |

| Formula | Abbreviation | Chemical name |
|---|---|---|
| 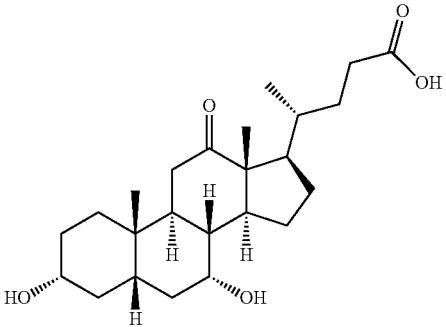12-keto-chenodeoxycholic acid | 12-keto-CDCA | 12-keto-chenodeoxycholic acid |

2. Proteins

The present invention is not restricted to the specifically disclosed proteins or enzymes with 7β-HSDH, FDH, GDH or 3α-HSDH activity and/or their mutants, but, rather, it also extends to functional equivalents thereof.

For the purposes of the present invention "functional equivalents" or analogs of the specifically disclosed enzymes are polypeptides which differ from the former and which still retain the desired biological activity such as, for example, 7βHSDH activity.

Thus, for example, the expression "functional equivalents" is understood as meaning enzymes which, in the 7β-HSDH, FDH, GDH or 3α-HSDH activity test used, have an activity which is by at least 1%, such as, for example, at least 10% or 20%, such as, for example, at least 50% or 75% or 90% higher or lower than that of a starting enzyme comprising an amino acid sequence defined herein.

Functional equivalents are furthermore stable preferably between pH 4 to 11 and advantageously have a pH optimum in a range of from pH 6 to 10, such as, in particular, 8.5 to 9.5, and a temperature optimum in the range of from 15° C. to 80° C. or 20° C. to 70° C., such as, for example, approximately 45 to 60° C. or approximately 50 to 55° C.

The 7β-HSDH activity may be detected with the aid of various known tests. Without being limited thereto, a test may be mentioned in which a reference substrate, such as, for example, CA or DHCA, is used under standardized conditions as defined in the experimental part.

Tests for determining the FDH, GDH, 7β-HSDH or 3α-HSDH activity are likewise known per se.
The expression "functional equivalents" is, according to the invention, in particular also to be understood as meaning "mutants" which, while having an amino acid in at least one sequence position of the abovementioned amino acid sequences which is different to the amino acid which has been mentioned specifically, retain one of the abovementioned biological activities. Therefore, "functional equivalents" comprise the mutants obtainable by one or more, such as, for example, 1, 2, 3, 4, 5, 6, 7, 8, 9, 10, 11, 12, 13, 14 or 15 amino acid additions, substitutions, deletions and/or inversions, it being possible for the abovementioned modifications to occur in any sequence position as long as they result in a mutant with the property profile according to the invention. Functional equivalents exists in particular also when the reactivity patterns of the mutant and the unmodified polypeptide agree in qualitative terms, i.e. when, for example, the same substrates are converted at different rates. Examples of suitable amino acid substitutions are compiled in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In "functional equivalents" in the above sense are also "precursors" of the above-described polypeptides and "functional derivatives" and "salts" of the polypeptides.

In this context, "precursors" are natural or synthetic precursors of the polypeptides with or without the desired biological activity.

The expression "salts" is understood as meaning not only salts of carboxyl groups, but also acid addition salts of amino groups of the protein molecules according to the invention. Salts of carboxyl groups can be prepared in a manner known per se and comprise inorganic salts such as, for example, sodium, calcium, ammonium, iron and zinc salts, and salts with organic bases such as, for example, amides, such as triethanolamine, arginine, lysine, piperidine and the like. Acid addition salts such as, for example, salts with mineral acids, such as hydrochloric acid or sulfuric acid, and salts with organic acids, such as acetic acid and oxalic acid, are likewise subject matter of the invention.

In "functional derivatives" of polypeptides according to the invention can also be generated at functional amino acid side-groups or at their N- or C-terminal end, using known techniques. Such derivatives comprise, for example, aliphatic esters of carboxyl groups, amides of carboxyl groups, obtainable by reaction with ammonia or with a primary or secondary amine; N-acyl derivates of free amino groups, prepared by reaction with acyl groups; or O-acyl derivatives free hydroxyl groups, prepared by reaction with acyl groups.

Naturally, "functional equivalents" also comprise polypeptides which are available from other organisms, and naturally occurring variants. For example, sequence comparisons may be used to determine regions of homologous sequence regions, and equivalent enzymes can be established on the basis of the specific requirements of the invention.

"Functional equivalents" likewise comprise fragments, preferably individual domains or sequence motifs, of the polypeptides according to the invention which have, for example, the desired biological function.

"Functional equivalents" are furthermore fusion proteins which have one of the abovementioned polypeptide sequences or functional equivalents derived therefrom and at least one other heterologous sequence functionally different therefrom in functional N- or C-terminal linkage (i.e. without significant mutual impairment of the functions of parts of the fusion proteins). Non-limiting examples of such heterologous sequences are, for example, signal peptides, histidine anchors or enzymes.

"Functional equivalents" include in accordance with the invention homologs of the specifically disclosed proteins. These have at least 60%, preferably at least 75%, in particular at least 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A percentage homology or identity of a homologous polypeptide according to the invention means in particular percentage identity of the amino acid radicals based on the total length of one of the amino acid sequences which are described specifically herein.

The percentage identity data may also be determined by using BLAST alignments, the algorithm blastp (protein-protein BLAST), or by employing the Clustal settings specified herein below.

In the event of possible protein glycosylation, "functional equivalents" according to the invention encompass proteins of the above-specified type in deglycosylated or glycosylated form, and modified forms obtainable by changing the glycosylation pattern.

Homologs of the proteins or polypeptides according to the invention can be generated by mutagenesis, for example by point mutation, or by extension or truncation of the protein.

Homologs of the proteins according to the invention can be identified by screening combinatorial libraries of mutants such as, for example, truncation mutants. For example, it is possible to generate a variegated library of protein variants by combinatorial mutagenesis at the nucleic acid level, such as, for example, by enzymatic ligation of a mixture of synthetic oligonucleotides. There exists a large number of processes which can be used to generate libraries of potential homologs from a degenerate oligonucleotide sequence. The chemical synthesis of a degenerate gene sequence may be carried out in an automatic DNA synthesizer, and the synthetic gene may then be ligated to a suitable expression vector. The use of a degenerate set of genes makes it possible to provide, in one mixture, all sequences which code for the desired set of potential protein sequences. Methods for synthesizing degenerate oligonucleotides are known to the person skilled in the art (for example Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

The prior art knows a variety of techniques for screening gene products of combinatorial libraries which have been generated by point mutations or truncation, and for screening cDNA libraries for gene products with a selected characteristic. These techniques can be adapted to the rapid screening of the gene libraries which have been generated by combinatorial mutagenesis of homologs according to the invention. The most frequently used techniques for screening large gene libraries undergoing high-throughput analysis comprise the cloning of the gene library into replicable expression vectors, transforming suitable cells with the resulting vector library and expressing the combinatorial genes under conditions under which the detection of the desired activity facilitates isolation of the vector which codes for the gene whose product has been detected. Recursive ensemble mutagenesis (REM), a technique which increases the frequency of functional mutants in the libraries, can be used in combination with the screening tests in order to identify homologs (Arkin and Yourvan (1992) PNAS 89:7811-7815; Delgrave et al. (1993) Protein Engineering 6(3):327-331).

The invention furthermore comprises the use of the 7β-HSDH wild type from *Collinsella aerofaciens* ATCC 25986 as is described in the applicant's WO 2011/064404, which is herewith expressly referred to.

This 7β-HSDH, which is obtainable from *Collinsella aerofaciens* DSM 3979, is characterized in particular by at least one further of the following properties, such as, for example, by 2, 3, 4, 5, 6 or 7 or all of such properties:

a) molecular weight (SDS gel electrophoresis): approximately 28-32 kDa, in particular approximately 29 to 31 kDa or approximately 30 kDa;

b) molecular weight (gel filtration under non-denaturing conditions, such as, in particular, without SDS): approximately 53 to 60 kDa, in particular approximately 55 to 57 kDa, such as 56.1 kDa. This confirms the dimeric nature of the *Collinsella aerofaciens* DSM 3979 7β-HSDH;

c) stereoselective reduction of the 7-carbonyl group of 7-keto-LCA to a 7β-hydroxy group;

d) pH optimum for the oxidation of UDCA in the range of from pH 8.5 to 10.5, in particular 9 to 10;

e) pH optimum for the reduction of DHCA and 7-keto-LCA in the range of from pH 3.5 to 6.5, in particular pH 4 to 6;

f) at least one kinetic parameter from the following table for at least one of the substrates/cofactors mentioned therein; in the range of from ±20%, in particular ±10%, ±5%, ±3%±2% or ±1% around the value mentioned in each case specifically in the table which follows.

|   | $K_M$ (μM) | $V_{max}$ (U/mg Protein)[b] | $k_{cat}$ (1 μmol/(μmol × min)) |
|---|---|---|---|
| NADP+ | 5.32 | 30.58 | 944.95 |
| NADPH | 4.50 | 33.44 | 1033.44 |
| UDCA | 6.23 | 38.17 | 1179.39 |
| 7-Keto-LCA | 5.20 | 30.77 | 950.77 |
| DHCA | 9.23 | 28.33 | 875.35 |
| NAD+ | —[a] | — | Traces |
| NADH | — | — | Traces |

[a] no determination possible owing to the very low activity
[b] 1 U = 1 μmol/min g) Phylogenetic sequence relationship of the prokaryotic *Collinsella aerofaciens* DSM 3979 7β-HSDH with the animal 11β-HSDH subgroup, comprising *Cavia porcellus*, *Homo sapiens* and *Mus musulus*.

For example, this 7β-HSDH displays the following properties or combinations of properties: a); b); a) and b); a) and/or b) and c); a) and/or b) and c) and d); a) and/or b) and c) and d) and e); a) and/or b) and c) and d) and e) and f).

Such a 7β-HSDH or functional equivalent derived therefrom is furthermore characterized by
i. the stereospecific reduction of a 7-ketosteroid to the corresponding 7β-hydroxysteroid, and/or
j. the regiospecific hydroxylation of a ketosteroid comprising a keto group in the 7-position and at least one further keto group on the steroid skeleton to give the corresponding 7β-hydroxysteroid, such as, in particular, of dehydrocholic acid (DHCA) in the 7-position to give the corresponding 3,12-diketo-7β-cholanic acid, catalyzes, and is for example NADPH-dependent.

Such a 7β-HSDH has, in particular, an amino acid sequence as per SEQ ID NO:2 (Accession NO: ZP_01773061) or a sequence derived therefrom with a degree of identity of at least 60%, such as, for example, 65, 70, 75, 80, 85 or 90, such as, for example, at least 91, 92, 93, 94, 95, 96, 97, 98, 99 or 99.5% to this sequence; optionally additionally characterized by one of the following properties or combinations of properties; a); b); a) and b); a) and/or b) and c); a) and/or b) and c) and d); a) and/or b) and c) and d) and e); a) and/or b) and c) and d) and e) and f) as per the above definition.

3. Nucleic Acids and Constructs 3. 1 Nucleic Acids

Subject-matter of the invention is also nucleic acid sequences which code for an enzyme with 7β-HSDH, FDH, GDH and/or 3α-HSDH activity and their mutants.

The present invention also relates to nucleic acids with a certain degree of identity to the specific sequences described herein.

The "identity" between two nucleic acids is understood as meaning the identity of the nucleotides over in each case the entire length of the nucleic acid, in particular the identity which is calculated by comparison with the aid of the Vector NTI Suite 7.1 software from Informax (USA) by applying the Clustal method (Higgins D G, Sharp P M. Fast and sensitive multiple sequence alignments on a microcomputer. Comput Appl. Biosci. 1989 April; 5(2):151-1), with the following parameter settings:
Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |

-continued

| | |
|---|---|
| FAST algorithm | on |
| Window size | 5 |
| Number of best diagonals | 5 |

Alternatively, the identity may also be determined by the method of Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, which can be found on the internet, using the following parameters:

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences (single- and double-stranded DNA and RNA sequences such as, for example, cDNA and mRNA) mentioned herein can be generated in a manner known per se by chemical synthesis starting from the nucleotide units such as, for example, by fragment condensation of individual overlapping, complementary nucleic acid units of the double helix. Oligonucleotides may be synthesized chemically for example in a known manner, following the phosphoamidite method (Voet, Voet, $2^{nd}$ edition, Wiley Press New York, pages 896-897). The assembly of synthetic oligonucleotides and the filling-in of gaps with the aid of the DNA polymerase Klenow fragment and with the aid of ligation reactions and general cloning methods are described by Sambrook et al. (1989), Molecular Cloning: A laboratory manual, Cold Spring Harbor Laboratory Press.

Subject-matter of the invention is also nucleic acid sequences (single- and double-stranded DNA and RNA sequences, such as, for example, cDNA and mRNA) which code for any of the above polypeptides at their functional equivalents which may be prepared for example using artificial nucleotide analogs.

The invention relates both to isolated nucleic acid molecules which code for polypeptides or proteins according to the invention or biologically active sections thereof, and to nucleic acid fragments which may be used for example for use as hybridization probes or primers for identifying or amplifying coding nucleic acids according to the invention.

The nucleic acid molecules according to the invention may additionally comprise untranslated sequences from the 3' and/or 5' end of the coding gene region.

The invention furthermore comprises the nucleic acid molecules which are complementary to the specifically described nucleotide sequences or to a section thereof.

The nucleotide sequences according to the invention make possible the generation of probes and primers which may be used for identifying and/or cloning homologous sequences in other cell types and other organisms. Such probes or primers usually comprise a nucleotide sequence region which, under "stringent" conditions (see herein below), hybridizes to at least approximately 12, preferably at least approximately 25, such as, for example, approximately 40, 50 or 75 consecutive nucleotides of a sense strand of a nucleic acid sequence according to the invention or of a corresponding antisense strand.

An "isolated" nucleic acid molecule is separated from other nucleic acid molecules which are present in the natural source of the nucleic acid and may additionally be essentially free of other cellular material or culture medium if it is generated by recombinant techniques, or free from chemical precursors or other chemicals if it is synthesized chemically.

A nucleic acid molecule according to the invention may be isolated by means of standard techniques of molecular biology and the sequence information provided in accordance with the invention. For example, cDNA may be isolated from a suitable cDNA library by using one of the specifically disclosed complete sequences or a section thereof as hybridization probe and using standard hybridization techniques (as described, for example, in Sambrook, J., Fritsch, E. F. and Maniatis, T. Molecular Cloning: A Laboratory Manual. $2^{nd}$ Edition, Cold Spring Harbor Laboratory, Cold Spring Harbor Laboratory Press, Cold Spring Harbor, N.Y., 1989). Moreover, a nucleic acid molecule comprising any of the disclosed sequences or a section thereof may be isolated by polymerase chain reaction, using the oligonucleotide primers which have been constructed on the basis of this sequence. The nucleic acid amplified in this manner may be cloned into a suitable vector and characterized by DNA sequence analysis. Furthermore, the oligonucleotides according to the invention may be generated by standard synthesis methods, for example using an automatic DNA synthesizer.

Nucleic acid sequences according to the invention or derivatives thereof, homologs or parts of these sequences may be isolated from other bacteria for example using customary hybridization methods or the PCR technique, for example by way of genomic libraries or cDNA libraries. These DNA sequences hybridize with the sequences according to the invention under standard conditions.

"Hybridizing" is understood as meaning the ability of a polynucleotide or oligonucleotide to bind, under standard conditions, to an almost complementary sequence, while unspecific bindings between non-complementary partners will not take place under these conditions. In this context, the sequences may be 90-100% complementary. The property of complementary sequences of being able to specifically bind to each other is exploited for example in the Northern or Southern blot technique or in the primer binding in PCR or RT-PCR.

For the hybridization, use is advantageously made of short oligonucleotides of the conserved regions. However, it is also possible to use longer fragments of the nucleic acids according to the invention, or the complete sequences, for the hybridization. Depending on the nucleic acid employed (oligonucleotide, longer fragment or complete sequence) or depending on which nucleic acid type, DNA or RNA, is used for the hybridization, these standard conditions will vary. Thus, for example, the melting temperatures for DNA:DNA hybrids are approximately 10° C. lower than those of DNA:RNA hybrids of the same length.

Depending on the nucleic acid, standard conditions are understood as meaning, for example, temperatures of between 42 and 58° C. in an aqueous buffer solution having a concentration of between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids, the hybridization conditions are advantageously 0.1×SSC and temperatures of between about 30° C. to 55° C., preferably between about 45° C. to 55° C. These temperatures stated for the hybridization are melting temperature values which have been calculated by way of example for a nucleic acid having a length of approximately 100 nucleotides and a G+C content of 50% in the absence of formamide. The experimental conditions for the DNA hybridization are described in specialist textbooks of genetics, such as, for example, Sambrook et al., "Molecular Cloning", Cold Spring Harbor Laboratory, 1989, and may be calculated using formulae known to the person skilled in the art, for example as a function of the length of the nucleic acids, the type of hybrids or the G+C content. The person skilled in the art may obtain further information with regard to hybridization from the following textbooks: Ausubel et al. (eds.), 1985, Current Protocols in Molecular Biology, John Wiley & Sons, New York; Hames and Higgins (eds.), 1985, Nucleic Acids Hybridization: A Practical Approach, IRL Press at Oxford University Press, Oxford; Brown (ed.), 1991, Essential Molecular Biology: A Practical Approach, IRL Press at Oxford University Press, Oxford.

The "hybridization" may take place in particular under stringent conditions. Such hybridization conditions are described for example in Sambrook, J., Fritsch, E. F., Maniatis, T., in: Molecular Cloning (A Laboratory Manual), 2nd Edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are understood as meaning in particular the following: incubation overnight at 42° C. in a solution composed of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured sheared salmon sperm DNA, followed by a wash step of the filters with 0.1×SSC at 65° C.

Subject matter of the invention are also derivatives of the specifically disclosed or derivable nucleic acid sequences.

Thus, further nucleic acid sequences according to the invention may be derived from, for example, SEQ ID NO:1, 3 or 10 and differ therefrom by addition, substitution, insertion or deletion of individual or several nucleotides, but still code for polypeptides with the desired property profile.

Also comprised by the invention are those nucleic acid sequences which comprise "silent" mutations or which are altered, as compared with a specifically mentioned sequence, according to the codon usage of a specific source organism or host organism, as are naturally occurring variants thereof, such as, for example, splice variants or allelic variants.

Another subject matter is sequences obtainable by way of conservative nucleotide substitutions (i.e. the amino acid in question is replaced with an amino acid of the same charge, size, polarity and/or solubility).

Subject matter of the invention is also the molecules which are derived from the specifically disclosed nucleic acids by way of sequence polymorphisms. These genetic polymorphisms may exist between individuals within a population as a result of natural variation. These natural variations usually give rise to a variance of from 1 to 5% in the nucleotide sequence of a gene.

Derivatives of nucleic acid sequences according to the invention and which have the sequence SEQ ID NO:1, 3 or 10 are understood as meaning, for example, allelic variants which, at the deduced amino acid level, have at least 60% homology, preferably at least 80% homology, very especially preferably at least 90% homology over the entire sequence region (in respect of homology at the amino acid level, the reader may refer to the above comments regarding the polypeptides). Advantageously, the homologies may be higher across subregions of the sequences.

Furthermore, derivatives are also understood as meaning homologs of the nucleic acid sequences according to the invention, in particular of the SEQ ID NO:1, 3 or 10 for example fungal or bacterial homologs, truncated sequences, single-stranded DNA or RNA of the coding and noncoding DNA sequence. Thus, for example homologs to the SEQ ID NO:1, 3 or 10 have a homology of at least 40%, preferably of at least 60%, especially preferably of at least 70%, very especially preferably of at least 80% homology at the DNA level over the entire DNA region specified in SEQ ID No:1, 3 or 10.

Furthermore, derivatives are understood as meaning for example fusions with promoters. The promoters which are located upstream of the nucleotide sequences indicated may have been altered by at least one nucleotide substitution, at least one insertion, inversion and/or deletion, without, however, the functionality and efficacy of the promoters being adversely affected. Furthermore, the efficacy of the promoters may be increased by altering their sequence, or the promoters may be replaced entirely with more active promoters, including promoters from organisms of other species.

In addition, a person skilled in the art is familiar with processes for generating functional mutants.

Depending on the technique used, a person skilled in the art may introduce completely random or, also more specific mutations into genes or also non-coding nucleic acid regions (for example regions which are important for regulating expression) and subsequently generate gene libraries. The molecular-biological methods required for this purpose are known to a person skilled in the art and described, for example, in Sambrook and Russell, Molecular Cloning. 3$^{rd}$ Edition, Cold Spring Harbor Laboratory Press 2001.

Methods for modifying genes and thus for altering the protein coded by them have been familiar to a person skilled in the art for a long time, such as, for example, site-specific mutagenesis, where single or multiple nucleotides of a gene are substituted specifically (Trower M K (Ed.) 1996; In vitro mutagenesis protocols. Humana Press, New Jersey), saturation mutagenesis, in which a codon for any desired amino acid may be substituted or added at any desired position of a gene (Kegler-Ebo D M, Docktor C M, DiMaio D (1994) Nucleic Acids Res. 22:1593; Barettino D, Feigenbutz M, Valcárel R, Stunnenberg H G (1994) Nucleic Acids Res 22:541; Barik S (1995) Mol. Biotechnol. 3:1), error-prone polymerase chain reaction (PCR), in which nucleotide sequences are mutated by defectively operating DNA polymerases (Eckert K A, Kunkel T A (1990) Nucleic Acids Res. 18:3739);

the passaging of genes in mutator strains in which for example on account of deficient DNA repair mechanisms the mutation rate of nucleotide sequences is increased (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested, and the fragments are used as templates for a polymerase chain reaction, in which full-length mosaic genes are ultimately generated by repeated strand separation and reannealing (Stemmer W P C (1994) Nature 370:389; Stemmer W P C (1994) Proc. Natl. Acad. Sci. USA 91:10747).

Employing what is known as directed evolution (described, inter alia, in Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (Ed.) Manual of industrial microbiology and biotechnology. American Society for Microbiology), a person skilled in the art can also generate functional mutants in a targeted manner, also on a large scale. Here, gene libraries of the respective proteins are generated in a first step, and these gene libraries may be set up employing, for example, the methods specified hereinabove. The gene libraries are expressed in a suitable manner, for example by bacteria or by phage display systems.

The relevant genes of host organisms which express functional mutants with properties which correspond largely to the desired properties may be subjected to a further mutation cycle. The steps of mutation and of selection or of screening may be repeated iteratively until the functional mutants which are present show the desired properties to a sufficient extent. A limited number of mutations such as, for example, 1 to 5 mutations may be generated stepwise by this iterative approach, and their influence on the relevant enzyme property may be assessed and selected. The selected mutant may then be subjected in the same manner to a further mutation step. This allows the number of individual mutants to be studied to be reduced significantly.

The results according to the invention also provide important information in respect of structure and sequence of the enzymes in question, which enzymes are required for generating, in a targeted fashion, further enzymes with desired modified properties. In particular, it is possible to define what are known as "hot spots", i.e. sequence sections which are potentially suitable for modifying an enzyme property via the introduction of targeted mutations.

3.2 Constructs

Subject matter of the invention is furthermore expression constructs, comprising, under the genetic control of regulatory nucleic acid sequences, a nucleic acid sequence which encodes at least one polypeptide according to the invention; and vectors comprising at least one of these expression constructs.

An "expression unit" is understood as meaning, according to the invention, a nucleic acid with expression activity, which comprises a promoter as defined herein and which, after functional linkage to a nucleic acid to be expressed or to a gene, regulates the expression, that is to say the transcription and the translation, of said nucleic acid or said gene. This is why, in this context, an expression unit is also referred to as a "regulatory nucleic acid sequence". Further regulatory elements, such as, for example, enhancers, may be present in addition to the promoter.

According to the invention, an "expression cassette" or "expression construct" is understood as meaning an expression unit which is functionally linked to the nucleic acid to be expressed or the gene to be expressed. In contrast to an expression unit, therefore, an expression cassette not only comprises nucleic acid sequences which regulate transcription and translation, but also the nucleic acid sequences which are to be expressed as protein as a consequence of the transcription and translation.

In the context of the invention, the terms "expression" or "overexpression" describe the production or increase of the intracellular activity of one or more enzymes in a microorganism, which enzymes are coded by the corresponding DNA. To this end, for example, a gene may be introduced into an organism, an existing gene may be replaced by a different gene, the copy number of the gene(s) may be increased, a strong promoter may be used, or a gene may be used which encodes a corresponding enzyme with a high activity, and, optionally, these measures can be combined.

Preferably, such constructs according to the invention comprise a promoter upstream, i.e. at the 5' end of the particular coding sequence, and a terminator sequence downstream, i.e. at the 3' end, and, optionally, further customary regulatory elements, in each case operably linked to the coding sequence.

A "promoter", a "nucleic acid with promoter activity" or a "promoter sequence" is understood as meaning in accordance with the invention a nucleic acid which, in functional linkage to a nucleic acid to be transcribed, regulates the transcription of said nucleic acid.

In this context, a "functional" or "operable" linkage is understood as meaning, for example, the sequential arrangement of one of the nucleic acids with promoter activity and a nucleic acid sequence to be transcribed and, optionally, further regulatory elements such as, for example, nucleic acid sequences which ensure the transcription of nucleic acids, and, for example, a terminator in such a way that each of the regulatory elements is able to carry out its function as intended in the transcription of the nucleic acid sequence. A direct linkage in the chemical sense is not mandatory in this context. Genetic control sequences, such as, for example, enhancer sequences, may also exert their function on the target sequence from positions which are further removed, or even from different DNA molecules. Preferred arrangements are those in which the nucleic acid sequence to be transcribed is positioned after the promoter sequence (i.e. at its 3' end) so that the two sequences are covalently linked to each other. In this context, the distance between the promoter sequence and the nucleic acid sequence to be expressed recombinantly may be less than 200 base pairs or less than 100 base pairs or less than 50 base pairs.

Examples of further regulatory elements which may be mentioned besides promoters and terminator are targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, Calif. (1990).

Nucleic acid constructs according to the invention comprise in particular a sequence SEQ ID NO:1, 3 or 10 or derivatives and homologs thereof, and the nucleic acid sequences which can be derived therefrom and which have been operably or functionally linked to one or more regulatory signals, advantageously for controlling, for example increasing, gene expression.

In addition to these regulatory sequences, the natural regulation of these sequences may still be present upstream of the actual structural genes and may optionally have been genetically altered in such a way that the natural regulation has been switched off and the expression of the genes has been increased. However, the nucleic acid construct may also have a simpler design, i.e. no additional regulatory signals have been inserted upstream of the coding sequence, and the natural promoter, together with its regulation, has not been removed. Instead, the natural regulatory sequence is mutated in such a way that regulation no longer takes place, and gene expression is increased.

A preferred nucleic acid construct advantageously also comprises one or more of the previously mentioned "enhancer" sequences which are functionally linked to the promoter and which enable expression of the nucleic acid sequence to be increased. Additional advantageous sequences, such as further regulatory elements or terminators, may also be inserted at the 3' end of the DNA sequences. The nucleic acids according to the invention may be present in the construct in one or more copies. The construct may additionally comprise further markers such as antibiotic resistances or auxotrophy-complementing genes, optionally for the purpose of selecting the construct.

Examples of suitable regulatory sequences are present in promoters such as cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or in the lambda-P$_L$ promotors which are advantageously used in Gram-negative bacteria. Other advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation purposes.

For the purposes of expression in a host organism, the nucleic acid construct is advantageously inserted into a vector such as, for example, a plasmid or a phage, which enables the genes to be expressed optimally in the host. Vectors, in addition to plasmids and phages, are also understood as meaning all the other vectors known to a person skilled in the art, i.e. for example viruses such as SV40, CMV, baculovirus and adenovirus, transposons, IS elements, phasmids, cosmids and linear or circular DNA. These vectors may be replicated autonomously in the host organism or replicated chromosomally. These vectors constitute a further development of the invention.

Examples of suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The plasmids mentioned are a small selection of the possible plasmids. Other plasmids are well known to a person skilled in the art and can be found, for example, in the book Cloning Vectors (Eds. Pouwels P. H. et al. Elsevier, Amsterdam-New York-Oxford, 1985, ISBN 0 444 904018).

In a further embodiment of the vector, the vector comprising the nucleic acid construct according to the invention or the nucleic acid according to the invention may also advantageously be introduced into the microorganisms in the form of a linear DNA and integrated into the genome of the host organism via heterologous or homologous recombination. This linear DNA may consist of a linearized vector, such as a plasmid, or only of the nucleic acid construct or of the nucleic acid according to the invention.

In order to express heterologous genes optimally in organisms, it is advantageous to alter the nucleic acid sequences in accordance with the specific "codon usage" employed in the organism. The "codon usage" can be determined readily with the aid of computer analyses of other known genes of the organism in question.

An expression cassette according to the invention is generated by fusing a suitable promoter to a suitable coding nucleotide sequence and to a terminator signal or polyadenylation signal. Common recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression purposes in a suitable host organism, the recombinant nucleic acid construct or gene construct is advantageously inserted into a host-specific vector which enables the genes to be expressed optimally in the host. Vectors are well known to a person skilled in the art and can be found for example in "Cloning Vectors" (Pouwels P. H. et al., Eds., Elsevier, Amsterdam-New York-Oxford, 1985).

4. Microorganisms

Depending on the context, the term "microorganism" may be understood as meaning the starting (wild-type) microorganism or a genetically modified recombinant microorganism, or both.

It is possible to prepare, with the aid of the vectors according to the invention, recombinant microorganisms which are transformed for example with at least one vector according to the invention and which may be used for producing the polypeptides according to the invention. Advantageously, the above-described recombinant constructs according to the invention are introduced into a suitable host system and expressed therein. In this connection, familiar cloning and transfection methods with which a person skilled in the art is familiar, such as, for example, coprecipitation, protoplast fusion, electroporation, retroviral transfection and the like, are preferably used in order to cause said nucleic acids to be expressed in the particular expression system. Suitable systems are described, for example, in Current Protocols in Molecular Biology, F. Ausubel et al., Eds., Wiley Interscience, New York 1997, or Sambrook et al. Molecular Cloning: A Laboratory Manual. $2^{nd}$ edition, Cold Spring Harbor Laboratory, Cold Spring Harbor Laboratory Press, Cold Spring Harbor, N.Y., 1989. An overview of bacterial expression systems for the heterologous expression of proteins is also provided, for example, by Terpe, K. Appl. Microbiol. Biotechnol. (2006) 72: 211-222.

Recombinant host organisms for the nucleic acid according to the invention or the nucleic acid construct are, in principle, all prokaryotic or eukaryotic organisms. It is advantageous to employ, as host organisms, microorganisms such as bacteria, fungi or yeasts. It is advantageous to employ Gram-positive or Gram-negative bacteria, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Comamonas, Streptomyces, Nocardia, Burkholderia, Salmonella, Agrobacterium, Clostridium* or *Rhodococcus*. Very especially preferred is the genus and species *Escherichia coli*. Further advantageous bacteria can furthermore be found in the group of alpha-proteobacteria, beta-proteobacteria or gamma-proteobacteria.

In this context, the host organism(s) according to the invention preferably comprise(s) at least one of the nucleic acid sequences, nucleic acid constructs or vectors which are described in this invention and which encode an enzyme with 7β-HSDH activity as defined hereinabove.

Depending on the host organism, the organisms used in the process according to the invention are grown, or cultured, in a manner known to a person skilled in the art. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and optionally vitamins at temperatures of between 0° C. and 100° C., preferably between 10° C. to 60° C., while passing in oxygen. The pH of the liquid medium can either be kept constant, that is to say regulated during the culturing, or not. The culturing may take place batchwise, semibatchwise or continuously. Nutrients may be provided at the beginning of the fermentation or fed in semicontinuously or continuously.

5. Production of UDCA

Step 1: Chemical Conversion of CA into DHCA

The hydroxyl groups of CA are oxidized to carbonyl groups in a manner known per se via the traditional chemical route, using chromic acids or chromates in acidic solution (for example $H_2SO_4$). This gives rise to DHCA.

Step 2: Enzymatic or Microbial Conversion of DHCA into 12-Keto-UDCA

DHCA is reduced specifically in aqueous solution by 3α-HSDH and 7β-HSDH or mutants thereof in the presence of NADPH or NADH to give 12-keto-UDCA. The cofactor NADPH or NADH can be regenerated by an ADH or FDH or GDH or mutants thereof from isopropanol or sodium formate or glucose, respectively. The reaction proceeds under mild conditions. For example, the reaction may be carried out at pH=6 to 9, in particular approximately pH=8 and at approximately 10 to 30, 15 to 25 or approximately 23° C.

In the event of a microbial conversion step, recombinant microorganisms which express the enzyme activity/activities required may be cultured anaerobically or aerobically in suitable liquid media in the presence of the substrate to be converted (DHCA). Suitable culturing conditions are known per se to a person skilled in the art. They comprise conversions in the pH range of, for example, 5 to 10 or 6 to 9, at temperatures in the range of from 10 to 60 or 15 to 45 or 25 to 40 or 37° C. Suitable media comprise for example the LB and TB media described herein below. In this context, the conversion time may for example be carried out batchwise or continuously or in any other customary process variant (as described hereinabove). The conversion time may, in this context, be for example in the range of from minutes to several hours or days and may amount to, for example, 1 h to 48 h. Optionally, if enzymatic activity is not expressed continuously, the latter may be initiated by adding a suitable inductor after a target cell density of, for example, approximately $OD_{600}$=0.5 to 1.0 has been reached.

As regards the operation of the fermentation, additions to the medium, enzyme immobilization and isolation of the substances of value, further suitable modifications of the microbial production process which are possible can also be found in the following section regarding "production of the enzymes or mutants".

Step 3: Chemical Conversion of 12-Keto-UDCA to UDCA

The 12-carbonyl group of 12-keto-UDCA is removed in a manner known per se by means of Wolff-Kischner reduction, whereby UDCA is generated from 12-keto-UDCA. In the reaction, the carbonyl is first reacted with hydrazine to give the hydrazone. Thereafter, the hydrazone is heated to 200° C. in the presence of a base (for example KOH); during this process, nitrogen is eliminated, giving rise to UDCA.

6. Recombinant Production of the Enzymes and Mutants

Subject matter of the invention is furthermore processes for the recombinant production of polypeptides according to the invention or functional biologically active fragments thereof, wherein a polypeptide-producing microorganism is cultured, the expression of the polypeptides is optionally induced and the polypeptides are isolated from the culture. If desired, the polypeptides may, in this manner, also be produced on an industrial scale.

The microorganisms which have been produced in accordance with the invention can be grown continuously or discontinuously by the batch method, the fed-batch method or the repeated fed-batch method. An overview of known culture methods can be found in the textbook by Chmiel (Bioprozeßtechnik 1. Einführung in die Bioverfahrenstechnik [Bioprocess Engineering 1. Introduction to Bioprocess Technology] (Gustav Fischer Verlag, Stuttgart, 1991)) or in the textbook by Storhas (Bioreaktoren and periphere Einrichtungen [Bioreactors and Peripheral Units] (Vieweg Verlag, Brunswick/Wiesbaden, 1994)).

The culture medium to be used must suitably meet the needs of the strains in question. Descriptions of culture media for a variety of microorganisms are found in the manual "Manual of Methods for General Bacteriology" of the American Society for Bacteriology (Washington D. C., USA, 1981).

These media which can be employed in accordance with the invention usually encompass one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch or cellulose. Sugars may also be added to the media via complex compounds, such as molasses, or other by-products of sugar refining. It may also be advantageous to add mixtures of various carbon sources. Other possible carbon sources are oils and fats such as, for example, soya oil, sunflower oil, peanut oil and coconut fat, fatty acids such as, for example, palmitic acid, stearic acid or linoleic acid, alcohols such as, for example, glycerol, methanol or ethanol, and organic acids such as, for example, acetic acid or lactic acid.

Nitrogen sources are usually organic or inorganic nitrogen compounds or materials comprising these compounds. Examples of nitrogen sources encompass ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soya meal, soya protein, yeast extract, meat extract and others. The nitrogen sources can be used individually or as a mixture.

Inorganic salt compounds which may be present in the media encompass the chloride, phosphorus or sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, but also organic sulfur compounds, such as mercaptans and thiols, may be used as the sulfur source.

Phosphoric acid, potassium dihydrogenphosphate or dipotassium hydrogenphosphate or the corresponding sodium-containing salts may be used as phosphorus source.

Sequestrants may be added to the medium in order to maintain the metal ions in solution. Particularly suitable sequestrants encompass dihydroxyphenols, such as catechol or protocatechuate, or organic acids such as citric acid.

Usually, the fermentation media employed in accordance with the invention also comprise other growth factors such as vitamins or growth promoters, which include, for example, biotin, riboflavin, thiamine, folic acid, nicotinic acid, panthothenate and pyridoxine. Growth factors and salts are frequently obtained from complex media components such as yeast extract, molasses, corn steep liquor and the like. Moreover, suitable precursors may be added to the culture medium. The exact composition of the compounds in the media depends greatly on the experiment in question and is decided individually for each individual case. Information on the optimization of media can be found in the textbook "Applied Microbiol. Physiology, A Practical Approach" (Eds P. M. Rhodes, P. F. Stanbury, IRL Press (1997) pp. 53-73, ISBN 0 19 963577 3). Growth media can also be obtained from commercial sources, such as Standard 1 (Merck) or BHI (brain heart infusion, DIFCO) and the like.

All of the media components are sterilized, either by means of heat (20 minutes at 1.5 bar and 121° C.) or by filter sterilization. The components may be sterilized either together or, if necessary, separately. All of the media components may be present at the beginning of the culturing or else be added continuously or batchwise, as desired.

The culture temperature is normally between 15° C. and 45° C., preferably 25° C. to 40° C., and can be kept constant during the experiment or else be varied. The pH of the medium should be in the range of from 5 to 8.5, preferably around 7.0. The pH for the culturing can be controlled during culturing by addition of basic compounds such as sodium hydroxide, potassium hydroxide, ammonia or ammonia water, or acidic compounds such as phosphoric acid or sulfuric acid. Antifoam agents such as, for example, fatty acid polyglycol esters may be employed to control foam development. To maintain plasmid stability, suitable selectively acting substances such as, for example, antibiotics may be added to the medium. To maintain aerobic conditions, oxygen or oxygen-containing gas mixtures, for example ambient air, are passed into the culture. The culture temperature is normally 20° C. to 45° C. and. The culture is continued until a maximum of the desired product has formed. This aim is normally achieved within 10 hours to 160 hours.

Thereafter, the fermentation broth is processed further. Depending on what is required, all or some of the biomass may be removed from the fermentation broth by separation methods such as, for example, centrifugation, filtration, decanting or a combination of these methods, or else be left completely in said broth.

If the polypeptides are not secreted into the culture medium, the cells may also be disrupted and the product may be obtained from the lysate by known protein isolation methods. The cells can optionally be disrupted by high-frequency ultrasound, by high pressure such as, for example, in a French pressure cell, by osmolysis, by the action of detergents, lytic enzymes or organic solvents, by homogenizers or by a combination of several of the abovementioned methods.

The polypeptides may be purified using known chromatographic techniques, such as molecular sieve chromatography (gel filtration), such as Q-Sepharose chromatography, ion exchange chromatography and hydrophobic chromatography, and also using other common methods such as ultrafiltration, crystallization, salting out, dialysis and native gel electrophoresis. Suitable methods are described for example in Cooper, F. G., Biochemische Arbeitsmethoden [Biochemical working methods], Verlag Walter de Gruyter, Berlin, New York or in Scopes, R., Protein Purification, Springer Verlag, New York, Heidelberg, Berlin.

To isolate the recombinant protein, it may be advantageous to use vector systems or oligonucleotides which extend the cDNA by specific nucleotide sequences and thus encode modified polypeptides or fusion proteins which serve, for example, the purpose of simpler purification. Such modifications which are suitable are, for example, what are known as "tags", which act as anchors, such as, for example, the modification known as hexa-histidine (SEQ ID NO: 52) anchor or epitopes capable of being recognized by antibodies as being antigens (described, for example, in Harlow, E. and Lane, D., 1988, Antibodies: A Laboratory Manual. Cold Spring Harbor (N.Y.) Press). These anchors may serve to attach the proteins to a solid support, such as, for example, a polymer matrix which may be packed into, for example, a chromatography column, or for attaching the proteins to a microtiter plate or any other support.

At the same time, these anchors can also be used for the identification of the proteins. For identifying the proteins, customary markers, such as fluorescent dyes, enzyme markers that, after reaction with a substrate, form a detectable reaction product, or radioactive markers, can moreover be used alone or in combination with the anchors for derivatization of the proteins.

7. Enzyme Immobilization

In the methods described herein, the enzymes according to the invention may be employed in free or immobilized form. An immobilized enzyme is understood as meaning an enzyme which is fixed to an inert support. Suitable support materials, and the enzymes immobilized thereon, are known from EP-A-1149849, EP-A-1 069 183 and DE-OS 100193773 and from the literature cited therein. In this respect, the disclosure of said documents is referred to in its entirety. The suitable support materials include, for example, clays, clay minerals such as kaolinite, diatomaceous earth, perlite, silica, alumina, sodium carbonate, calcium carbonate, cellulose powder, anion exchange materials, synthetic polymers such as polystyrene, acrylic resins, phenol-formaldehyde resins, polyurethanes and polyolefins such as polyethylene and polypropylene. The support materials are conventionally employed in a finely divided, particulate form for the preparation of the supported enzymes, with porous forms being preferred. The particle size of the support material is conventionally not more than 5 mm, in particular not more than 2 mm (grading curve). Analogously, on use of the dehydrogenase as a whole-cell catalyst, a free or an immobilized form may be chosen. Support materials are, for example, calcium alginate and carrageenan. Enzymes as well as cells may also be crosslinked directly using glutaraldehyde (crosslinking to CLEAs). Corresponding and further immobilization processes are described, for example, in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

EXPERIMENTAL PART

Unless otherwise specified, the cloning steps carried out within the scope of the present invention, such as, for example, restriction cleavages, agarose gel electrophoresis, the purification of DNA fragments, the transfer of nucleic acids to nitrocellulose and nylon membranes, the linking of DNA fragments, the transformation of microorganisms, the culturing of microorganisms, the multiplication of phages and the sequence analysis of recombinant DNA may be carried out as described by Sambrook et al. (1989) loc. cit.

A. General Information

Materials:

The genomic DNA of *Collinsella aerofaciens* DSM 3979 (ATCC 25986, formerly referred to as *Eubacterium aerofaciens*) was obtained from the Deutsche Sammlung für Mikroorganismen und Zellkulturen (DSMZ).

The genomic DNA of *C. testosteroni* can be obtained from the Deutsche Sammlung für Mikroorganismen und Zellkulturen (DSMZ) or can be isolated from a *C. testosteroni* strain using methods known per se.

UDCA and 7-keto-LCA are starting compounds which are known per se and described in the literature. All the other chemicals were obtained from Sigma-Aldrich and Fluka (Germany). All restriction endonucleases, T4 DNA ligase, Taq DNA polymerase, Plusion DNA polymerase and isopropyl β-D-1-thiogalactopyranoside (IPTG) were obtained from Fermentas (Germany).

Media:

LB medium, comprising tryptone 10 g, yeast extract 5 g, NaCl 10 g per liter of medium TB medium, comprising tryptone 12 g, yeast extract 24 g, 4 ml glycerol, 10% KPi buffer (11.55 g $KH_2PO_4$, 62.7 g $K_2HPO_4$, ad 500 ml $H_2O$) per liter of medium.

Minimal medium, modified in accordance with Wilms et al., BIOTECHNOLOGY AND BIOENGINEERING, 2001 VOL. 73, NO. 2, 95-103

Sequences:

FIGS. 3A-3B shows the amino acid sequences of the wild-type 7β-HSDH enzyme and of mutants; however, all are in each case provided in a C-terminal hexa-histidine tag (SEQ ID NO: 52). In this manner, all the enzymes have been isolated and characterized.

Example 1: Production of the Recombinant 3α-HSDH

A) Plasmid Transformation:

The commercially available expression vector pET28a (+), into which the respective 3α-HSDH gene has been cloned via the cleavage sites of the restriction enzymes NcoI/Eco31I and XhoI, was used for the expression of the recombinant 3α-HSDH enzymes (wild-type and mutant enzymes). The expression vector pET28a(+) makes it possible, when cloning the HSDH gene, to directly attach a gene sequence to the HSDH gene, which sequence codes for a succession of 6 histidine molecules (SEQ ID NO: 52). Following the expression, this sequence (referred to as hexahistidine tag (SEQ ID NO: 52) or His-tag) appears C-terminally on the HSDH protein. The original, or wild-type, HSDH gene originates from the bacterium *Comamonas testosteroni*, and the plasmid which comprises the respective 3α-HSDH gene is referred to as pET28a(+)_3α-HSDH. To transform the pET28a(+)_3α-HSDH plasmid, 5 μl of ligation mixture was treated with 100 μl of competent BL21(DE3)Δ7α-HSDH *E. coli* cells, and the transformation was carried out as described by Hanahan (J. Mol. Biol. (1983), vol. 166, pp. 557), the same steps being carried out with the plasmid which comprises the wild-type gene and with the plasmid that comprises mutated HSDH genes. *E. coli* strain BL21(DE3)Δ7α-HSDH, which has been used regularly in this context, is distinguished in that the gene for the 7α-HSDH has been deleted in this strain. The precise characterization of the *E. coli* strains used for this work is compiled in table 1.

TABLE 1

Escherichia coli strains used

| Strain | Genotype |
|---|---|
| Escherichia coli DH5α | F-endA1 glnV44 thi-1 recA1 relA1 gyrA96 deoRnupG φ80dlacZΔM15 Δ(lacZYA-argF)U169, hsdR17(rK-mK+), λ- |
| Escherichia coli BL21 (DE3) Δ7α-HSDH (=E. coli with deleted 7α-HSDH) | F-ompTgaldcmlonhsdSB(rB-mB-) λ(DE3 [lacI lacUV5-T7 gene 1 ind1 sam7 nin5]) hshA-KanR+ |

B) Expression and Cell Propagation:

For expression, the E. coli strain which comprises the expression construct (pET28a(+)_3α-HSDH plasmid) was multiplied for 20 hours in LB medium (trypton 10 g, yeast extract 5 g, NaCl 10 g per liter) at 25° C., the medium comprising 50 µg/ml kanamycine. The cells were harvested by centrifugation (5000×g, 30 min, 4° C.).

C) Obtaining the Crude Extract:

The pellet was resuspended in disruption buffer (10 mM imidazole, 50 mM sodium phosphate, 300 mM NaCl, pH 8), with 4 ml of buffer being added per 1 g of cells (moist mass). The cells were then disrupted by sonication for one minute (30 W power, 50% working interval and 1 min break), with constant cooling, using a Sonopuls HD2070 sonicator (Bandelin, Berlin, Germany). The disruption was repeated three times. The cell suspension was centrifuged (18 000×g, 30 min, 4° C.), with the supernatant being referred to as cell-free crude extract.

D) Purification of the Enzyme:

The His-tag allows for very simple purification of the HSDH protein since this sequence is bound with high specificity by specific chromatographic material (NTA (Ninitrilotriacetate)-modified support material, loaded with divalent nickel ions, for example "His Pur Ni-NTA" (Nimagen B. V., Nijmegen, The Netherlands)). To this end, the cell-free crude extract is applied to a dropping column comprising this material, which dropping column has previously been equilibrated with the disruption buffer (3 to 5 column volumes). Weakly binding protein was removed by washing with 3 to 5 column volumes of wash buffer (20 mM imidazole, 50 mM sodium phosphate, 300 mM NaCl, pH 8). The His-tag-3α-HSDH protein was eluted with imidazole-comprising elution buffer (250 mM imidazole, 50 mM sodium phosphate, 300 mM NaCl, pH 8). The process was carried out at room temperature. The imidazole which was present was to be removed by buffer exchange.

The protein concentration was determined by the method described by Bradford (mix 100 µl sample with 900 µl of Bradford reagent, incubate for at least 15 min in the dark, then determination at 595 nm against a calibration curve established with bovine serum albumin).

To perform an SDS-PAGE (SDS polyacrylamide gel electrophoresis) analysis, the gel was stained with Coomassie Brilliant Blue.

E) Activity Determination:

The activity of the 3α-HSDH and of the mutants was determined using a photometric assay, where the decrease in absorbance was measured at 340 nm over a period of 30 seconds. In a total volume of 1 ml, the reaction solution comprised: 874 µl 50 mM potassium phosphate (KPi) buffer, pH 8.0; 100 µl 100 mM of a dehydrocholic acid (DHCA) solution (DHCA dissolved in 50 mM KPi, pH 8); 10 µl of the enzyme solution (optionally diluted); 16 µl of a 12.5 mM NADPH solution (dissolved in dist. H$_2$O). In what follows, the activity is specified in units (U), with 1 U corresponding to the decrease of 1 µMol NADPH/min.

Example 2: Generation of 3α-HSDH Mutants in Amino Acid Position 34, and their Characterization A) Primer:

The mutagenesis primers specified in table 2 were used for carrying out the position-directed mutagenesis of the 3α-HSDH. Based on the 3α-HSDH gene sequence, the primers were selected such that they bring about the desired amino acid exchange.

The following primer pairs were used for generating the mutants:

TABLE 2 primers for the position-directed mutagenesis of the 3α-HSDH at position 34

| Name | Exchange | Primer | 5' -> 3' Sequence | SEQ ID NO: |
|---|---|---|---|---|
| R34N_for | asparagine | forward | GGCATCGATATAAACGATGCGGAAGTG | 12 |
| R34N_rev | | reverse | CACTTCCGCATCGTTTATATCGATGCC | 13 |
| R34L_for | leucine | forward | TCGTAGGCATCGATATACTCGATGCGGAAGTGAT | 14 |
| R34L_rev | | reverse | ATCACTTCCGCATCGAGTATATCGATGCCTACGA | 15 |
| R34S_for | serine | forward | ACCAGATCGTAGGCATCGATATAAGCGATGCGGAAG | 16 |
| R34S_rev | | reverse | CTTCCGCATCGCTTATATCGATGCCTACGATCTGGT | 17 |
| R34C_for | cysteine | forward | ACCAGATCGTAGGCATCGATATATGCGATGCGGAAG | 18 |
| R34C_rev | | reverse | CTTCCGCATCGCATATATCGATGCCTACGATCTGGT | 19 |

B) QuikChange®-PCR:

A targeted exchange of an amino acid may be achieved with the "QuikChange®-PCR" method. To this end, the following PCR reaction was carried out (reaction mixture see table 3): first, an initial denaturation step for 2 min at 95° C. was carried out, thereafter, 20 cycles of denaturation (30 s at 95° C.), primer hydridization (1 min at 60-68° C.) and elongation (11 min at 68° C.) was carried out. The last step that was carried out was a final elongation of 10 min at 68° C., whereafter the polymerase chain reaction was ended by cooling to 4° C. The template used was a pET28a vector with the gene of the 3α-HSDH (wild type).

TABLE 3

PCR mixture for the generation of the various 3α-HSDH variants
PCR Reaction mixture

| | |
|---|---|
| buffer (10x) | 5.0 µl |
| dNTP mix (10 mM) | 1.5 µl |
| Forward primer (10 pmol/µl) | 2.5 µl |
| Reverse primer (10 mol/µl) | 2.5 µl |
| Template | 1.0 µl |
| Pfu polymerase | 0.5 µl |
| DMSO | 2.0 µl |
| ddH₂O | 35.0 µl |
| | 50.0 µl |

In order to be able to exchange amino acids in protein sequences in a targeted fashion, the DNA sequence of the gene in question is subjected to position-directed mutation. To this end, one makes use of primers which are complementary to each other and which contain the desired mutation in their sequence. The template used is N6-adenine-methylated double-stranded plasmid DNA which contains the gene to be mutated. N6-adenine methylated plasmid DNA are isolated from a dam+ *E. coli* strain such as, for example *E. coli* DH5α.

The polymerase chain reaction is carried out as described hereinabove. Here, the primers are extended to complement the template, giving rise to plasmids which have the desired mutation and which have a strand break. In contrast to other PCR reactions, the increase in the DNA yield is only linear here since newly-formed DNA molecules cannot act as template for the PCR reaction.

After the PCR reaction had been concluded, the PCR product was purified by means of the PCR Purification Kit (Analytik Jena AG, Jena, Germany) and the parental, N6-adenine-methylated was digested with the aid of the restriction enzyme dpnI. The peculiarity of this enzyme is that it unspecifically restricts N6-adenine-methylated DNA, but not the newly-formed unmethylated DNA. Restriction took place by adding 1 µl of dpnI to the PCR reaction mixture and incubating the mixture for at least 2 h or overnight at 37° C. 7.5 µl of this mixture were applied for the transformation of 100 µl of chemically competent DH5a cells.

C) Activity Data of the Enzyme Mutants:

The activity measurements (see example 1) of the mutants which had been mutagenized in position 34 revealed the data shown in table 4 herein below.

TABLE 4 activities of the various 3α-HSDH variants which have been modified at position 34.

| Mutant | Volumetric activity [U/ml] | Specific activity [U/mg] |
|---|---|---|
| 3α-HSDH (WT) | 38.0 | 2.1 |
| 3α-HSDH [R34N] | 58.0 | 3.0 |
| 3α-HSDH [R34C] | 38.5 | 2.8 |
| 3α-HSDH [R34S] | 38.7 | 2.3 |
| 3α-HSDH [R34L] | 20.1 | 1.5 |

The best mutant ([R34N]) displays an activity which is improved by approx. 3-fold.

Example 3: Generation of 3α-HSDH Mutants at Amino Acid Position 68, and their Characterization The following text describes 3α-HSDH mutants in which aspartic acid at position 68 were exchanged for some other amino acids. Advantageous mutants are characterized in detail by their kinetics by determining the parameters $K_M$ and $v_{max}$ via Michaelis-Menten kinetics. In order to be able to compare mutants with the wild-type enzyme, the wild-type enzyme was likewise purified beforehand and characterized in terms of its kinetics.

A) Michaelis-Menten Kinetics of the Wild-Type Enzyme

In order to demonstrate clearly the modifications of the mutant in respect of the kinetic constants, the wild-type enzyme has been purified and characterized in the following text.

Figure 4A:
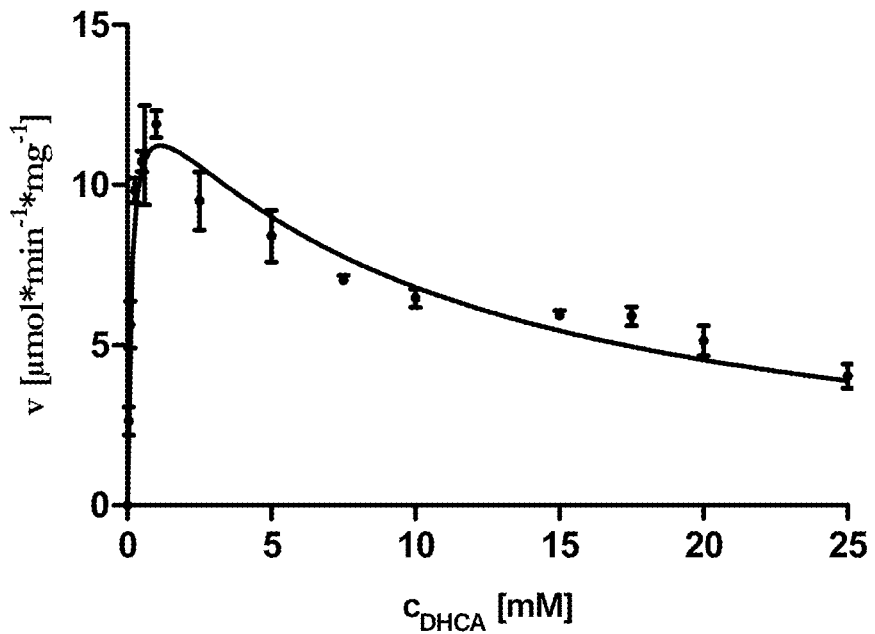
FIG. 4A shows the Michaelis-Menten kinetics of the purified 3α-HSDH with His tag for the substrate DHCA and FIG. 4B shows the Michaelis-Menten kinetics of the purified 3α-HSDH with His tag for the cofactor NADH.
Figure 4B:
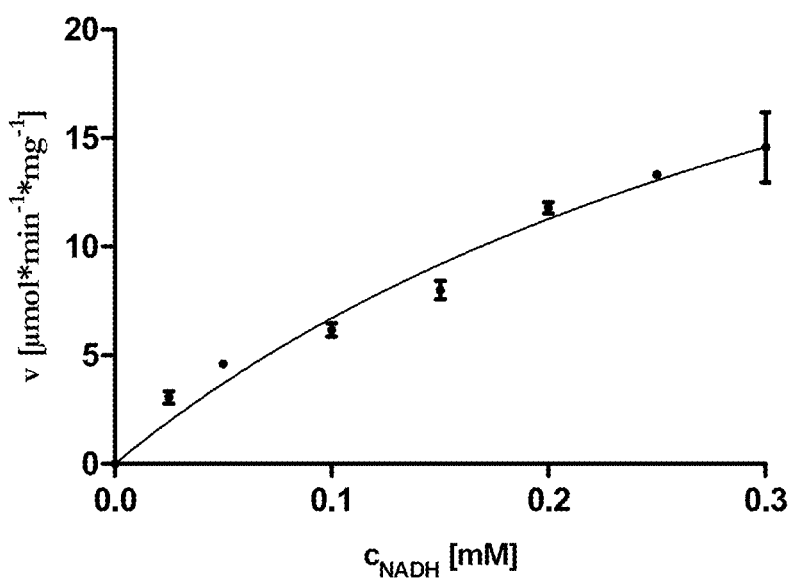
Figure 5A:
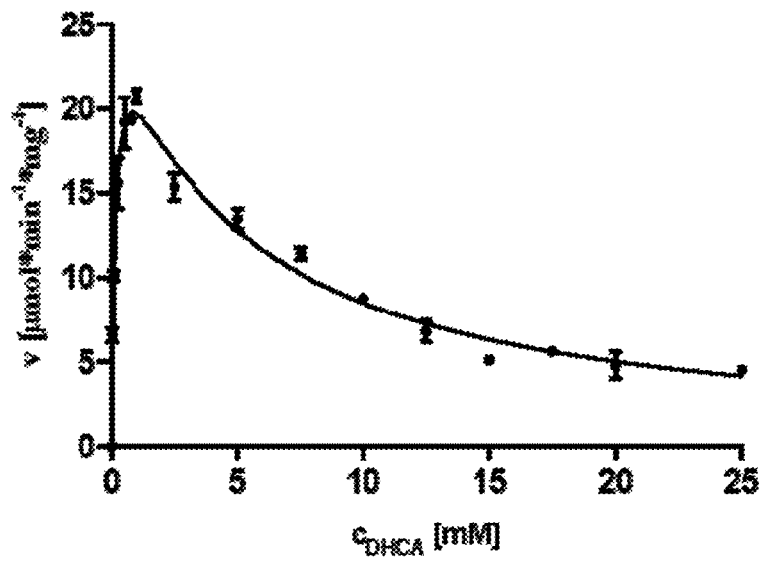
FIG. 5A shows the Michaelis-Menten kinetics of the alanine mutant [L68A] for the substrate DHCA and FIG. 5B shows the Michaelis-Menten kinetics of the alanine mutant [L68A] for the coenzyme NADH.
Figure 5B:
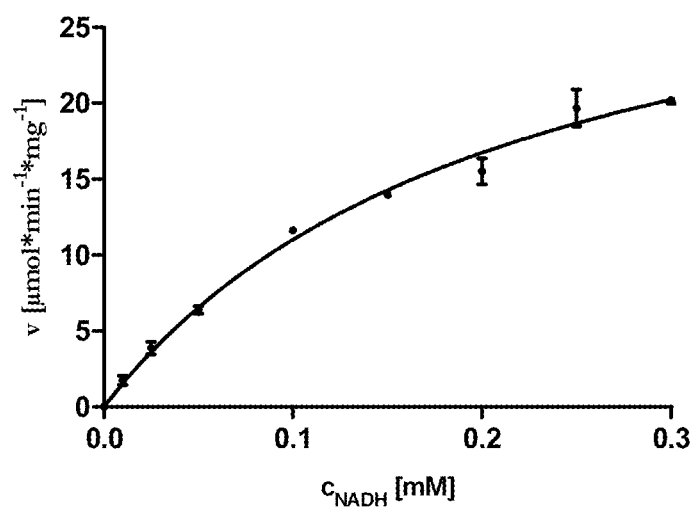

The data for the purified enzyme with a His tag are given in FIGS. 4A-4B and Table 5.

TABLE 5 kinetic constants for the wild-type enzyme for the substrate DHCA and the cofactor NADH.

| Fraction | Substrate | $v_{max}$(U/mg) | $K_M$ (µM) | $K_I$ (mM) |
|---|---|---|---|---|
| 3α-HSDH | DHCA | 13.86 ± 0.8 | 134.3 ± 25.6 | 9.78 ± 1.4 |
| | NADH | 35.36 ± 8.1 | 427.2 ± 146.3 | x |

(x = no inhibition)

1) Primers for the Construction of Mutants

The mutagenesis primers listed in table 6 were used for the position-directed mutagenesis of the 3α-HSDH. Based on the 3α-HSDH gene sequence, the primers were selected such that they bring about the desired amino acid exchange.

The following primer pairs were used for generating the mutants:

TABLE 6 primers for the position-directed mutagenesis of the 3α-HSDH at position 68

| Name | Exchange | Primer | 5' -> 3' Sequence | SEQ ID NO: |
|---|---|---|---|---|
| L68S_for | serine | forward | GGACGGCCTGGTGTCGTGCGCCGGCCTG | 20 |
| L68S_rev | | reverse | CAGGCCGGCGCACGACACCAGGCCGTCC | 21 |
| L68C_for | cysteine | forward | GGACGGCCTGGTGTGCTGCGCCGGCCTGG | 22 |
| L68C_rev | | reverse | CCAGGCCGGCGCAGCACACCAGGCCGTCC | 23 |
| L68K_for | lysine | forward | GGACGGCCTGGTGAAGTGCGCCGGCCTG | 24 |
| L68K_rev | | reverse | CAGGCCGGCGCACTTCACCAGGCCGTCC | 25 |

TABLE 6-continued primers for the position-directed mutagenesis of the 3α-HSDH at position 68

| Name | Exchange | Primer | 5' -> 3' Sequence | SEQ ID NO: |
|---|---|---|---|---|
| L68V_for | valine | forward | ACGGCCTGGTGGTGTGCGCCGGC | 26 |
| L68V_rev | | reverse | GCCGGCGCACACCACCAGGCCGT | 27 |
| L68A_for | alanine | forward | GACGGCCTGGTGGCGTGCGCCGGCCT | 28 |
| L68A_rev | | reverse | AGGCCGGCGCACGCCACCAGGCCGTC | 29 |

B) QuikChange® PCR:

The targeted exchange of aspartic acid at position 68 was carried out by means of QuikChange® PCR as described in example 2B.

C) Activity Values of the Enzyme Mutants:

The photometric activity measurements (see example 1) of the mutants which have been mutagenized at position 68 gave the data listed in table 7 which follows.

TABLE 7 activities of the various 3α-HSDH variants which were modified at position 68.

| Mutant | Volumetric activity [U/ml] | Specific activity [U/mg] |
|---|---|---|
| 3α-HSDH (WT) | 44.9 | 2.1 |
| 3α-HSDH [L68A] | 157 | 6.4 |
| 3α-HSDH [I68C] | 57.5 | 3.4 |
| 3α-HSDH [L68K] | 40 | 3.1 |
| 3α-HSDH [L68S] | 39.6 | 3.1 |
| 3α-HSDH [L68V] | 60 | 2.3 |

D) Michaelis-Menten Kinetics

The best mutant (3α-HSDH [L68A]) was purified (see 1 D), and its kinetic parameters $v_{max}$ and $K_M$ were determined. FIGS. 4A-4B shows the diagrams of the kinetic's courses, and the kinetic constants derived therefrom are listed in Table 8.

TABLE 8 kinetic constants for mutant L68A for the substrate DHCA and the cofactor NADH.

| Enzyme | Substrate | $v_{max}$(U/mg) | $K_M$ (mM) | $K_I$ (mM) |
|---|---|---|---|---|
| L68A | DHCA | 27.3 ± 1.17 | 0.17 ± 0.02 | 4.55 ± 0.41 |
| | NADH | 34.77 ± 2.77 | 0.22 ± 0.03 | x |

(x = no inhibition)

It can be seen from table 7 that it was possible to increase the maximum velocity over the wild-type enzyme (see herein below under 3E) by approximately 2-fold. The $K_M$ value of the mutant is in a similar order of magnitude as the value for the wild-type enzyme.

Example 4: Generation of a 3α-HSDH Mutant which Comprises Amino Acid Exchanges in Several Positions, and their Characterization Besides the individual mutants described in examples 2 and 3, it is also possible to advantageously combine mutations. By way of example, a dual mutant was generated in which position 34 and 68 were modified at the same time.

Here, the best amino acid exchange at position 34 ([R34N]) was combined with the best exchange at position 68 ([L68A]).

A) Generation of the Dual Mutant and Activity Values

The method of obtaining the dual mutant, and the activity test, followed the methods as described under example 2B and 2C. Table 9 compiles the activity of the dual mutant in the crude extract in comparison with the activity of the wild-type enzyme.

TABLE 9 activity of the 3α-HSDH dual mutant which were modified at position 34 and 68.

| Mutant generated | Volumetric activity [U/ml] | Specific activity [U/mg] |
|---|---|---|
| 3α-HSDH (WT) | 44.9 | 2.1 |
| 3α-HSDH [R34N/L68A] | 139.7 | 4.5 |

B) Expression Control by SDS Polyacrylamide Gel Electrophoresis (SDS-PAGE)

Figure 6A:
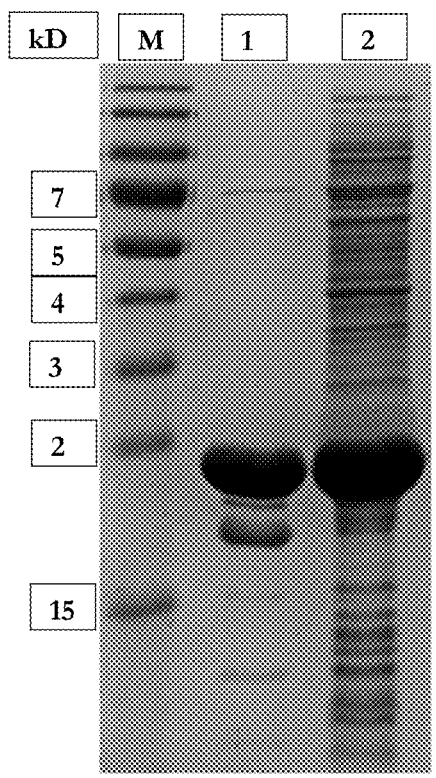
FIG. 6A shows the SDS gel of the 3α-HSDH [R34N/L68A] and FIG. 6B shows the SDS gel of the 3α-HSDH [L68A] and after expression in shake flask fermentation in LB. The soluble fraction applied is the cell-free crude extract. The 3α-HSDHs have a size of approx. 27.4 kDa. Approximately 10 µg of protein were applied. Key: 1=purified 3α-HSDH [R34N/L68A]; 2=crude extract 3α-HSDH [R34N/L68A]; 3=purified 3α-HSDH [L68A]; 4=crude extract 3α-HSDH [L68A].
Figure 6B:
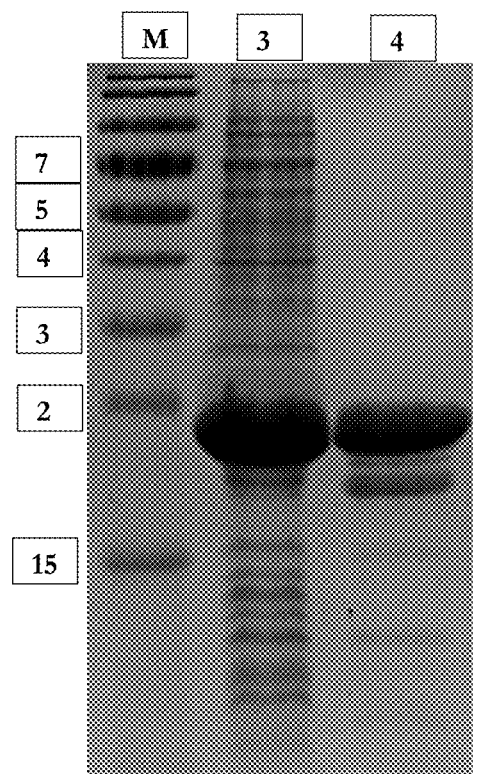

An SDS-PAGE was carried out in order to be able to assess the expression performance of the heterologous expression. FIGS. 6A-6B show the SDS gels of the mutant 3α-HSDH [R34N/L68A] and [L68A]. The size of the mutants was approximately 27.4 kDa. The figures shows that the 3α-HSDHs does not migrate according to its size in the SDS gel. It always migrates somewhat below the 25 kDa band of the marker.

C) Michaelis-Menten Kinetics

Figure 7A:
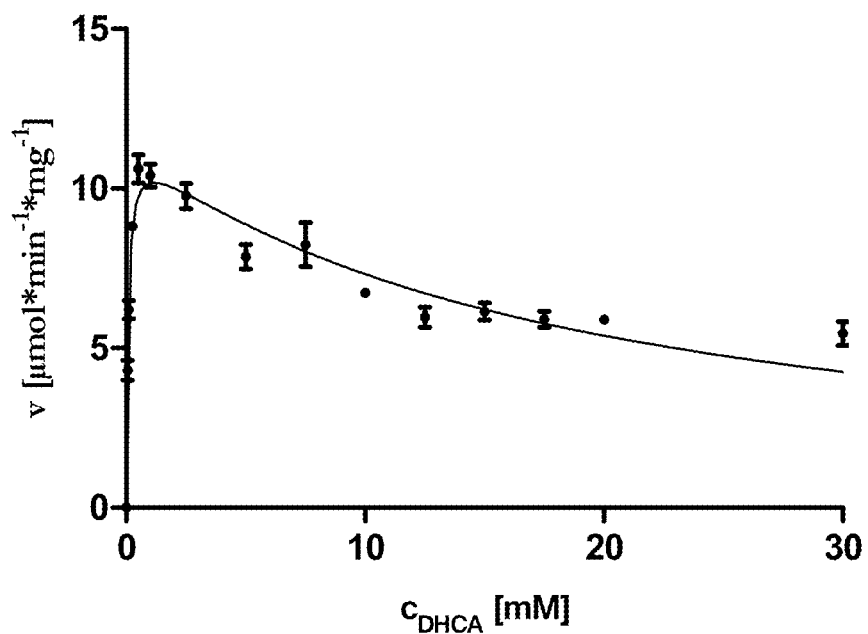
FIG. 7A shows the Michaelis-Menten kinetics for the dual mutant [R34N/L68A] for the substrate DHCA and FIG. 7B shows the Michaelis-Menten kinetics for the coenzyme NADH.
Figure 7B:
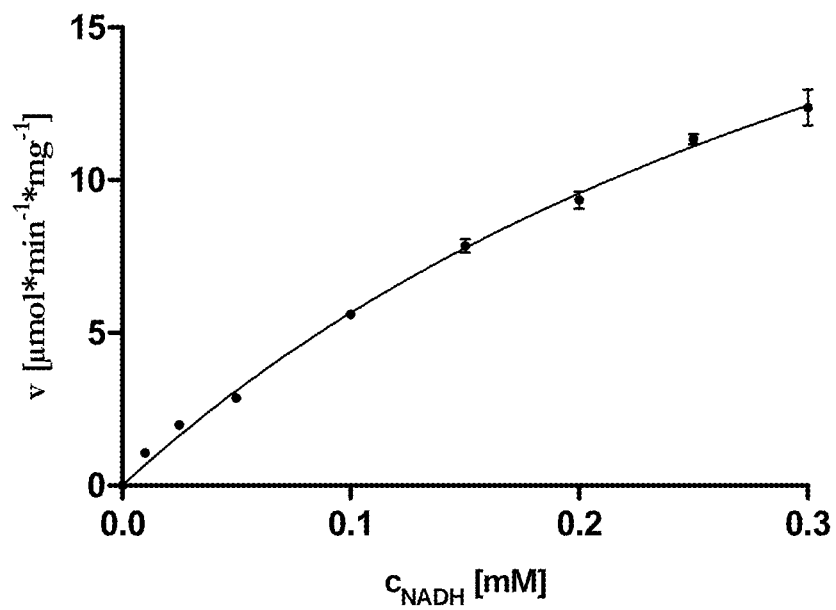

The mutant 3α-HSDH [R34N/L68A] was purified, and the kinetic parameters were determined for the purified enzyme. FIGS. 7A-7B show the diagrams of the Michaelis-Menten kinetics.

D) Activity Values for the Dual Mutant

Table 10 compiles the activity values for the dual mutant as have been established on the basis of the Michaelis-Menten kinetics.

TABLE 10 kinetic constants for the purified enzyme 3α-HSDH [R34N/L68A] for the substrate DHCA and the cofactor NADH.

| Enzyme | Substrate | $v_{max}$(U/mg) | $K_M$ (mM) | $K_I$ (mM) |
|---|---|---|---|---|
| R34N/L68A | DHCA | 16.45 ± 0.56 | 0.08 ± 0.01 | 17.6 ± 1.9 |
| | NADH | 44.38 ± 3.1 | 0.45 ± 0.07 | x |

Key:
x = no inhibition

It was possible to increase the maximum activity of the dual mutant by approx. 25% over the wild type. The $K_M$ value has improved dramatically: a value of 134 μM was determined for the wild-type enzyme, while the mutant shows a $K_M$ value of 80 μM.

Figure 8A:
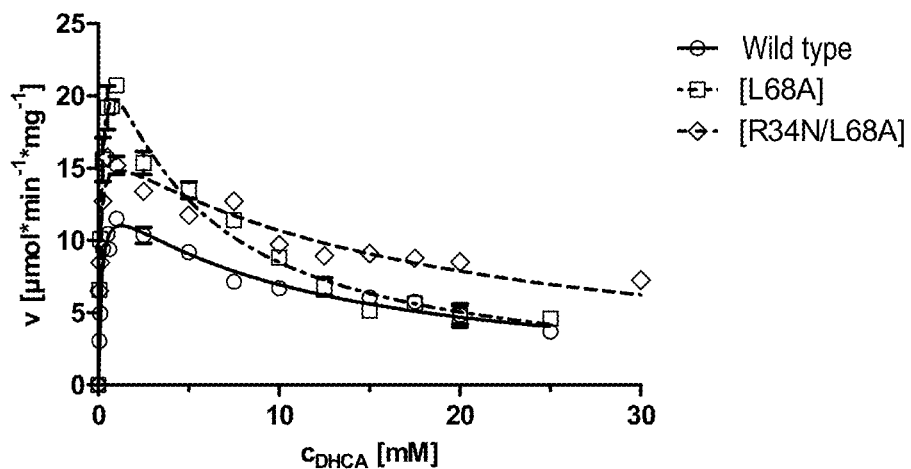
FIG. 8A shows the comparison of the kinetic constants of wild-type enzyme, of the mutant L68A and of the dual mutant R34N/L68A for substrate DHCA
Figure 8B:
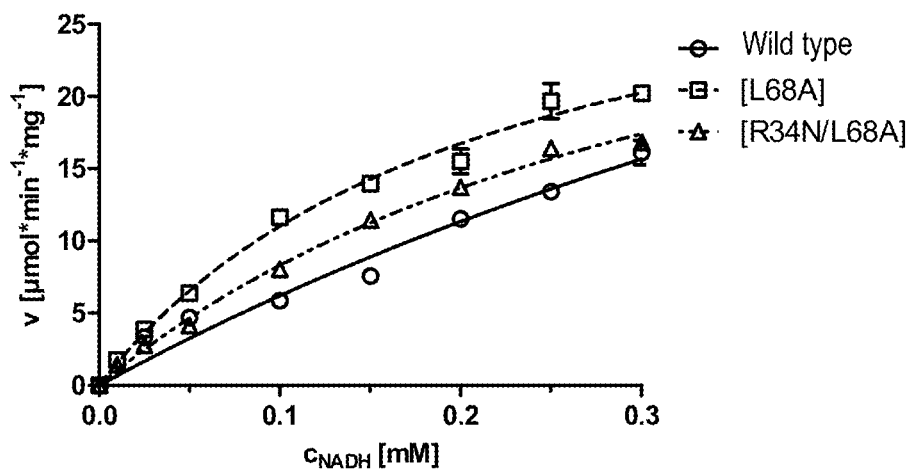
FIG. 8B shows the comparison of the kinetic constants of wild-type enzyme, of the mutant L68A and of the dual mutant R34N/L68A for coenzyme NADH.

E) Summary of the Comparison of the Michaelis-Menten Kinetics of Mutants ([L68A]) and Dual Mutant [R34N/L68A]) with the Wild Type The diagrams of the courses of the respective mutants were compared with the wild type as shown in FIGS. 8A-8B. The already modified wild-type enzyme with His tag was used here for the comparison. It emerges that, while the single mutant (L68A) shows an improved activity (with DHCA), the substrate excess inhibition is slightly more pronounced. The combination of the two positions has resulted in this mutant not being quite as active as the wild type at low substrate concentrations (DHCA), while the dual mutant has markedly higher activities than the wild-type enzyme at higher substrate concentrations, that is to say in a range which is important for the application.

Example 5: Effect of the Hexahistidine (his) Tag (SEQ ID NO: 52)

Figure 10A:
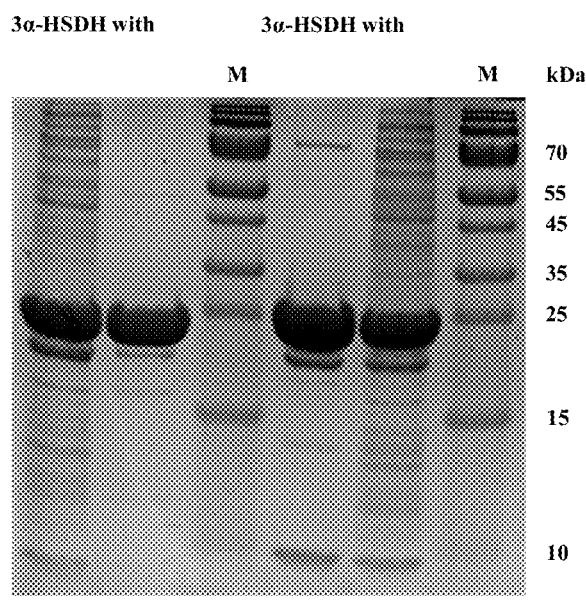
FIG. 10A shows the SDS gel of the 3α-HSDH with 3×His and 9×His tag (SEQ ID NO: 51)
Figure 10B:
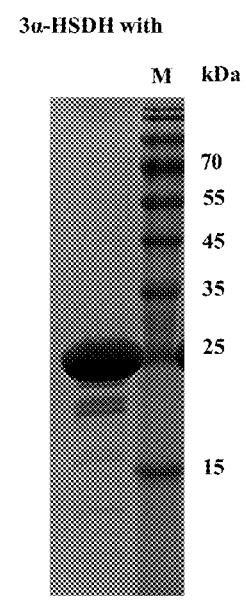
FIG. 10B shows the SDS gel of the 3α-HSDH with the standard 6×His tag (SEQ ID NO: 52). The expression was carried out in shake flask fermentation in LB medium. The soluble fraction applied is the cell-free crude extract and the purified protein. The 3α-HSDH 3×His has a size of approx. 27.1 kDa, the 6×His (SEQ ID NO: 52) a size of approx. 27.5 kDa and the 9×His (SEQ ID NO: 51) a size of approx. 27.9 kDa. Approximately 10 µg of protein were applied.

When comparing the activities of the wild-type enzyme with and without His tag, it was noted that the activities differed clearly from each other. In order to demonstrate the effect of the 6×His tag (SEQ ID NO: 52) more clearly, a 3α-HSDH variant with a 3×His tag and with a 9×His tag (SEQ ID NO: 51) at the C terminus was generated by means of QuickChange® PCR. Following expression (25° C., 0.5 mM, IPTG, 20 hours), the protein was purified, and the expression and the purification were checked by means of an SDS gel. The appended FIGS. 10A-10B show the SDS gels, and Table 11 which follows shows the kinetic constants of the various variants.

TABLE 11 kinetic constants of the non-tagged and the tagged 3α-HSDH for the substrate DHCA.

| Fraction | Substrate | $v_{max}$(U/mg) | $K_M$ (μM) | $K_I$ (mM) |
|---|---|---|---|---|
| Crude extract (without His tag) | DHCA | 25* | 200* | 1* |
| Crude extract (with His tag) | DHCA | 13.5 ± 0.72 | 183.4 ± 25.4 | 2.9 ± 0.3 |

Key:
*= kinetic constant as read from the diagram.

Figure 9:
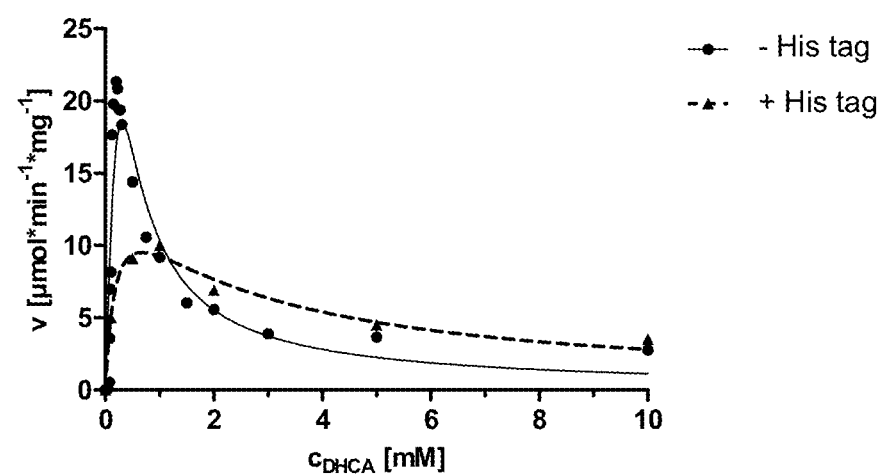
FIG. 9 shows the Michaelis-Menten kinetics of the wild-type 3α-HSDH for the substrate DHCA, recorded in each case with crude extract. The curve with points shows the dependency of the reaction rate on the substrate concentration for the enzyme without His tag, the curve with triangles for the enzyme with C-terminal His tag.

FIG. 9 and the values in Table 11 show that the enzyme can be provided with a His tag at least C-terminally without losing activity. It is characteristic of the wild-type enzyme that, while it has a high affinity to the substrate and reaches its maximum activity at approximately 1 mM only, the activity drops drastically after increasing the DHCA further (FIG. 9, black dots). The non-tagged enzyme only has a residual activity of approximately 10-20%. The His-tag variant of the enzyme, in contrast, shows a markedly different behavior. While, with increasing DHCA concentration, the activity does not increase quite so drastically in the low DHCA concentration range, i.e. the affinity is somewhat reduced, this enzyme no longer demonstrates the pronounced substrate excess inhibition. Thus, the tagged enzyme has better properties than the non-tagged enzyme in particular for preparative applications, which are done at higher DHCA concentrations.

Example 6: Effect of Histidine (his) Tag Length

When comparing the activities of the wild-type enzyme with and without His tag, it was noted that the activities differed clearly from each other. In order to demonstrate the effect of the 6×His tag more clearly, a 3α-HSDH variant with a 3×His tag and with a 9×His tag at the C terminus was generated by means of Quick-Change® PCR. Following expression (25° C., 0.5 mM, IPTG, 20 hours), the protein was purified, and the expression and the purification were checked by means of an SDS gel. FIGS. 10A-10B show the SDS gels, and Table 12 which follows shows the kinetic constants of the various variants.

TABLE 12 comparison of the kinetic constants of 3α-HSDH with different histidine numbers at the C terminus. The constants were recorded with a DHCA concentration of between 10 μM and 10 mM. The NADH concentration was 0.2 mM. Purified protein was employed in the measurements.

| His tag length | vmax [U/mg] | KM [μM] | KI [mM] | kcat [s−1] | kcat/KM [s−1 mM−1] |
|---|---|---|---|---|---|
| 3 | 14.3 ± 4.8 | 997.9 ± 483 | 1.3 ± 0.6 | 6.5 ± 2.1 | 6.5 ± 2.1 |
| 6 (SEQ ID NO: 52) | 14.6 ± 0.9 | 151.1 ± 31.0 | 7.7 ± 1.4 | 6.3 ± 0.7 | 47.2 ± 5.4 |
| 9 (SEQ ID NO: 51) | 19.2 ± 1.1 | 70.5 ± 14.2 | 4.2 ± 0.8 | 8.9 ± 0.5 | 126.3 ± 4.9 |

The kinetic constants shown in table 12 confirm the assumption that the C-terminal histidine residue has an effect on the catalytic property. It can be seen very clearly from the table that the affinity increases with increasing His tag length. The enzyme variant with a tail of 9 histidines (SEQ ID NO: 51) demonstrates a KM value which is 14-fold better than the variant with 3 histidines at the C terminus. Furthermore, the catalytic efficiency (kcat/KM) demonstrates that it increases with increasing histidine chain length; the variant with 9 histidines (SEQ ID NO: 51) has a 19-fold higher efficiency than the variant with only 3 histidines.

Example 7: Generation and Characterization of Further 3α-HSDH Single and Dual Mutants at Positions P185, T188 and Optionally Additionally L68

A) Primers:

The mutagenesis primers specified in table 13 were used for the position-directed mutagenesis of the 3α-HSDH. Based on the 3α-HSDH gene sequence, the primers were chosen such that they bring about the desired amino acid exchange.

The following primer pairs were used for generating the mutants:

TABLE 13 primers for the position-directed mutagenesis of the 3α-HSDH at position 185 and 188

| Position | | Primer sequence sense (forward) | SEQ ID NO: | | Primer sequence antisense (reverse) | SEQ ID NO: | Exchange to |
|---|---|---|---|---|---|---|---|
| P185 | | | | | | | |
| | P185A-for | AACACCATCGCCGCCGGTGCAACCG | 30 | P185A-rev | CGGTTGCACCGGCGGCGATGGTGTT | 31 | alanine |
| | P185G-for | GAACACCATCGCCGGCGGTGCAACCGAG | 32 | P185G-rev | CTCGGTTGCACCGCCGGCGATGGTGTTC | 33 | glycine |
| | P185T-for | GAACACCATCGCCACCGGTGCAACCGA | 34 | P185T-rev | TCGGTTGCACCGGTGGCGATGGTGTTC | 35 | threonine |
| | P185V-for | CTGAACACCATCGCCGTCGGTGCAACCGAGAC | 36 | P185V-rev | GTCTCGGTTGCACCGACGGCGATGGTGTTCAG | 37 | valine |
| | P185S-for | CTGAACACCATCGCCAGCGGTGCAACCGAGAC | 38 | P185S-rev | GTCTCGGTTGCACCGCTGGCGATGGTGTTCAG | 39 | serine |
| T188 | | | | | | | |
| | T188A-for | CGCCCCCGGTGCAGCCGAGACTCC | 40 | T188A-rev | GGAGTCTCGGCTGCACCGGGGCG | 41 | alanine |
| | T188S-for | CCCCCGGTGCAAGCGAGACTCCC | 42 | T188S-rev | GGGAGTCTCGCTTGCACCGGGGG | 43 | serine |
| | T188V-for | ATCGCCCCCGGTGCAGTCGAGACTCCCTTG | 44 | T188V-rev | CAAGGGAGTCTCGACTGCACCGGGGGCGAT | 45 | valine |
| | T188G-for | TCGCCCCCGGTGCAGGCGAGACTCCCTT | 46 | T188G-rev | AAGGGAGTCTCGCCTGCACCGGGGGCGA | 47 | glycine |
| | T188W-for | ATCGCCCCCGGTGCATGGGAGACTCCCTTGCTG | 48 | T188W-rev | CAGCAAGGGAGTCTCCCATGCACCGGGGGCGAT | 49 | tryptophan |

The abovementioned mutagenesis primers (see table 6) were used for the mutations at position L68.

B) QuikChange® PCR:

The targeted exchange of amino acid radicals was performed analogously to Example 2B. To this end, the wild-type gene of the 3α-HSDH in the plasmid pET28a(+)3α-HSDH(N-His), with an N-terminal hexahistidine tag and also with a C-terminal hexahistidine tag in the plasmid pET28a(+) 3α-HSDH (C-His) was modified by means of QuikChange® PCR such that the mutants shown in table 14 and 15 herein below were generated.

Following cultivation and expression, the cells were harvested, and the specific activities of the cell-free crude extracts were determined at substrate concentrations of 10 mM DHCA. The enzyme variants where the activity measurements with crude extract enzyme were most promising were purified by means of Ni-NTA chromatography, and their kinetic constants were determined by measurements with different DHCA concentrations of between 10 µM and 20 mM. In addition, an expression check by means of SDS PAGE was carried out for all mutants.

The candidates which were most promising in respect of their activity at 10 mM DHCA in comparison with the corresponding wild-type enzyme were:

T188A, T188S, T188G, P185A, L68A, T188S/L68A, T188A/L68A, P185A/T188A with N-terminal and T188A, L68A with C-terminal hexahistidine tag The results obtained here are specified in the following text.

[T188A] N-Terminal Hexahistidine Tag

It emerges that, after reaching the highest specific activity at 0.5 mM DHCA, the activity starts to drop yet again. Like the wild type, the enzyme features pronounced substrate excess inhibition. At approx. 4.5 mM DHCA, the protein still has a residual activity of approximately 50% and at 20 mM of approximately 20%. An asymptotic course establishes.

[T188S] N-Terminal Hexahistidine Tag

Following a maximum specific activity at a substrate concentration of 0.5 mM, substrate excess inhibition is observed. At a substrate concentration of 20 mM DHCA, the enzyme retains a residual activity of over 20% here.

[T188G] N-Terminal Hexahistidine Tag

No pronounced substrate excess inhibition is observed here. However, the activities are relatively low in comparison with the other enzyme variants (approximately 10%), maximum activity being attained at 25 U/mg. At high substrate concentrations (>5 mM), the activity is approximately equal to the other variants which have been described so far. The kinetic parameters were determined with the aid of the course diagrams.

[P185A] N-Terminal Hexahistidine Tag

Again, a pronounced substrate excess inhibition was observed after the maximum specific activity had been reached at a DHCA substrate concentration of 0.25 mM. At a substrate concentration of 10 mM, the residual activity is still 5%.

[L68A] N-Terminal Hexahistidine Tag

In addition to the above-described positions T188 and P185, which had been identified by [Hwang et al., 2013], the 3α-HSDH L68A was generated for comparison purposes. In contrast to the two others, position 68 is in the N-terminal region of the protein. All three positions share the fact that these amino acids form a linkage with the coenzyme, which is why this mutant, too, was generated with an N-terminal His tag and included in the biochemical characterization. To this end, the plasmid pET28a(+) 3α-HSDH (N-His) was modified by means of QuickChange® PCR such that the desired mutant was produced. After cultivation and expression, the proteins were purified by means of Ni-NTA chromatography, the specific activities were determined and their kinetic constants were determined. Again, the DHCA substrate concentration was varied between 10 µM and 10 mM, while the NADH concentration was a constant 0.2 mM.

After the maximum specific activity was reached at a substrate concentration of 0.1 mM DHCA, a pronounced substrate excess inhibition was observed. At a substrate concentration of 1 mM DHCA, the residual activity here amounts to approx. 15%, and at 10 mM, the residual activity amounts to approx. 8%.

To generate the following dual mutants, in each case one existing mutant was remodified by means of Quick Change® PCR as described above, expressed, purified and its parameters were determined.

[L68A/T188A] N-Terminal Hexahistidine Tag

After reaching the maximum specific activity at a substrate concentration of 0.5 mM DHCA, a less pronounced substrate excess inhibition was observed. At a substrate concentration of 1 mM, the residual activity was still 85%, at 10 mM still above 20%. This is comparatively more than in the case of the two single mutants.

[L68A/T188S] N-Terminal Hexahistidine Tag

After the maximum activity at 0.5 mM, a drop in the activities was observed. This can be attributed to pronounced substrate excess inhibition. The course of the curve is the same as that of the corresponding single mutants. At a substrate concentration of 10 mM DHCA, a residual activity of approximately 20% is still observed.

[P185A/T188A] N-Terminal Hexahistidine Tag

After reaching the maximum specific activity at a DHCA substrate concentration of 0.5 mM, substrate excess inhibition was observed. At substrate concentrations of 10 mM DHCA, the residual activity of the enzyme is still approximately 30%. In total, the course of the curves and the substrate inhibition are lower and less pronounced than in the case of the corresponding single mutants, but the activities are markedly lower.

C) Compilation of the Activity Data of the Enzyme Mutants Generated in this Section:

The photometric activity measurements (analogously to Example 1) of the mutants and their kinetic parameters are compiled in tables 14 and 15 herein below.

TABLE 14 summary of the results of the kinetic parameters of the wild-type enzymes and of enzyme variants, determined for the substrate DHCA. The apparent values were listed.

| Mutant | Tag | $v_{max}$ [U/mg] | $K_M$ [µM] | $k_{cat}$ [s$^{-1}$] | $k_{cat}/K_M$ [s$^{-1}$ * mM$^{-1}$] |
|---|---|---|---|---|---|
| Wild type | — | 134 ± 3.8* | X | 62.5 | X |
| Wild type | N | 98.7 ± 4.7* | X | 47.1 | x |
| Wild type | C | 13.86 ± 0.8 | 134.3 ± 25.7 | 6.6 | 49.2 |
| T188A | N | 274.0 ± 11.6* | 94.5 ± 11* | 130.3 | 1371.3 |
| T188S | N | 332.5 ± 59.9* | 312.6 ± 112* | 158.2 | 510.6 |
| T188G | N | 20.3 ± 0.8* | 1458 ± 182.6* | 9.6 | 6.5 |
| P185A | N | 102.8 ± 5.7* | 71.0 ± 11* | 48.5 | 683.1 |
| L68A | N | 290.0 ± 45.4* | 75.4 ± 22.6* | 138.0 | 1840.5 |
| T188A | C | 12.4 ± 12.9* | 2568.3 ± 2.5* | 31.7 | 2.4 |
| L68A/T188A | C | 6.2 ± 0.2* | 350.0 ± 25* | 2.9 | 8.4 |
| L68A | C | 13.9 ± 6.2* | 218.6 ± 38.8* | 18.1 | 177.4 |
| P185A/T188A | N | 36.9 ± 2.6* | 66.9 ± 15* | 17.6 | 262.3 |
| L68A/T188A | N | 233.5 ± 12.5* | 164.4 ± 20.4* | 111.1 | 677.4 |
| L68A/T188S | N | 193.2 ± 11.4* | 169.6 ± 22.6* | 91.8 | 543.0 |

*apparent values
X = value could not be determined

TABLE 15 summary of the results of the kinetic parameters of the wild types and of enzyme variants, determined for the substrate NADH. The apparent values were listed.

| Mutant | Tag | $v_{max}$ [U/mg] | $K_M$ [µM] | $k_{cat}$ [s$^{-1}$] | $k_{cat}/K_M$ [s$^{-1}$ * mM$^{-1}$] |
|---|---|---|---|---|---|
| Wild type | N | 109.0 ± 4.1 | 59.2 ± 6.9 | 47.1 | 795.9 |
| Wild type | WITHOUT | 186.0 ± 6.9 | 46.9 ± 5.9 | 88.5 | 1884.7 |
| Wild type | C | 35.4 ± 8.1 | 427.2 ± 146.3 | 6.6 | 15.4 |
| L68A | N | 138.0 ± 4.4 | 17.1 ± 3.7 | 110.3 | 6461.1 |
| T188A | N | 236.7 ± 15.9 | 111.5 ± 18.2 | 130.3 | 1168.3 |
| T188S | N | 147.2 ± 17.9 | 87.6 ± 29.7 | 96.1 | 1097.0 |
| T188A/P185A | N | 85.9 ± 19.5 | 333.9 ± 137.5 | 17.6 | 52.6 |
| L68A/T188A | N | 228.9 ± 4.7 | 67.5 ± 4.7 | 111.1 | 1645.1 |
| L68A/T188S | N | 188.3 ± 2.7 | 47.4 ± 2.6 | 91.8 | 1936.9 |

In summary, it can be said that the mutants generated show an improvement in their catalytic activity and/or affinity and efficiency in respect of the substrates DHCA and/or NADH in comparison to the corresponding wild-type enzyme.

N-terminal His tag mutants which must be mentioned in particular are [T188A], [T188S], [L68A], [P185A], [L68A/T188S], [L68A/T188A], both for the substrate DHCA and for the substrate NADH.

C-terminal His tag mutants which must be mentioned in particular are [T188A] and [L68A].

Sequences used herein

| SEQ ID NO: | Description | Type |
|---|---|---|
| 1 | 7β-HSDH C. aerofaciens | NA |
| 2 | 7β-HSDH C. aerofaciens | AA |
| 3 | 3α-HSDH C. testosteroni | NA |
| 4 | 3α-HSDH C. testosteroni | AA |
| 5 | 3α-HSDH C. testosteroni wild type + His tag | AA |
| 6 | 3α-HSDH [R34N] | AA |
| 7 | 3α-HSDH [L68A] | AA |
| 8 | 3α-HSDH [R34N/L68A] | AA |

| SEQ ID NO: | Description | Type |
|---|---|---|
| 9 | FDH wild type, M. vaccae | AA |
| 10 | GDH, B. subtilis | NA |
| 11 | GDH B. subtilis | AA |
| 12 | primer | NA |
| 13 | primer | NA |
| 14 | primer | NA |
| 15 | primer | NA |
| 16 | primer | NA |
| 17 | primer | NA |
| 18 | primer | NA |
| 19 | primer | NA |
| 20 | primer | NA |
| 21 | primer | NA |
| 22 | primer | NA |
| 23 | primer | NA |
| 24 | primer | NA |
| 25 | primer | NA |
| 26 | primer | NA |
| 27 | primer | NA |
| 28 | primer | NA |
| 29 | primer | NA |
| 30 | primer | NA |
| 31 | primer | NA |
| 32 | primer | NA |
| 33 | primer | NA |
| 34 | primer | NA |
| 35 | primer | NA |
| 36 | primer | NA |
| 37 | primer | NA |
| 38 | primer | NA |
| 39 | primer | NA |
| 40 | primer | NA |
| 41 | primer | NA |
| 42 | primer | NA |
| 43 | primer | NA |
| 44 | primer | NA |
| 45 | primer | NA |
| 46 | primer | NA |
| 47 | primer | NA |
| 48 | primer | NA |
| 49 | primer | NA |

AA = Amino Acid sequence
NA = Nucleic Acid sequence

The disclosure of the publications mentioned herein is expressly referred to.

The invention claimed is:

1. A 3α-hydroxysteroid dehydrogenase (3α-HSDH), which catalyzes at least the stereospecific enzymatic reduction of a 3-ketosteroid to the corresponding 3-hydroxysteroid, wherein the amino acid sequence of the 3α-HSDH has at least 95% sequence identity to the amino acid sequence of SEQ ID NO:4 and has triple mutation P185$X_1$/T188$X_3$/L68$X_2$;

wherein $X_1$ represents A, T, S, G or V, $X_2$ represents A, G, C, K, S or V and $X_3$ represents A, G, W, S or V;

and wherein the amino acid numbering corresponds to the amino acid sequence of SEQ ID NO: 4.

2. The 3α-hydroxysteroid dehydrogenase (3α-HSDH) of claim 1 which shows the following property profile in comparison with a 3α-HSDH consisting of the amino acid sequence of SEQ ID NO:4:

i) an increased specific activity ($v_{max}$ [U/mg]) for dehydrocholic acid (DHCA) in the enzymatic reduction of DHCA with NADH as cofactor;
ii) a reduced substrate inhibition by DHCA;
iii) an increased specific activity ($v_{max}$ [U/mg]) for NADH in the enzymatic reduction of DHCA with NADH as cofactor; or
iv) any combination of properties i), ii) and iii).

3. A nucleic acid molecule comprising a nucleotide sequence that encodes the 3α-HSDH of claim 1 or claim 2.

4. An expression cassette, comprising at least one nucleotide sequence encoding the 3α-HSDH of claim 1, wherein the expression of said nucleotide sequence is under the control of at least one regulatory sequence.

5. An expression vector, comprising at least one expression cassette of claim 4.

6. A recombinant microorganism comprising at least one nucleic acid molecule of claim 3.

7. The recombinant microorganism of claim 6 further comprising a nucleic acid molecule comprising a nucleotide sequence encoding an additional enzyme selected from the group consisting of hydroxysteroid dehydrogenases (HSDH) and cofactor regenerating dehydrogenases.

8. The recombinant microorganism of claim 7, wherein the HSDH is selected from the group consisting of 7β-HSDHs which are NADPH- and/or NADH-dependent; and wherein the cofactor regenerating dehydrogenase is selected from the group consisting of NADPH-regenerating dehydrogenases and NADH-regenerating dehydrogenases.

9. The recombinant microorganism of claim 8, wherein:
the NADPH-regenerating dehydrogenases are selected from the group consisting of NADPH dehydrogenases, NADPH-regenerating alcohol dehydrogenases (ADH), NADPH-regenerating formate dehydrogenases (FDH), NADPH-regenerating glucose dehydrogenase (GDH), NADPH-regenerating glucose-6-phosphate dehydrogenase (G-6-PDH) and NADPH-regenerating phosphite dehydrogenases (PtDH); and
the NADH-regenerating dehydrogenases are selected from the group consisting of NADH dehydrogenases, NADH-regenerating alcohol dehydrogenases (ADH), NADH-regenerating formate dehydrogenases (FDH), NADH-regenerating glucose dehydrogenases (GDH), NADH-regenerating glucose-6-phosphate dehydrogenases (G6PDH) and NADH-regenerating phosphite dehydrogenases (PtDH).

10. The recombinant microorganism of claim 6 which is a 7α-HSDH knock-out strain.

11. A process for the enzymatic or microbial synthesis of 3α-hydroxysteroid comprising:
reducing a 3-ketosteroid in the presence of the 3α-HSDH of claim 1 or in the presence of a recombinant microorganism comprising the 3α-HSDH of claim 1 to the corresponding 3α-hydroxysteroid.

12. The process of claim 11, wherein the 3-ketosteroid is selected from the group consisting of dehydrocholic acid (DHCA), a salt of DHCA, an amide of DHCA, and an alkyl ester of DHCA.

13. The process of claim 11, further comprising isolating the 3α-hydroxysteroid.

14. The process of claim 11, wherein the 3-ketosteroid reduction takes place in the presence of NADPH and/or NADH.

15. The process of claim 14, wherein the 3-ketosteroid reduction takes place with the consumption of NADPH and/or NADH.

16. The process of claim 15, wherein consumed NADPH is regenerated by coupling with an NADPH-regenerating enzyme, and/or wherein consumed NADH is regenerated by coupling with an NADH-regenerating enzyme.

17. The process of claim 16, wherein:
the NADPH-regenerating enzyme is selected from the group consisting of NADPH dehydrogenases, NADPH-regenerating alcohol dehydrogenases (ADH), NADPH-regenerating formate dehydrogenases (FDH) and an NADPH-regenerating glucose dehydrogenase (GDH), and
the NADPH-regenerating enzyme is selected from the group consisting of NADH-dehydrogenases, NADH-regenerating formate dehydrogenases (FDH), NADH-regenerating alcohol dehydrogenases (ADH), NADH-regenerating glucose-6-phosphate dehydrogenases (G6PDH), NADH-regenerating phosphite dehydrogenases (PtDH) and NADH-regenerating glucose dehydrogenases (GDH).

18. The process of claim 17, wherein the NADPH-regenerating enzyme and/or the NADH-regenerating enzyme are expressed in a recombinant microorganism.

19. The process of claim 17, wherein the NADPH-regenerating enzyme is selected from the group consisting of NADPH-regenerating formate dehydrogenases (FDH) and NADPH-regenerating glucose dehydrogenases (GDH).

20. A process for the preparation of ursodeoxycholic acid (UDCA) of formula (1)

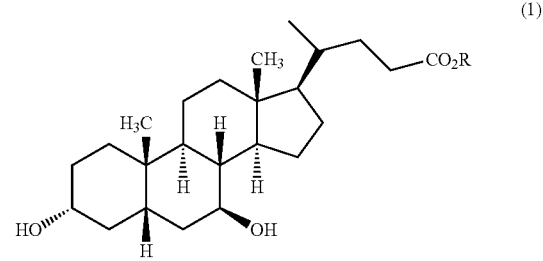

(1)

in which R represents alkyl, H, an alkali metal ion or $N(R^3)_4^+$, wherein the radicals $R^3$ are identical or different and represent H or alkyl, or the group —$CO_2R$ is replaced by the acid amide group —$CONR^1R^2$, wherein $R^1$ and $R^2$ independently of one another represent an alkyl radical;
wherein the process comprises:
a) reducing dehydrocholic acid (DHCA) of formula (2)

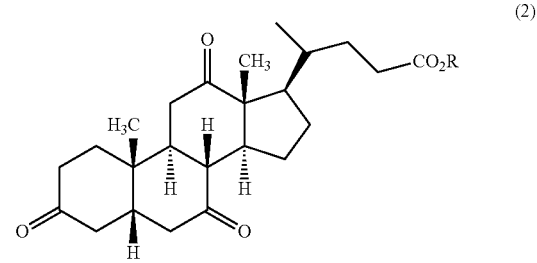

(2)

in which R has the abovementioned meanings or the group —$CO_2R$ is replaced by the acid amide group —$CONR^1R^2$ as defined hereinabove, in the presence of:

1) at least one 7β-HSDH and
2) at least one 3α-HSDH of claim 1 or claim 2, to the corresponding 12-keto-ursodeoxycholic acid (12-keto UDCA) of the formula (3)

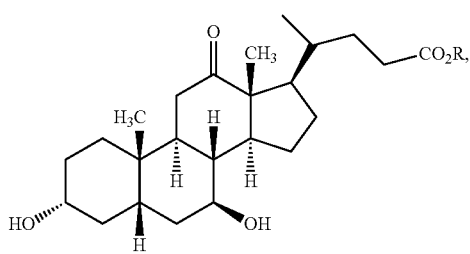
(3)

in which R has the abovementioned meanings or the group —CO₂R is replaced by the acid amide group —CONR¹R² as defined hereinabove; and b) chemically reducing the 12-keto-UDCA of the formula (3) to the UDCA of formula (1).

21. The process of claim 20, further comprising, prior to step a), chemically oxidizing a cholic acid (CA) of formula (4)

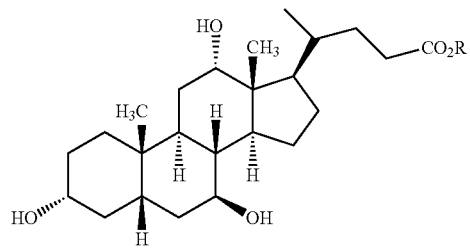
(4)

to the dehydrocholic acid (DHCA) of formula (2)

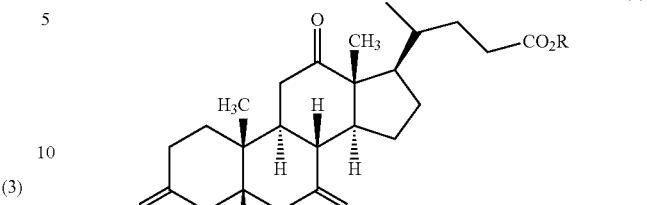
(2)

wherein in the compounds of formulae (2) and (4), R is as defined in claim 20, or the group —CO₂R is replaced by the acid amide group —CONR¹R² as defined in claim 20.

22. The process of claim 20, wherein step a) is carried out in the presence of and with the consumption of NADH and/or NADPH.

23. The process of claim 20, further comprising purifying the ursodeoxycholic acid (UDCA) of formula (1).

24. The process of claim 20, wherein at least step a) is carried out in the presence of a recombinant microorganism comprising at least one nucleic acid molecule that comprises a nucleotide sequence encoding the 3α-HSDH of claim 1 or claim 2.

25. The process of claim 20, wherein step a) is coupled with identical or different cofactor regeneration systems.

26. The 3α-hydroxysteroid dehydrogenase (3α-HSDH) according to claim 1, wherein the 3α-HSDH has a C-terminal extension of 1 to 10 histidine residues and/or an N-terminal extension of 1 to 10 histidine residues.

27. A 3α-hydroxysteroid dehydrogenase (3α-HSDH), which catalyzes at least the stereospecific enzymatic reduction of a 3-ketosteroid to the corresponding 3-hydroxysteroid, wherein the amino acid sequence of the 3α-HSDH has at least 95% sequence identity to the amino acid sequence of SEQ ID NO:4 and has dual mutation P185X₁/T188X₃;

wherein X₁ represents T, S, or V, and
X₃ represents G, W, or V;
and wherein the amino acid numbering corresponds to the amino acid sequence of SEQ ID NO: 4.

28. The 3α-hydroxysteroid dehydrogenase (3α-HSDH) according to claim 27, wherein the 3α-HSDH has a C-terminal extension of 1 to 10 histidine residues and/or an N-terminal extension of 1 to 10 histidine residues.

* * * * *